United States Patent
Woodworth et al.

(10) Patent No.: US 11,033,637 B2
(45) Date of Patent: *Jun. 15, 2021

(54) TARGETED STRUCTURE-SPECIFIC PARTICULATE DELIVERY SYSTEMS

(71) Applicants: University of Maryland, Baltimore, Baltimore, MD (US); The Johns Hopkins University, Baltimore, MD (US)

(72) Inventors: Graeme F. Woodworth, Baltimore, MD (US); Jeffrey A. Winkles, Frederick, MD (US); Anthony J. Kim, Clarksville, MD (US); Craig S. Schneider, Severna Park, MD (US); Justin Hanes, Baltimore, MD (US)

(73) Assignees: University Of Maryland, Baltimore, Baltimore, MD (US); The Johns Hopkins University, Baltimore, MD (US)

( * ) Notice: Subject to any disclaimer, the term of this patent is extended or adjusted under 35 U.S.C. 154(b) by 90 days.

This patent is subject to a terminal disclaimer.

(21) Appl. No.: 15/528,555

(22) PCT Filed: Nov. 20, 2015

(86) PCT No.: PCT/US2015/061853
§ 371 (c)(1),
(2) Date: May 22, 2017

(87) PCT Pub. No.: WO2016/081835
PCT Pub. Date: May 26, 2016

(65) Prior Publication Data
US 2018/0185511 A1  Jul. 5, 2018

Related U.S. Application Data

(60) Provisional application No. 62/083,011, filed on Nov. 21, 2014.

(51) Int. Cl.
| | |
|---|---|
| *A61K 47/68* | (2017.01) |
| *A61K 31/337* | (2006.01) |
| *A61K 31/7048* | (2006.01) |
| *A61K 33/24* | (2019.01) |
| *A61K 9/00* | (2006.01) |
| *A61K 31/704* | (2006.01) |
| *A61P 23/00* | (2006.01) |
| *A61K 47/69* | (2017.01) |
| *A61P 35/00* | (2006.01) |

(52) U.S. Cl.
CPC ......... *A61K 47/6865* (2017.08); *A61K 9/007* (2013.01); *A61K 9/0019* (2013.01); *A61K 9/0041* (2013.01); *A61K 9/0085* (2013.01); *A61K 31/337* (2013.01); *A61K 31/704* (2013.01); *A61K 31/7048* (2013.01); *A61K 33/24* (2013.01); *A61K 47/6849* (2017.08); *A61K 47/6851* (2017.08); *A61K 47/6913* (2017.08); *A61K 47/6933* (2017.08); *A61K 47/6937* (2017.08); *A61P 23/00* (2018.01); *A61P 35/00* (2018.01)

(58) Field of Classification Search
None
See application file for complete search history.

(56) References Cited

U.S. PATENT DOCUMENTS

| | | | |
|---|---|---|---|
| 2011/0224288 A1 | 9/2011 | Zale et al. | |
| 2014/0023715 A1 | 1/2014 | Yang et al. | |
| 2014/0044791 A1* | 2/2014 | Basilion | A61K 47/6935 424/491 |

FOREIGN PATENT DOCUMENTS

WO    WO2013040499    *  3/2013

OTHER PUBLICATIONS

Bobo, R.H., et al., "Convection-enhanced delivery of macromolecules in the brain," Proc. Natl. Acad. Sci. USA 1994, pp. 2076-2080, vol. 91.
Brem, H., et al., "Placebo-controlled trial of safety and efficacy of intraoperative controlled delivery by biodegradable polymers of chemotherapy for recurrent gliomas," Lancet 1995, pp. 1008-1012, vol. 345.
Dhruv, H., et al., "Structural basis and targeting of the interaction between fibroblast growth factor-inducible 14 and tumor necrosis factor-like weak inducer of apoptosis," J Biol Chem 2013, pp. 32261-32276, vol. 288, No. 45.
Fung, L.K., et al., "Chemotherapeutic drugs released from polymers: distribution of 1,3-bis(2-chloroethyl)-I-nitrosourea in the rat brain," Pharm Res 1996, pp. 671-682, vol. 13, No. 5.
Kim, A.J., et al., "Use of single-site-functionalized PEG dendrons to prepare gene vectors that penetrate human mucus barriers," Angew. Chem. Int. Ed. 2013, pp. 3985-3988, vol. 52.
Madhankumar, A.B., et al., "Interleukin-13 receptor-targeted nanovesicles are a potential therapy for glioblastoma multiforme," Mol Cancer Ther 2006, pp. 3162-3169, vol. 5, No. 12.
Meighan-Mantha, R.L., et al., "The mitogen-inducible Fn14 gene encodes a type I transmembrane protein that modulates fibroblast adhesion and migration," J Biol Chem 1999, pp. 33166-33176, vol. 274, No. 46.

(Continued)

*Primary Examiner* — Robert A Wax
*Assistant Examiner* — Randeep Singh
(74) *Attorney, Agent, or Firm* — Wolter Van Dyke Davis, PLLC; Eugene J. Molinelli; Martha Cassidy

(57) ABSTRACT

Provided are targeted structure-specific particulate-based delivery systems comprising: a nanoparticle; a PEG polymer coating on the surface of the nanoparticle; a targeting moiety conjugated on a surface of the nanoparticle and configured to promote specific binding to a cell surface molecule expressed by a target cell; and a biologically active agent in or on the nanoparticle, wherein the biologically active agent is selected to enhance a desired response in a target cell intracellularly or extracellularly. Methods of treating a disease or disorder administering the delivery system are contemplated.

14 Claims, 23 Drawing Sheets

(56) References Cited

OTHER PUBLICATIONS

Nakayama, M., et al., "Fibroblast growth factor-inducible 14 mediates multiple pathways of TWEAK-induced cell death," J Immunol. 2003, pp. 341-348, vol. 170.

Nance, E.A., et al., "A dense poly(ethylene glycol) coating improves penetration of large polymeric nanoparticles within brain tissue," Sci Transl Med 2012, pp. 1-8, vol. 4, Issue 149.

Nance, E., et al., "Non-invasive delivery of stealth, brain-penetrating nanoparticles across the blood-brain barrier using MRI-guided focused ultrasound," J Control Release 2014, pp. 123-132, vol. 189.

Rich, J.N. and Bigner, D.D., "Development of novel targeted therapies in the treatment of malignant glioma," Nat Rev Drug Discov 2004, pp. 430-446, vol. 3, No. 5.

Tran, N.L., et al., "Increased fibroblast growth factor-inducible 14 expression levels promote glioma cell invasion via Rac1 and nuclear factor-kappaB and correlate with poor patient outcome," Cancer Res 2006, pp. 9535-9542, vol. 66, No. 19.

Veiseh, O., et al., "Specific targeting of brain tumors with an optical/magnetic resonance imaging nanoprobe across the blood-brain barrier," Cancer Res 2009, pp. 6200-6207, vol. 69, No. 15.

Whitsett, T.G., et al., "Elevated expression of Fn14 in non-small cell lung cancer correlates with activated EGFR and promotes tumor cell migration and invasion," Am J Pathol 2012, pp. 111-120, No. 181, vol. 1.

Willis, A.L., et al., "The fibroblast growth factor-inducible 14 receptor is highly expressed in HER2-positive breast tumors and regulates breast cancer cell invasive capacity," Mol Cancer Res 2008, pp. 725-734, vol. 6, No. 5.

Winkles, J.A., "The TWEAK-Fn14 cytokine-receptor axis: discovery, biology and therapeutic targeting," Nat Rev Drug Discov. 2008, pp. 411-425, vol. 7, No. 5.

Yin, J., et a., "AR-Regulated TWEAK-FN14 Pathway Promotes Prostate Cancer Bone Metastasis," Cancer Res 2014, pp. 4306-4317, vol. 74, No. 16.

Zhou, J., et al., "Highly penetrative, drug-loaded nanocarriers improve treatment of glioblastoma," Proc Natl Acad Sci USA 2013, pp. 11751-11756, vol. 110, No. 29.

Zhou, H., et al., "The TWEAK receptor Fn14 is a therapeutic target in melanoma: immunotoxins targeting Fn14 receptor for malignant melanoma treatment," J Invest Dermatol 2013, pp. 1052-1062, vol. 133.

Zhou, et al., "Antitumor activity of a humanized, bivalent immunotoxin targeting fnI4-positive solid tumors," Cancer Res 2013, pp. 4439-4450, vol. 73, No. 14.

Zhou, H., et al', "Development and characterization of a potent immunoconjugate targeting the Fn14 receptor on solid tumor cells," Mol Cancer Ther, 2011, pp. 1276-1288, vol. 10, No. 7.

Kanapathipillai, M., et al., "Nanoparticle targeting of anti-cancer drugs that alter intracellular signaling or influence the tumor microenvironment," Advanced Drug Delivery Reviews 2014, pp. 107-118, vols. 79-80.

Schneider, C., et al., "Minimizing the Non-specific Binding of Nanoparticles to the Brain Enables Active Targeting of Fn14-positive Glioblastoma Cells," Biomaterials 2015, pp. 42-51, vols. vol. 42.

ISA/KR: International Search Report and Written Opinion, International Patent Application No. PCT/US2015/061853, dated Aug. 10, 2016, pp. 1-14.

Bertrand et al. (2014). Cancer nanotechnology: The impact of passive and active targeting in the era of modern cancer biology. Advanced Drug Delivery Reviews, 66: 2-26.

Dancy et al. (2016). Non-specific binding and steric hindrance thresholds for penetration of particulate drug carriers within tumor tissue. Journal of Controlled Release 238:139-148.

Zhou et al. (2014). Development of human serine protease-based therapeutics targeting Fn14 and identification of Fn14 as a new target overexpressed in TNBC. Molecular Cancer Therapeutics 13:2688-2705.

European Extended Search Report, EP Patent Application No. 15860689.7, dated Jun. 13, 2018, pp. 1-7.

Michaelson, J., et al., Development of an Fn14 agonistic antibody as an anti-tumor agent,"mAbs" pp. 362-375, vol. 3, Issue 4 (2011).

Liu et al., "A strategy for precision engineering of nanoparticles of biodegradable copolymers for quantitative control of drug delivery", 2010, Biomaterials, vol. 31 , pp. 9145-9155.

* cited by examiner

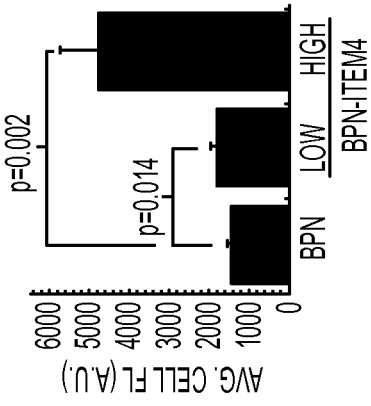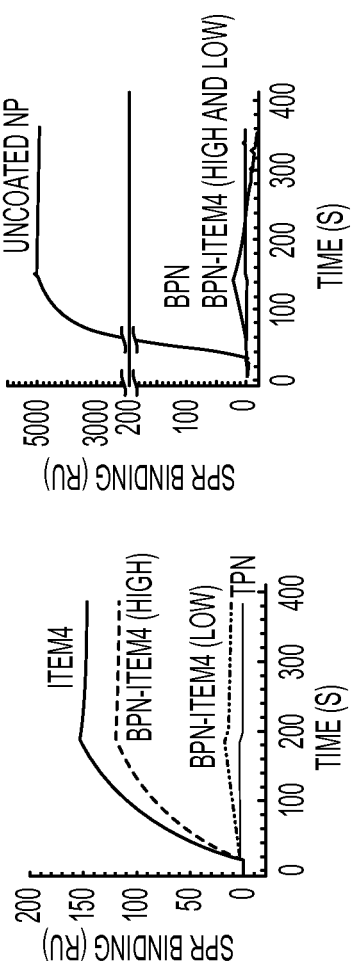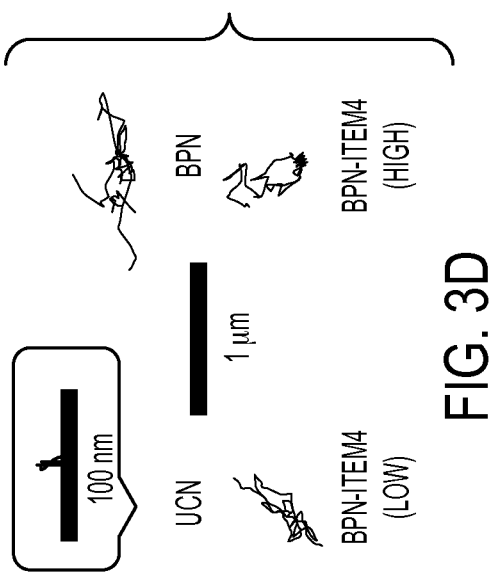
FIG. 3A  FIG. 3B  FIG. 3C  FIG. 3D

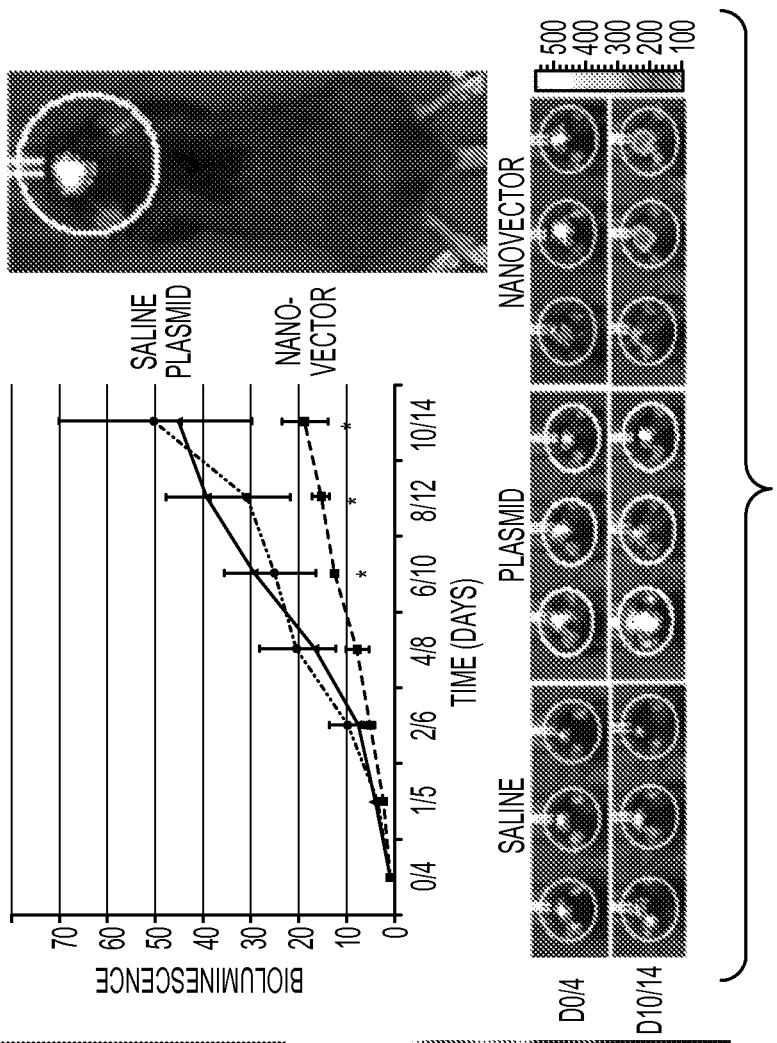
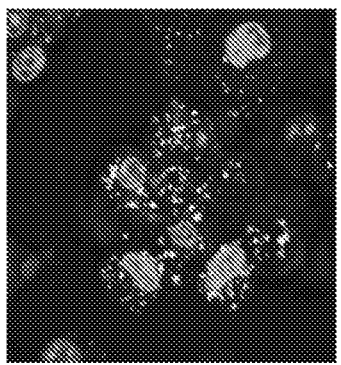
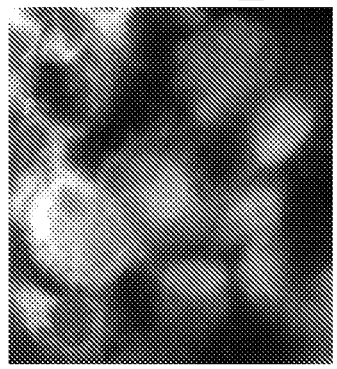
FIG. 6A
FIG. 6B
FIG. 6C

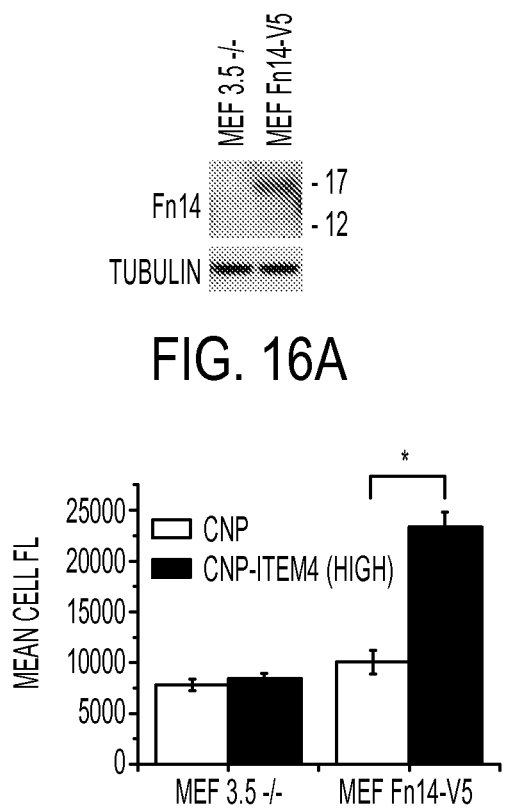
FIG. 16A
FIG. 16C
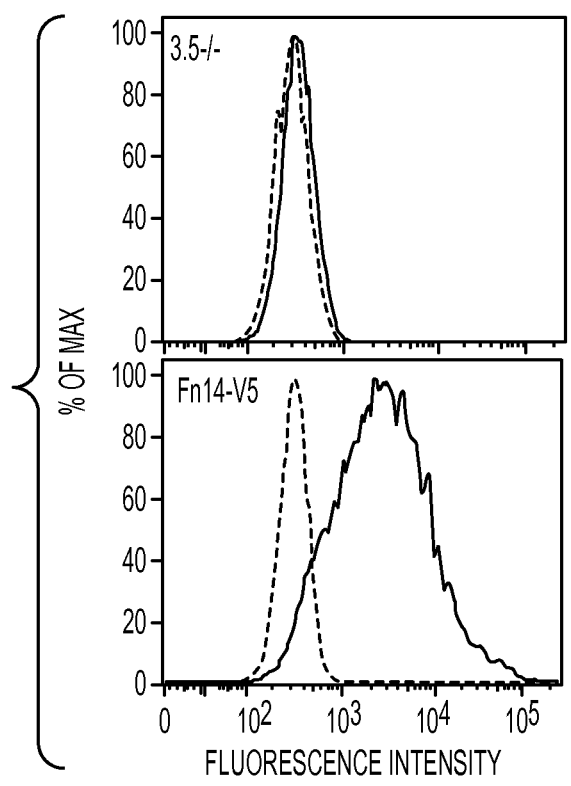
FIG. 16B

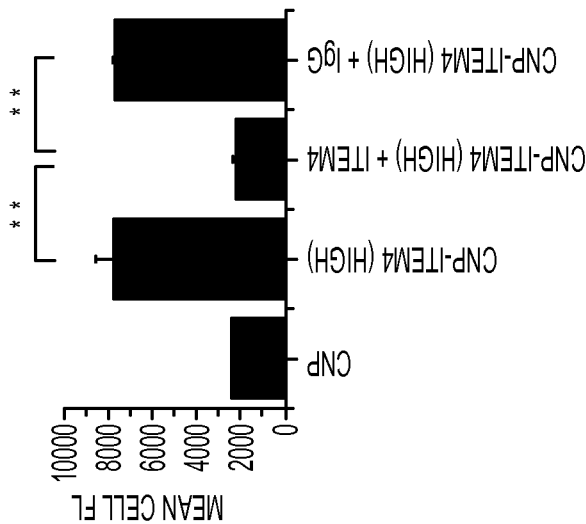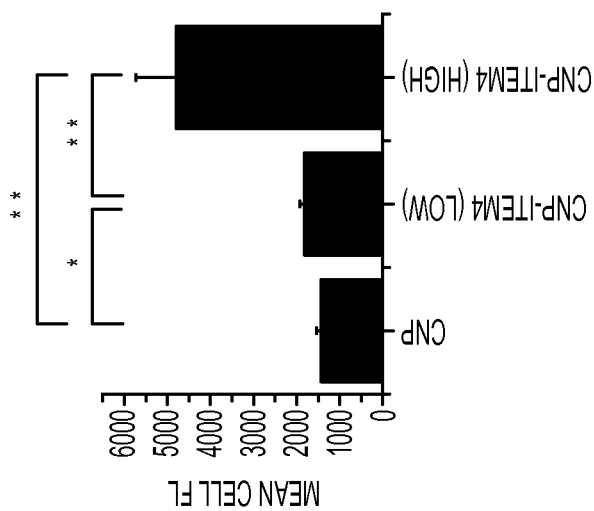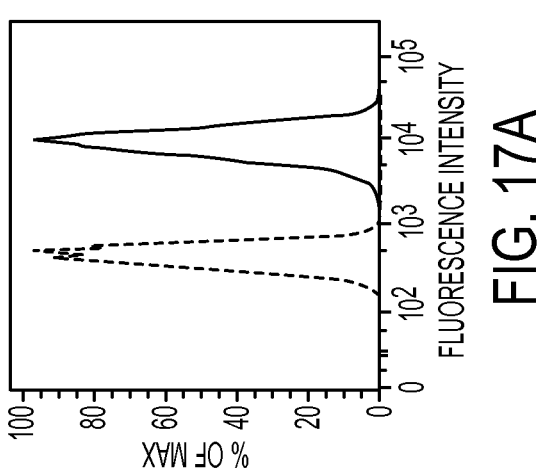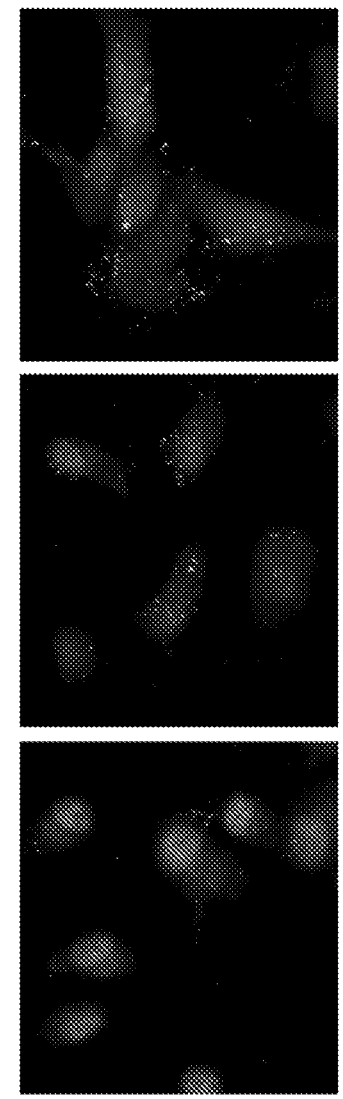
FIG. 17A FIG. 17B FIG. 17C FIG. 17D FIG. 17E FIG. 17F FIG. 17G PS-PEG or PS-PEG-ITEM4

PS-PEG

PS-PEG-ITEM4

TARGETED STRUCTURE-SPECIFIC PARTICULATE DELIVERY SYSTEMS

CROSS-REFERENCE TO RELATED APPLICATIONS

This application is a 371 national stage application of PCT Application No. PCT/US2015/061,853 filed Nov. 20, 2015 which claims benefit of Provisional Application 62/083,011, filed Nov. 21, 2014, the entire contents of which are hereby incorporated by reference as if fully set forth herein, under 35 U.S.C. § 119(e).

STATEMENT OF GOVERNMENT INTEREST

This invention was made with government support under Grant Numbers NS080223, CA164789, CA151838, EB018370 & NS090430 awarded by the National Institutes of Health. The government has certain rights in the invention.

BACKGROUND

A broad range of cancers including glioblastoma (GBM), melanoma, breast, prostate, non-small cell lung cancer and others overexpress fibroblast growth factor-inducible 14 ("Fn14"). Of specific interest is GBM. This is the most common form of primary brain cancer and takes more than 15,000 lives in the USA each year, often with devastating neurological consequences. GBM is not curable with surgery alone because tumor cells invade the surrounding brain, rendering complete resection unsafe. Current adjuvant therapies use fractionated external beam radiation combined with the orally delivered chemotherapeutic agent Temodar®. Despite these treatments, median survival is still less than 18 months. A major limitation is believed to be delivery of therapeutics to invasive cancer cells, often found many centimeters away from the main tumor mass within functioning brain tissue. Novel treatment approaches such as Gliadel®, a biodegradable chemo-loaded polymer wafer that is implanted in the brain after tumor resection, only provides a modest improvement in median survival time due in part to limited drug penetration into the surrounding brain tissue.

The location of invasive tumor cells presents several barriers to therapeutic delivery. The blood-brain barrier (BBB) regulates the trafficking of molecules to and from the brain. Unresectable tumor cells are consistently found in brain regions with relatively healthy blood vessels. Therapeutics can potentially be delivered to the brain by receptor-mediated transport across the BBB, mechanical disruption of the BBB via focused ultrasound, or using hyperosmotic agents; however, it is not yet clear whether sufficient therapeutic doses can be safely achieved. Local delivery approaches, such as Gliadel®, wafer or convection-enhanced delivery (CED), avoid the complexities associated with the BBB, delivering therapies more directly and deeper into brain tissue. The safety and feasibility of these approaches in human clinical studies has been repeatedly shown, yet penetration of substances is often still limited. This is largely due to the anisotropic and electrostatically charged extracellular space (ECS) found between brain cells, comprising 15-20% of total brain volume, which acts as a 'brain penetration barrier' (BPB). The surrounding extracellular matrix (ECM) and brain cells act as sinks for small molecule drugs, proteins, viral particles, and standard nanoparticles, thereby limiting their diffusion and distribution throughout the brain and effective therapeutic results. In addition, perivascular channels serve as critical and efficient brain clearance mechanisms for small molecules and particulate delivery systems, further limiting the distribution, residence time, and efficacy of therapeutic agents.

Targeted therapeutics offer the potential for delivering therapies directly to invasive brain cancer cells to improve the desired treatment effects while minimizing unwanted toxicity. Previous studies exploring this approach for invasive brain cancer have included targeting tumor cell surface molecules and tumor-associated ECM components. However, most targeted therapeutic formulations have yet to show improvements in disease progression or survival.

Therefore, a need exists for the development of a treatment for a disorder or disease of the brain such as GBM that can deliver therapeutics to invading tumor cells outside an area that is safe for surgical removal. The present invention meets that need by providing for a targeted structure-specific particulate-delivery system having (i) a particle, (ii) a dense, PEG surface coating (iii) a targeting moiety conjugated on the surface of the particle such as an ITEM 4 monoclonal antibody (monoclonal antibody) that recognizes the cell surface receptor Fn14 on a tumor cell of interest, and (iv) a biologically active agent such as a therapeutic agents (anti-cancer agents), diagnostic agents (e.g. contrast agents; radionuclides; and fluorescent, luminescent, and magnetic moieties), prophylactic agents (e.g. vaccines), nutraceutical agents (e.g. vitamins, minerals, etc.), nucleic acids (e.g. DNA and RNA), and imaging agents (e.g., via magnetic resonance imaging, optical imaging, positron emission tomography, X-ray computed tomography, and ultrasound imaging). This particle delivery system can target disease-specific structures with minimized non-specific binding within the microenvironment and/or circulation and highly specific binding to the disease-specific structures.

SUMMARY

It has been discovered that tumor cells (i.e., glioblastoma cells) and diseased cells of the brain due to neurodegenerative diseases or neurological disorders (i.e., Alzheimer's Disease ("AD"), Parkinson's Disease ("PD") or Huntington's Disease ("HD")) and elsewhere in the body can be specifically targeted by using a particulate delivery system that is loaded with biologically active agents. Other conditions suitable for targeted effects include but are not limited to lung cancer, prostate cancer, breast cancer, medulloblastoma, radiation injury, and inflammatory diseases. The particulate delivery system is able to bind to a target on the tumor cell or disease specific region. Specifically, binding can occur using a biologically active agent such as an Fn14 monoclonal antibody that is specific for the Fn14 protein on the cell surface of an Fn14 positive cancer cell (i.e., glioblastoma cell) in patients with cancer. These Fn14 monoclonal antibody-decorated particles are designed and engineered to penetrate brain tissue and selectively bind to Fn14 but not the brain and/or tumor microenvironment such as brain ECM proteins. Minimizing non-specific binding and size-related steric restrictions of targeted particles in the brain may greatly improve the access of particulate delivery systems to remote brain tumor cells and other brain targets.

In certain embodiments, a targeted structure-specific particulate-based delivery system comprises a nanoparticle having a hydrodynamic diameter between 4 nm and 200 nm. The nanoparticle is coated with a polyethylene glycol (PEG) polymer to achieve a surface density of at least 0.1 PEG molecules per $nm^2$ and configured to penetrate brain and/or tumor tissue thereby enabling improved distribution within brain tissue. Targeting moieties such as Fn14 monoclonal antibody ITEM4 or modified versions such ITEM4-SH are conjugated on a surface of the nanoparticle and configured to promote specific binding to a cell surface molecule such as Fn14 protein expressed by the target cell (i.e., a tumor cell such as a glioblastoma cell). The nanoparticle may further comprise a biologically active agent such as therapeutic agents (anti-cancer agents), diagnostic agents (e.g. contrast agents; radionuclides; and fluorescent, luminescent, and magnetic moieties), prophylactic agents (e.g. vaccines), nutraceutical agents (e.g. vitamins, minerals, etc.), nucleic acids (e.g. DNA and RNA), and imaging agents (e.g., via magnetic resonance imaging, optical imaging, positron emission tomography, X-ray computed tomography, and ultrasound imaging) in or on the nanoparticle. The biologically active agent is selected to enhance a desired response in the target cell intracellularly or extracellularly or region.

In other embodiments, methods are provided for treating a disease or disorder of the brain (e.g., a tumor such as glioblastoma, neurological disorder, neurodegenerative disease, brain injury, or trauma), lung, or breast by administering to a patient in need thereof a therapeutically effective amount of the optimized particulate therapeutic formulation either locally or systemically.

In certain embodiments, pharmaceutical compositions and kits encompassing them are provided. The pharmaceutical composition may comprise a nanoparticle as described above and a pharmaceutically acceptable excipient for delivery. The pharmaceutical compositions can further comprise imaging agents via magnetic resonance imaging, optical imaging, positron emission tomography, X-ray computed tomography, and ultrasound imaging. It can be delivered to the brain via direct approaches (i.e. stereotactic injection, convection enhanced delivery), systemic approaches (i.e. intravenous, intra-arterial), intra-thecal, and others.

These and other features, aspects, and advantages of the present invention will become better understood with regard to the following description, appended claims, and accompanying figures.

BRIEF DESCRIPTION OF THE DRAWINGS

The following drawings form part of the present specification and are included to further demonstrate certain embodiments of the present invention. The invention may be better understood by reference to one or more of these drawings in combination with the detailed description of specific embodiments presented herein.

FIG. 3A-3D are graphs illustrating (A) surface plasmon resonance (SPR) analysis measuring the binding of the Fn14 monoclonal antibody ITEM4, uncoated polystyrene NPs and BPNs with varying surface densities of ITEM4 to the Fn14 receptor, (B) SPR analysis measuring the binding of uncoated polystyrene NPs and BPNs with varying surface densities of ITEM4 to mouse brain ECM, (C) human U87 glioma cells treated with fluorescent non-targeted BPNs or BPNs with varying surface densities of ITEM4 and analyzed by flow cytometry; and (D) individual particle trajectories in fresh rodent brain tissue were determined using multiple particle tracking (MPT) assay and high resolution microscopy, according to an embodiment;

FIG. 6A-6C are photographs and a graph illustrating nanoparticle-based delivery systems comprising polymeric nanovectors modulating mouse glioma. (A) Nanovectors efficiently enter mouse glioma cells (GL261). (B) After entering cells, nanovectors effectively deliver a plasmid gene construct with green fluorescent reporter and inhibitor RNA for luciferase (shLuc) to GL261 cells that constitutively express luciferase. (C) Bio-luminescent imaging (BLI) of GL261L cells in vivo showing a decrease in BLI signal over time in animals treated with nanovectors carrying shLuc plasmid, according to an embodiment;

FIG. 16A-16C are (A) Western blot image and (B) FACS data showing Fn14 expression in Fn14-negative and Fn14 lentivirus-infected (V5) murine embryonic fibroblast ("MEF") cell lines and (C) graph illustrating nanoparticle uptake in Fn14-positive and Fn14-negative MEFs, according to an embodiment;

FIG. 17A-17G are graphs and photographs illustrating (A) FACS analysis of Fn14 expression in U87 GBM cells, (B-G) analysis of CNP, CNP-ITEM4 (low), and CNP-ITEM4 (high) uptake in Fn14-positive U87 GBM cells, according to an embodiment;

Figure 1:
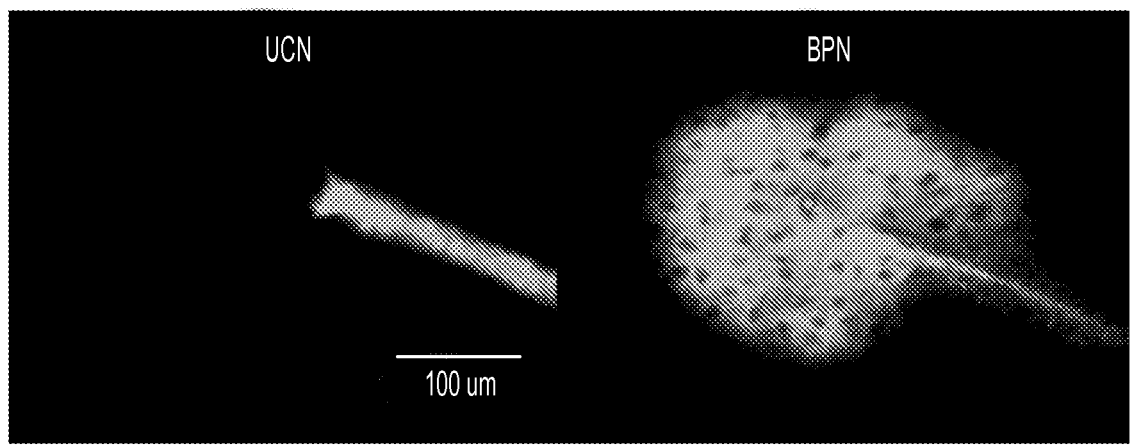
FIG. 1 is a photograph showing in vivo imaging of uncoated nanoparticles (UCN) and brain penetrating nanoparticle (BPN) movement in the mouse brain, according to an embodiment.

In the Summary above, in the Detailed Description, and the claims below, as well as the accompanying figures, reference is made to particular features of the invention. It is to be understood that the disclosure of the invention in this specification includes all possible combinations of such particular features. For example, where a particular feature is disclosed in the context of a particular embodiment or embodiment of the invention, or a particular claim, that feature can also be used, to the extent possible, in combination with and/or in the context of other particular embodiments and embodiments of the invention, and in the invention generally. For the purposes of explanation, numerous specific details are set forth in order to provide a thorough understanding of the present invention. It will be apparent, however, to one skilled in the art that the present invention may be practiced without these specific details.

DETAILED DESCRIPTION

In the following description, for the purposes of explanation, numerous specific details are set forth in order to provide a thorough understanding of the present invention. It will be apparent, however, to one skilled in the art that the present invention may be practiced without these specific details.

It has now been discovered that targeted structure-specific particulate-based delivery systems encompassing a specific-sized nanoparticle can be used for treatment of disorders and diseases of the brain, lung, and breast. Specifically, the nanoparticle-based delivery system can diffuse and penetrate within brain tissue and selectively target remote experimental GBM tumors. Tumor specific targeting of nanoparticles can be achieved through a balance of minimal non-specific binding and specific binding to distant glioma cells. This approach may improve drug efficacy while limiting many of the side effects and risks of free drug and non-targeted therapies.

In order that the invention may be readily understood and put into practical effect, particular preferred embodiments will now be described by way of the following non-limiting examples.

1. Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference.

Generally, nomenclatures used in connection with, and techniques of, cell and tissue culture, molecular biology, immunology, microbiology, genetics, protein, and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. [1]-[4]. Unless defined otherwise, all technical and scientific terms used herein have the same meaning as commonly understood by one of ordinary skill in the art.

The term "administering" as used herein, means a targeted structure-specific particulate delivery system may be administered or performed using any of the various methods or for delivering a biologically active agent.

As used herein, the term "amphiphilic" refers to a property where a molecule has both a polar portion and a non-polar portion. Often, an amphiphilic compound has a polar head attached to a long hydrophobic tail.

The term "biologically active agent" may include, for example, therapeutic agents (anti-cancer agents), diagnostic agents (e.g. contrast agents; radionuclides; and fluorescent, luminescent, and magnetic moieties), prophylactic agents (e.g. vaccines), nutraceutical agents (e.g. vitamins, minerals, etc.), nucleic acids (e.g. DNA and RNA), and imaging agents (e.g., via magnetic resonance imaging, optical imaging, positron emission tomography, X-ray computed tomography, and ultrasound imaging) may be delivered by the disclosed nanoparticles. Exemplary agents to be delivered in accordance with the present invention include, but are not limited to, drugs, small molecules (e.g. cytotoxic agents), nucleic acids (e.g., siRNA, RNAi, and microRNA agents), proteins (e.g. antibodies), peptides, lipids, carbohydrates, hormones, metals, radioactive elements and compounds, vaccines, immunological agents, etc., and/or combinations thereof. In some embodiments, the agent to be delivered is an agent useful in the treatment of cancer (e.g., brain cancer, specifically glioblastoma).

The term "bind" or "binding," as used herein, refers to the interaction between a corresponding pair of molecules or portions thereof that exhibit mutual affinity or binding capacity, typically due to specific or non-specific binding or interaction, including, but not limited to, biochemical, physiological, and/or chemical interactions. "Biological binding" defines a type of interaction that occurs between pairs of molecules including proteins, nucleic acids, glycoproteins, carbohydrates, hormones, or the like. The term "binding partner" refers to a molecule that can undergo binding with a particular molecule. "Specific binding" refers to molecules, such as polynucleotides, that are able to bind to or recognize a binding partner (or a limited number of binding partners) to a substantially higher degree than to other, similar biological entities.

The term "biodegradable" as used herein means that the materials degrades or breaks down into its component subunits, or digestion, e.g., by a biochemical process, of the material into smaller (e.g., non-polymeric) subunits.

The term "cancer" includes pre-malignant as well as malignant cancers. Cancers include, but are not limited to, brain or central nervous system cancer, prostate, gastric cancer, colorectal cancer, skin cancer, e.g., melanomas or basal cell carcinomas, lung cancer, breast cancer, cancers of the head and neck, bronchus cancer, pancreatic cancer, urinary bladder cancer, peripheral nervous system cancer, esophageal cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. "Cancer cells" can be in the form of a tumor, exist alone within a subject, or be cell lines derived from a cancer. Cancer can be associated with a variety of physical symptoms.

The term "CD266" or "TWEAK R (TNFRSF12A)", as used herein is also known as Fn14 (fibroblast growth factor-inducible 14) and is a receptor for CD255/TWEAK/TNFSF12, the TNF-like weak inducer of apoptosis. CD266 is expressed on endothelial cells, as well as on many cancer tissues, and plays a role in CD255-induced endothelial cell migration, proliferation, and angiogenesis as well as CD255-induced cancer cell growth, migration and invasion. The CD255-CD266 interaction, or antibody-mediated triggering of CD266 is also able to induce apoptosis and necrosis in certain CD266-positive cells (including some tumor cells), which might have therapeutic potential.

The term "controlled release" (and variants of that term) as used herein (e.g., in the context of "controlled-release system") is generally meant to encompass release of a substance (e.g., a drug) at a selected site or otherwise controllable in rate, interval, and/or amount. Controlled release encompasses, but is not necessarily limited to, substantially continuous delivery, patterned delivery (e.g., intermittent delivery over a period of time that is interrupted by regular or irregular time intervals), and delivery of a bolus of a selected substance (e.g., as a predetermined, discrete amount if a substance over a relatively short period of time (e.g., a few seconds or minutes)).

The term "diameter" is art-recognized and is used herein to refer to either of the physical diameter or the hydrodynamic diameter of the nanoparticle. The diameter of an essentially spherical nanoparticle may refer to the physical or hydrodynamic diameter. The diameter of a nonspherical nanoparticle may refer preferentially to the hydrodynamic diameter. As used herein, the diameter of a non-spherical nanoparticle may refer to the largest linear distance between two points on the surface of the nanoparticle. When referring to multiple nanoparticles, the diameter of the nanoparticles typically refers to the average diameter of the nanoparticles. Nanoparticle diameter can be measured using a variety of techniques in the art including, but not limited to, dynamic light scattering. In certain embodiments, the nanoparticle has a diameter of about 100 nm, 110 nm, 120 nm, 130 nm, 140 nm, 150 nm, 160 nm, 170 nm, 180 nm, or 190 nm. Or, the nanoparticle has a diameter between 50 nm and 100 nm. In other embodiments, the nanoparticle has a diameter between 110 nm and 115 nm.

The term "extracellular matrix" ("ECM") as used herein, is a collection of extracellular molecules that provides structural and biochemical support to the surrounding cells. The composition of ECM varies between multicellular structures; however, cell adhesion, cell-to-cell communication and differentiation are common functions of the ECM. The animal extracellular matrix includes the interstitial matrix and the basement membrane. Interstitial matrix is present between various animal cells (i.e., in the intercellular spaces). Gels of polysaccharides and fibrous proteins fill the interstitial space and act as a compression buffer against the stress placed on the ECM. Basement membranes are sheet-like depositions of ECM on which various epithelial cells rest. The extracellular matrix of the adult brain tissue has a unique composition. The striking feature of this matrix is the prominence of lecticans, proteoglycans that contain a lectin domain and a hyaluronic acid-binding domain. Hyaluronic acid and tenascin family adhesive/anti-adhesive proteins are also abundant. Matrix proteins common in other tissues are nearly absent in adult brain. The brain extracellular matrix appears to have trophic effects on neuronal cells and affect neurite outgrowth. The unique composition of this matrix may be responsible for the resistance of brain tissue toward invasion by tumors of neuronal and non-neuronal origin. The role of ECM in neurological development, function and degeneration has evolved from a simplistic physical adhesion to a system of intricate cellular signaling. While most cells require ECM adhesion to survive, it is now clear that differentiated function is intimately dependent upon cellular interaction with the ECM. Therefore, it is not surprising that the ECM is increasingly found to be involved in the enigmatic process of neurodegeneration and plays a central role in numerous neurological diseases.

The term, "Fn14" as used herein, means fibroblast growth factor-inducible 14 and is a member of the tumor necrosis factor (TNF) receptor family that is induced in a variety of cell types in situations of tissue injury. Fn14 becomes activated by TNF-like weak inducer of apoptosis (TWEAK), a typical member of the TNF ligand family. Fn14 is an FGF-inducible receptor. It is often expressed at low levels on cells of normal tissues, and can be upregulated in injury or disease, or on cancer (e.g., tumor) cells. Without being bound by theory, it is believed that stimulation of Fn14 by an Fn14 ligand (e.g., TWEAK) can in some cases induce tumor cell death, and that an anti-Fn14 antibody will also be effective in killing tumor cells. It is also believed that Fn14 is overexpressed in human tumors. An anti-Fn14 antibody can trigger tumor cell death and therefore be therapeutically beneficial in treating cancer. The sequence of human Fn14 is shown as:
MARGSLRRLLRLL-
VLGLWLALLRSVAGEQAPGTAPCSRGSS-
WSADLDKCMDCASCRA RPHSDFCLGCAAAPPAP- FRLLWPILGGALSLTFVLGLLSGFLVWRRCRRREKFTT-PIEETG GEGCPAVALIQ (SEQ ID NO:1). Additional Fn14 protein sequences include: mouse Fn14 (e.g., NCBI accession no. AAF07882 or NP_ 038777 or Q9CR75 or AAH25860), human Fn14 (e.g., NCBI accession no. NP_ 057723 or BAA94792 or Q9NP84 or AAH02718 or AAF69108); rat Fn14 (e.g., NCBI accession no. NP_851600 or AAH60537); and *Xenopus* Fn14 (e.g., NCBI accession no. AAR21225 or NP_ 001083640). These Fn14 proteins can be used, e.g., as an immunogen to prepare anti-Fn14 antibodies. Anti-Fn14 antibodies can then be screened to identify agonist antibodies, as described herein.

As used herein, the term "gene construct" can mean a construct which is capable of expressing, one or more gene(s) or sequence(s) of interest in a host cell. In certain embodiments, the "gene construct" is delivered by a nanoparticle such as a polymeric nanogene vector. These highly compacted pH-responsive nanoparticles can mediate transgene silencing in gliomas and can be targeted to Fn14-positive glioblastoma cells.

As used herein, the term "inhibits growth of cancer cells" or "inhibiting growth of cancer cells" refers to any slowing of the rate of cancer cell proliferation and/or migration, arrest of cancer cell proliferation and/or migration, or killing of cancer cells, such that the rate of cancer cell growth is reduced in comparison with the observed or predicted rate of growth of an untreated control cancer cell. The term "inhibits growth" can also refer to a reduction in size or disappearance of a cancer cell or tumor, as well as to a reduction in its metastatic potential. Preferably, such an inhibition at the cellular level may reduce the size, deter the growth, reduce the aggressiveness, or prevent or inhibit metastasis of a cancer in a patient.

As used herein, the term "intracranial" means within the cranium or at or near the dorsal end of the spinal cord and includes the medulla, brain stem, pons, cerebellum and cerebrum.

As used herein, the terms "incorporated" and "encapsulated" refers to incorporating, formulating, or otherwise including an active agent into and/or onto a composition that allows for release, such as sustained release, of such agent in the desired application. The terms contemplate any manner by which a biologically active agent or other material is incorporated into a polymer matrix, including for example: attached to a monomer of such polymer (by covalent, ionic, or other binding interaction), physical admixture, enveloping the agent in a coating layer of polymer, and having such monomer be part of the polymerization to give a polymeric formulation, distributed throughout the polymeric matrix, appended to the surface of the polymeric matrix (by covalent or other binding interactions), encapsulated inside the polymeric matrix, etc. The term "co-incorporation" or "co-encapsulation" refers to the incorporation of a biologically active agent or other material and at least one other biologically active agent or other material in a subject composition.

The term ITEM4, as used herein, is an antibody that recognizes human CD266, otherwise known as Fn14/TWEAK Receptor, a 14 kDa type I transmembrane glycoprotein and member of the tumor necrosis factor receptor superfamily (TNFRSF12A) expressed by a few normal tissues and at much elevated levels by most human tumour types. The ITEM4 antibody reacts with human TWEAK Receptor/Fn14. Fn14 is distantly related to the TNFR family, containing one cysteine-rich domain in the extracellular region and a TNFR-associated factor binding domain but does not contain a death domain (DD) cytoplasmic region. Fn14 plays a role in TWEAK-induced endothelial cell migration, proliferation, and angiogenesis. TWEAK-induced cell death via Fn14 includes both apoptosis and necrosis and can be blocked by an anti-TWEAK antibody, CARL-1. Fn14 is expressed on HUVEC and in some cancer tissues but not on freshly isolated PBMCs. Fn14 mRNA expression has been identified during liver regeneration. It has been reported that ITEM4 cross-reacts with mouse Fn14.

As used herein, the term "local administration" means direct administration of a pharmaceutical at or to the vicinity of a site on or within an animal body, at which site a biological effect of the pharmaceutical is desired. Local administration excludes systemic routes of administration, such as intravenous or oral administration.

The term "liposome" is an artificially-prepared spherical vesicle composed of a lamellar phase lipid bilayer. The liposome can be used as a vehicle for administration of nutrients and pharmaceutical drugs. Liposomes can be prepared by disrupting biological membranes (such as by sonication). Liposomes are often composed of phosphatidylcholine-enriched phospholipids and may also contain mixed lipid chains with surfactant properties such as egg phosphatidylethanolamine. A liposome design may employ surface ligands for attaching to unhealthy tissue. The major types of liposomes are the multilamellar vesicle (MLV), the small unilamellar liposome vesicle (SUV), the large unilamellar vesicle (LUV), and the cochleate vesicle. In certain embodiments, anti-cancer drugs such as paclitaxel may be conjugated to a liposome or inserted into a liposome and delivered to glioma cells.

The term "nanoparticle" as used herein refers to particles with at least one dimension less than 100 nm or between 1 and 200 nanometers in size. In nanotechnology, a particle is defined as a small object that behaves as a whole unit with respect to its transport and properties. Particles are further classified according to diameter. Ultrafine particles are the same as nanoparticles and between 1 and 100 nanometers in size. Coarse particles cover a range between 2,500 and 10,000 nanometers. Fine particles are sized between 200 and 2,500 nanometers.

The term "non-immunogenic" as used herein refers to endogenous growth factor in its native state which normally elicits no, or only minimal levels of, circulating antibodies, T-cells, or reactive immune cells, and which normally does not elicit in the individual an immune response against itself.

The term "neurodegenerative disease" or "neurological disorder" as used herein, means a disease in which neurons of the CNS die or lose function or have physical degeneration including loss (death) of axons. Neurodegenerative diseases include PD, Alzheimer's disease, Huntington's disease and brain and spinal cord injuries that are associated with axon death.

The term "polymer," as used herein, is given its ordinary meaning as used in the art, i.e., a molecular structure comprising one or more repeat units (monomers), connected by covalent bonds. The repeat units may all be identical, or in some cases, there may be more than one type of repeat unit present within the polymer. In some cases, the polymer can be biologically derived, i.e., a biopolymer. Non-limiting examples include peptides or proteins. In some cases, additional moieties may also be present in the polymer, for example biological moieties such as those described below. If more than one type of repeat unit is present within the polymer, then the polymer is said to be a "copolymer."

The term "small molecule" refers to compounds, whether naturally-occurring or artificially created (e.g., via chemical synthesis) that have relatively low molecular weight and that are not proteins, polypeptides, or nucleic acids. Small molecules typically have multiple carbon-carbon bonds (i.e. organic compounds).

The terms "subject," "host," and "patient," as used herein, are used interchangeably and mean an animal being treated with the present compositions, including, but not limited to, simians, humans, avians, felines, canines, equines, rodents, bovines, porcines, ovines, caprines, mammalian farm animals, mammalian sport animals, and mammalian pets.

As used herein, the term "sustained release" as used herein refers to release of a substance over an extended period of time in contrast to a bolus type administration in which the entire amount of the substance is made biologically available at one time.

The term "targeting moiety" can be an antibody, which term is intended to include antibody fragments, characteristic portions of antibodies, single chain targeting moieties can be identified, e.g., using procedures such as phage display. Targeting moieties disclosed herein are typically conjugated to a disclosed polymer or copolymer (e.g. PLA-PEG), and such a polymer conjugate may form part of a disclosed nanoparticle.

As used herein, "therapeutically effective amount" means an amount sufficient to treat a subject afflicted with a disease (e.g., a neurodegenerative disease or neurological disorder or brain cancer) or to alleviate a symptom or a complication associated with the disease.

As used herein, "therapeutic agent" means a compound that has a beneficial and desirable effect when consumed or applied. In certain embodiments, therapeutic agents are chemotherapy medications used to attack cancers, e.g., glioblastomas. In other embodiments, therapeutic agents are anti-AD agents, anti-PD agents, anti-HD agents, anti-epilepsy agents), Some therapeutic agents are biological in origin, and can include components of plants and minerals as well as animal products. Others are synthetic, produced in a lab environment.

The term "treating" as used herein, means slowing, stopping or reversing the progression of a disease, particularly a neurodegenerative disease. As used herein, the terms "treatment," "treating," and the like, as used herein refer to obtaining a desired pharmacologic and/or physiologic effect. The effect may be prophylactic in terms of completely or partially preventing a condition or disease or symptom thereof and/or may be therapeutic in terms of a partial or complete cure for a condition or disease and/or adverse effect attributable to the condition or disease. "Treatment," includes any treatment of a condition or disease in a mammal, particularly in a human, and includes: (a) preventing the condition or disease or symptom thereof from occurring in a subject which may be predisposed to the condition or disease but has not yet been diagnosed as having it; (b) inhibiting the condition or disease or symptom thereof, such as, arresting its development; and (c) relieving, alleviating or ameliorating the condition or disease or symptom thereof, such as, for example, causing regression of the condition or disease or symptom thereof.

2. Overview

A targeted structure-specific particulate-based delivery system in certain embodiments comprises a nanoparticle, having a hydrodynamic diameter between 4 nm and 200 nm. The nanoparticle is coated with a polyethylene glycol (PEG) polymer coating on the surface of the nanoparticle having a surface density of at least 0.1 PEG molecules per nm$^2$ and configured to avoid non-specific binding to extracellular matrix and penetrate the extracellular matrix. A targeting moiety is conjugated on a surface of the nanoparticle and configured to promote specific binding to a cell surface molecule expressed by a target cell such as a brain tumor cell. Finally, a biologically active agent, such as therapeutic agents (anti-cancer agents), diagnostic agents (e.g. contrast agents; radionuclides; and fluorescent, luminescent, and magnetic moieties), prophylactic agents (e.g. vaccines), nutraceutical agents (e.g. vitamins, minerals, etc.), nucleic acids (e.g. DNA and RNA), and imaging agents (e.g., magnetic resonance imaging, optical imaging, positron emission tomography, X-ray computed tomography, and ultrasound imaging) is in or on the nanoparticle, wherein the biologically active agent is selected to enhance a desired response in the target cell either intracellularly or extracellulary.

3. Background

Brain Diseases and Disorders and Neurodegenerative Diseases a. Glioblastoma

GBMs are tumors that arise from astrocytes—the star-shaped cells that make up the "glue-like," or supportive tissue of the brain. These tumors are usually highly malignant (cancerous) because the cells reproduce quickly and they are supported by a large network of blood vessels. Glioblastomas are generally found in the cerebral hemispheres of the brain, but can be found anywhere in the brain or spinal cord. Glioblastomas usually contain a mix of cell types. It is not unusual for these tumors to contain cystic mineral, calcium deposits, blood vessels, or a mixed grade of cells. Glioblastomas are usually highly malignant—a large number of tumor cells are reproducing at any given time, and they are nourished by an ample blood supply. Dead cells may also be seen, especially toward the center of the tumor. Because these tumors come from normal brain cells, it is easy for them to invade and live within normal brain tissue. However, glioblastoma rarely spreads elsewhere in the body.

There are two types of glioblastomas: primary or de novo: Primary: These tumors tend to form and make their presence known quickly. This is the most common form of glioblastoma; it is very aggressive. Secondary: These tumors have a longer, somewhat slower growth history, but still are very aggressive. They may begin as lower-grade tumors which eventually become higher grade. They tend to be found in people 45 and younger, and represent about 10% of glioblastomas. Because glioblastomas can grow rapidly, the most common symptoms are usually caused by increased pressure in the brain. These symptoms can include headache, nausea, vomiting, and drowsiness. Depending on the location of the tumor, patients can develop a variety of other symptoms such as weakness on one side of the body, memory and/or speech difficulties, and visual changes. This tumor represents about 17% of all primary brain tumors and about 60-75% of all astrocytomas. They increase in frequency with age, and affect more men than women. Only three percent of childhood brain tumors are glioblastomas. Like many tumor types, the exact cause of glioblastoma is not known.

Glioblastoma can be difficult to treat because the tumors contain so many different types of cells. Some cells may respond well to certain therapies, while others may not be affected at all. This is why the treatment plan for glioblastoma may combine several approaches. The first step in treating glioblastoma is a procedure to make a diagnosis, relieve pressure on the brain, and safely remove as much tumor as possible through surgery. Because glioblastomas have finger-like tentacles, they are very difficult to completely remove. This is particularly true when they are growing near the parts of the brain that control important functions such as language and coordination. Radiation and chemotherapy may be used to slow the growth of tumors that cannot be removed with surgery. Chemotherapy may also be used to delay the need for radiation in young children.

Prognosis is usually reported in years of "median survival." Median survival is the time at which an equal number of patients do better and an equal number of patients do worse. With standard treatment, median survival for adults with an anaplastic astrocytoma is about two to three years. For adults with more aggressive glioblastoma, treated with concurrent temozolamide and radiation therapy, median survival is about 14.6 months and two-year survival is 30%. However, a 2009 study reported that almost 10% of patients with glioblastoma may live five years or longer. Children with high-grade tumors (grades III and IV) tend to do better than adults; five-year survival for children is about 25%. In addition, glioblastoma patients who have had their MGMT gene shut off by a process called methylation also have prolonged survival rates. The MGMT gene is thought to be a significant predictor of response. However, not all glioblastomas have the same biologic abnormalities. This may be the reason different patients respond differently to the same treatment and why different patients with the same tumor have different outcomes. Researchers continue to study the common characteristics of long-term brain tumor survivors, and how personalized and targeted treatments may be optimally used to treat brain tumor patients.

b. Parkinson's Disease

Parkinson's Disease (PD) is a neurodegenerative movement disorder, second only to Alzheimer's disease (AD) in prevalence (about 350 per 100,000 populations.) It is clinically characterized by rigidity, slowness of movement, and tremor. Most cases of Parkinson's disease are sporadic, but both sporadic and familial forms of the disease are characterized by intracellular Lewy bodies in dying neurons of the SN, a population of midbrain neurons (~60,000) that are selectively decimated in PD. Lewy bodies are predominantly composed of alpha-synuclein. Mutations in, and duplication of, the gene encoding alpha-synuclein have been found in patients with familial Parkinson's disease. Another gene associated with autosomal recessive PD is parkin. Diffuse cortical Lewy bodies composed of alpha-synuclein are observed in Lewy body disease (LBD), a dementing syndrome associated with parkinsonian tone changes, hallucinations, and rapid symptom fluctuation. LBD may be the second most common form of neurodegenerative dementia after AD, accounting for 20 to 30 percent of cases among persons over the age of 60 years. Similar to the vaccine approach to Alzheimer's disease promising results in a mouse model of Parkinson's/Lewy body disease have been obtained by immunization with alpha synuclein. Other dementing syndromes include fronto-termporal dementias, Pick's disease, and corticobasal dementia, and others known to neurological medicine.

c. Alzheimer's Disease

Alzheimer's Disease (AD) is a common dementing disordered memory and cognition neurodegenerative disease associated with brain accumulation of extracellular plaques composed predominantly of the Aβ(1-40), Aβ (1-42) and Aβ(1-43) peptides, all of which are proteolytic products of APP. In addition, neurofibrillary tangles, composed principally of abnormally phosphorylated tau protein (a neuronal microtubule-associated protein), accumulate intracellularly in dying neurons. Alzheimer's disease is marked by neuron and axon degeneration. [5]. Familial forms of AD can be caused by mutations in the APP gene, or in the presenilin 1 or 2 genes, the protein products of which are implicated in the processing of APP to Aβ. Apolipoprotein E allelic variants also influence the age at onset of both sporadic and familial forms of AD. AP, tau and phosphorylated tau has been detected in the blood and CSF of AD patients and in normal controls. Immunization of Alzheimer's disease patients with Aβ has shown some promising preliminary treatment results, although limited by autoimmune meningoencephalitis in humans.

d. Huntington's Disease

Huntington's disease (HD) is an autosomal dominant, inherited, neuropsychiatric disease which gives rise to progressive motor, cognitive and behavioral symptoms. The course of Huntington's is characterized by jerking uncontrollable movement of the limbs, trunk, and face (chorea); progressive loss of mental abilities; and the development of psychiatric problems. Huntington's disease progresses without remission over 10 to 15 years and usually appears in middle age (30-50 years). Juvenile HD (also called Westphal variant or akinetic-rigid HD) develops before the age of 20, progresses rapidly, and produces muscle rigidity in which the patient moves little, if at all (akinesia). It is estimated that one in every 10,000 persons—nearly 30,000 in the United States—has Huntington's disease. Juvenile Huntington's occurs in approximately 16% of all cases. Its core pathology involves degeneration of the basal ganglia, in particular, the caudate and putamen, and is caused by an unstable expansion of the trinucleotide CAG, coding for glutamine, in a single autosomal gene IT-15 on chromosome 4, coding for a mutated form of the protein, huntingtin. How the mutation of gene IT-15 alters the function of the protein is not well understood. In Huntington's disease, synapse dysfunction is the earliest observable event, closely followed by axon degeneration often without signs of neuron loss in animal models. [6].

Treatment of Huntington's disease focuses on reducing symptoms, preventing complications, and providing support and assistance to the patient. There are several substances available today for the treatment of chorea. Other neurological symptoms, such as dystonia, can be treated, but treatment is associated with a high risk of adverse events. Psychiatric symptoms, on the other hand, are often amenable to treatment and relief of these symptoms may provide significant improvement in quality of life. [7]. Most drugs used to treat the symptoms of HD have side effects such as fatigue, restlessness, or hyperexcitability. Cystamine (Decarboxycystine) alleviates tremors and prolongs life in mice with the gene mutation for Huntington's disease (HD). The drug appears to work by increasing the activity of proteins that protect nerve cells, or neurons, from degeneration. The study suggests that a similar treatment may one day be useful in humans with HD and related disorders. [8].

In the present specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. The contents of all references, pending patent applications and published patents, cited throughout this application are hereby expressly incorporated by reference as if set forth herein in their entirety, except where terminology is not consistent with the definitions herein. Although specific terms are employed, they are used as in the art unless otherwise indicated.

e. Epilepsy

A seizure is a paroxysmal event due to abnormal, excessive, hypersynchronous discharges from an aggregate of central nervous system neurons. Epilepsy describes a condition in which a person has recurrent seizures due to a chronic, underlying process. Among the many causes of epilepsy there are various epilepsy syndromes in which the clinical and pathologic characteristics are distinctive and suggest a specific underlying etiology. The prevalence of epilepsy has been estimated at 5 to 10 people per 1000 population. Severe, penetrating head trauma is associated with up to a 50% risk of leading to epilepsy. Other causes of epilepsy include stroke, infection and genetic susceptibility. Antiepileptic drug therapy is the mainstay of treatment for most patients with epilepsy and a variety of drugs have been used. [9].

Twenty percent of patients with epilepsy are resistant to drug therapy despite efforts to find an effective combination of antiepileptic drugs. Surgery can then be an option. Video-EEC monitoring can be used to define the anatomic location of the seizure focus and to correlate the abnormal electrophysiologic activity with behavioral manifestations of the seizure. Routine scalp or scalp-sphenoidal recordings are usually sufficient for localization. A high resolution MRI scan is routinely used to identify structural lesions. Functional Imaging studies such as SPECT and PET are adjunctive tests that can help verify the localization of an apparent epileptogenic region with an anatomic abnormality. Once the presumed location of the seizure onset is identified, additional studies, including neuropsychological testing and the intracarotid amobarbital test (Wada's test) can be used to assess language and memory localization and to determine the possible functional consequences of surgical removal of the epileptogenic region.

In some cases, the exact extent of the resection to be undertaken can be determined by performing cortical mapping at the time of the surgical procedure. This involves electrophysiologic recordings and cortical stimulation of the awake patient to identify the extent of epileptiform disturbances and the function of the cortical regions in questions. The most common surgical procedure for patients with temporal lobe epilepsy involves resection of the anteromedial temporal lobe (temporal lobectomy) or a more limited removal of the underlying hippocampus and amygdala. Focal seizures arising from extratemporal regions may be suppressed by a focal neocortical resection. Unfortunately, about 5% of patients can still develop clinically significant complications from surgery and about 30% of patients treated with temporal lobectomy will still have seizures. Focal epilepsy can involve almost any part of the brain and usually results from a localized lesion of functional abnormality. One type of focal epilepsy is the psychomotor seizure. Current therapy includes use of an EEG to localize abnormal spiking waves originating in areas of organic brain disease that predispose to focal epileptic attacks, followed by surgical excision of the focus to prevent future attacks.

f. Other Cancers

Fn14 receptor overexpression has been detected in many types of solid tumors (bladder, brain, breast, cervical, colorectal, esophageal, liver, lung, skin, ovarian, pancreatic, prostate, renal, testicular) and in tumor metastases (bone, liver, brain lymph node). For example, Feng et al. [45] used Northern blot analysis to compare Fn14 mRNA levels in HCC tumor tissue versus adjacent non-tumoral liver tissue and found elevated levels of Fn14 gene expression in three of the four tumor specimens examined. These investigators also detected Fn14 mRNA induction in two transgenic mouse models of hepatocarcinogenesis. In another study, Michaelson et al. [46] examined Fn14 gene expression in normal breast tissue and primary breast tumor samples using two experimental approaches: in situ hybridization and immunohistochemistry. Fn14 mRNA expression was detected in $9/10$ normal tissue specimens and $35/60$ breast tumor specimens using the first approach and, in a different set of samples, Fn14 protein expression was detected in $1/10$ normal tissue specimens and $10/19$ breast tumor specimens using the second approach.

4. Embodiments

In certain embodiments, relatively free movement of nanoparticles within brain tissue through minimal nonspecific binding and consideration of size-related steric restrictions has been accomplished through the utilization of a targeted structure-specific particulate-based delivery system. Specifically, in certain embodiments, this enhanced diffusivity permitted the development of a selective targeting strategy to model particulate drug carriers to experimental xenograft tumors within the brain. When administered intracranially, in certain embodiments, ~100 nm PEG-coated, Fn14-targeted nanoparticles (CNP-ITEM4) showed broad distribution in the brain and selective targeting to the Fn14-positive tumor cells in mice bearing human U87 tumor xenografts. Tumor cells located at distant sites, deep within the brain, likely contribute to tumor recurrence since they cannot be removed with surgery and are the most difficult to treat due to the close proximity of functioning brain cells and the intact BBB. Therefore, reducing the non-specific binding towards the brain ECM is a critical rate-limiting step in the development of effective targeted treatments. Tumor specific targeting of nanoparticles can be enhanced through a balance of (i) minimal non-specific binding to provide broad particle dispersion and (ii) selective binding to distant glioma cells via Fn14, a cell surface molecule expressed by these cells.

Fn14, the smallest member of the TNFR superfamily, is an emerging molecular target for GBM therapy [10-11]. Fn14 is minimally expressed in normal human brain, but highly expressed in malignant gliomas with more aggressive and invasive characteristics [12]. Importantly, elevated Fn14 mRNA and protein expression has been detected in the rim of invading glioma cells with less elevation in the tumor core, which provides the opportunity to target the invasive cells with Fn14-directed therapeutics [12-13]. The Fn14-specific monoclonal antibody ITEM4 was used as the targeting moiety in our initial studies. This targeting molecule was chosen based on previous studies revealing that Fn14-positive cancer cells are vulnerable to ITEM4-based immunotoxins [14-16]. Although monoclonal antibodies introduce some inherent limitations; specifically, their relatively large size and the presence of the Fc region may contribute to off-target effects (e.g. cell binding, recognition, and clearance), the highly specific binding of a full monoclonal antibody enabled an important proof-of-concept determination in this study.

Current therapies and clinical trials using non-targeted and targeted therapeutic strategies for GBM have been affected by limited distribution within the brain. For example, carmustine was shown to diffuse a few millimeters from the implantable Gliadel polymer wafer surface during the majority of the release phase in vivo [17]. In addition, recent clinical trials have shown that CED of targeted toxins, such as IL-13-, IL-4-, and transferrin-conjugated toxins, as well as viral particles, failed to show survival improvements. This is most likely because penetration and distribution of the therapeutic agent is still limited [17, 18]. In other examples, Voges et al. and Zhou et al. showed that even following CED, the ECM acts as a diffusion barrier limiting the spatial distribution of therapeutic nanoparticles [19-21,]. Therefore, the diffusion and distribution of therapeutics within the brain and brain tumors is a major limitation to achieving significant treatment efficacy, even with these local therapeutic approaches. This is thought to be especially important for GBM given the invasive, migratory nature of the disease [22].

Recent studies suggest targeted nanoparticle therapies offer the potential of delivering agents directly to invading tumor cells to improve treatment efficacy while minimizing associated toxicities [23]. In one example, chlorotoxin conjugated chitosan-based nanoparticles showed preferential accumulation in gliomas in mice [24]. In other study, liposomes conjugated with IL-13 were able to deliver doxorubicin specifically to glioma cells [25]. However, achieving broad particle distribution and therapeutically relevant nanoparticle targeting remain a challenge. Nanoparticle diffusion in the brain predominantly takes place through narrow tortuous spaces between cells [26-27]. The ECM, the main component of the extracellular space, imposes an adhesive and steric barrier to the diffusion of nanoparticles through the brain parenchyma, as shown with the uncoated 100 nm nanoparticles (UNP) in this study. Vargova and colleagues also found that the ECS volume fraction and tortuosity increase with glioma histopathological grade, further increasing the diffusion barriers for small molecules and nanoparticles [28]. Hence, limited penetration of targeted therapeutic nanoparticles in the ECS remains a key hurdle to (i) effective drug distribution within brain tumor-affected regions, and (ii) targeting to tumor-related structures where moving through brain tissue and only attaching to specific structures may improve efficacy and reduce toxicity.

In certain embodiments, it is possible to minimize the non-specific binding to the brain ECM in the design of a targeted brain tissue penetrating nanoparticle system, which then permitted selective tumor cell targeting through minimal off-target binding. The demonstration here of enhanced particle distribution and tumor targeting suggests a promising opportunity for the development of new formulation strategies for brain and other cancers. Based on the formulation characteristics developed here in model polystyrene nanoparticles, we envision drug delivery platforms that can be readily translated into new therapeutic systems, such as biodegradable PLGA nanoparticles. A similar strategy can be adapted to a variety of different FDA-approved polymers, drugs, gene constructs, and targeting ligands. These results support further investigation into the use of the Fn14-targeted nanoparticle platform with CED and other novel delivery approaches for GBM to potentially improve the distribution and duration of therapeutic effects. Fn14 is also overexpressed in a broad range of other cancers outside the brain [10-12] including melanoma [14], breast [29], prostate [30], and non-small cell lung cancer [31]. Accordingly, an Fn14-targeted nanoparticle platform may have broader applicability beyond GBM patient therapy in the future.

Polymers

In some embodiments, the nanoparticles of the invention comprise a matrix of polymers and a biologically active agent. In some embodiments, a biologically active agent and/or targeting moiety can be associated with at least part of the polymeric matrix. For example, in some embodiments, a targeting moiety (e.g. an antibody or ligand) can be covalently associated with the surface of a polymeric matrix. In some embodiments, covalent association is mediated by a linker. The biologically active agent can be associated with the surface of, encapsulated within, surrounded by, and/or dispersed throughout the polymeric matrix.

A wide variety of polymers and methods for forming particles therefrom are known in the art of drug delivery. In some embodiments, the disclosure is directed toward nanoparticles with at least two macromolecules, wherein the first macromolecule comprises a first polymer bound to a low-molecular weight ligand (e.g. targeting moiety); and the second macromolecule comprising a second polymer that is not bound to a targeting moiety. The nanoparticle can optionally include one or more additional, unfunctionalized, polymers.

Any polymer can be used in accordance with the present invention. Polymers can be natural or unnatural (synthetic) polymers. Polymers can be homopolymers or copolymers comprising two or more monomers. In terms of sequence, copolymers can be random, block, or comprise a combination of random and block sequences. Typically, polymers in accordance with the present invention are organic polymers. Non-limiting examples include peptides or proteins. In some cases, additional moieties may also be present in the polymer, for example biological moieties such as those described below.

It is to be understood that in any embodiment employing a polymer, the polymer being employed may be a copolymer in some cases. The repeat units forming the copolymer may be arranged in any fashion. For example, the repeat units may be arranged in a random order, in an alternating order, or as a block copolymer, i.e., comprising one or more regions each comprising a first repeat unit (e.g., a first block), and one or more regions each comprising a second repeat unit (e.g., a second block), etc. Block copolymers may have two (a diblock copolymer), three (a triblock copolymer), or more numbers of distinct blocks.

Disclosed particles can include copolymers, which, in some embodiments, describes two or more polymers (such as those described herein) that have been associated with each other, usually by covalent bonding of the two or more polymers together. Thus, a copolymer may comprise a first polymer and a second polymer, which have been conjugated together to form a block copolymer where the first polymer can be a first block of the block copolymer and the second polymer can be a second block of the block copolymer. Of course, those of ordinary skill in the art will understand that a block copolymer may, in some cases, contain multiple blocks of polymer, and that a "block copolymer," as used herein, is not limited to only block copolymers having only a single first block and a single second block. For instance, a block copolymer may comprise a first block comprising a first polymer, a second block comprising a second polymer, and a third block comprising a third polymer or the first polymer, etc. In some cases, block copolymers can contain any number of first blocks of a first polymer and second blocks of a second polymer (and in certain cases, third blocks, fourth blocks, etc.). In addition, it should be noted that block copolymers can also be formed, in some instances, from other block copolymers. For example, a first block copolymer may be conjugated to another polymer (which may be a homopolymer, a biopolymer, another block copolymer, etc.), to form a new block copolymer containing multiple types of blocks, and/or to other moieties (e.g., to non-polymeric moieties).

In some embodiments, the polymer (e.g., copolymer, e.g., block copolymer) can be amphiphilic, i.e., having a hydrophilic portion and a hydrophobic portion, or a relatively hydrophilic portion and a relatively hydrophobic portion. A hydrophilic polymer can be one generally that attracts water and a hydrophobic polymer can be one that generally repels water. A hydrophilic or a hydrophobic polymer can be identified, for example, by preparing a sample of the polymer and measuring its contact angle with water. In some cases, the hydrophilicity of two or more polymers may be measured relative to each other, i.e., a first polymer may be more hydrophilic than a second polymer. For instance, the first polymer may have a smaller contact angle than the second polymer.

In one set of embodiments, a polymer (e.g., copolymer, e.g., block copolymer) contemplated herein includes a biocompatible polymer, i.e., the polymer that does not typically induce an adverse response when inserted or injected into a living subject, for example, without significant inflammation and/or acute rejection of the polymer by the immune system, for instance, via a T-cell response. Accordingly, the therapeutic particles contemplated herein can be non-immunogenic. Biocompatibility typically refers to the acute rejection of material by at least a portion of the immune system, i.e., a nonbiocompatible material implanted into a subject provokes an immune response in the subject that can be severe enough such that the rejection of the material by the immune system cannot be adequately controlled, and often is of a degree such that the material must be removed from the subject. One simple test to determine biocompatibility can be to expose a polymer to cells in vitro; biocompatible polymers are polymers that typically will not result in significant cell death at moderate concentrations, e.g., at concentrations of 50 micrograms/$10^6$ cells. For instance, a biocompatible polymer may cause less than about 20% cell death when exposed to cells such as fibroblasts or epithelial cells, even if phagocytosed or otherwise uptaken by such cells. Non-limiting examples of biocompatible polymers that may be useful in various embodiments of the present invention include polydioxanone (PDO), polyhydroxyalkanoate, polyhydroxybutyrate, poly(glycerol sebacate), polyglycolide, polylactide, PLGA, polycaprolactone, or copolymers or derivatives including these and/or other polymers. In certain embodiments, the biodegradable polymer is selected from the group consisting of: PLGA, PLA, PCL, chitosan, gelatin, albumin, and PAC.

In certain embodiments, contemplated biocompatible polymers may be biodegradable, i.e., the polymer is able to degrade, chemically and/or biologically, within a physiological environment, such as within the body. In one embodiment, the biodegradable polymer and their degradation byproducts can be biocompatible. For instance, a contemplated polymer may be one that hydrolyzes spontaneously upon exposure to water (e.g., within a subject), the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer can be degraded into monomers and/or other non-polymeric moieties) may be on the order of days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEGylated polymers and copolymers of lactide and glycolide (e.g., PEGylated PLA, PEGylated PGA, PEGylated PLGA, and derivatives thereof. In some embodiments, polyesters include, for example, polyanhydrides, poly(ortho ester) PEGylated poly(ortho ester), poly(caprolactone), PEGylated poly(caprolactone), polylysine, PEGylated polylysine, poly(ethylene imine), PEGylated poly(ethylene imine), poly(L-lactide-co-L-lysine), poly(serine ester), poly(4-hydroxy-L-proline ester), poly[.alpha.-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA can be characterized by the ratio of lactic acid:glycolic acid. Lactic acid can be L-lactic acid, D-lactic acid, or D,L-lactic acid. The degradation rate of PLGA can be adjusted by altering the lactic acid-glycolic acid ratio. In some embodiments, PLGA to be used in accordance with the present invention can be characterized by a lactic acid:glycolic acid ratio of approximately 85:15, approximately 75:25, approximately 60:40, approximately 50:50, approximately 40:60, approximately 25:75, or approximately 15:85. In some embodiments, the ratio of lactic acid to glycolic acid monomers in the polymer of the particle (e.g., the PLGA block copolymer or PLGAPEG block copolymer), may be selected to optimize for various parameters such as water uptake, biologically active agent release and/or polymer degradation kinetics can be optimized.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), methacrylic acid alkylamide copolymer, poly(methyl methacrylate), poly(methacrylic acid polyacrylamide, amino alkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g. DNA, RNA, or derivatives thereof). Amine-containing polymers such as poly(lysine), polyethylene imine (PEI), and poly(amidoamine) dendrimers are contemplated for use, in some embodiments, in a disclosed particle.

In some embodiments, polymers can be degradable polyesters bearing cationic side chains. Examples of these polyesters include poly(L-lactide-co-L-lysine), poly(serine ester), poly(4-hydroxy-L-proline ester). Particles disclosed herein may or may not contain PEG. In addition, certain embodiments can be directed towards copolymers containing poly(ester-ether)s, e.g., polymers having repeat units joined by ester bonds (e.g., R—C(O)—O—R' bonds) and ether bonds (e.g., R—O—R' bonds). In some embodiments of the invention, a biodegradable polymer, such as a hydrolyzable polymer, containing carboxylic acid groups, may be conjugated with poly(ethylene glycol) repeat units to form a poly(ester-ether). A polymer (e.g., copolymer, e.g., block copolymer) containing poly(ethylene glycol) repeat units can also be referred to as a "PEGylated" polymer. It is contemplated that PEG may be terminated and include an end group, for example, when PEG is not conjugated to a ligand. For example, PEG may terminate in a hydroxyl, a methoxy or other alkoxyl group, a methyl or other alkyl group, an aryl group, a carboxylic acid, an amine, an amide, an acetyl group, a guanidino group, or an imidazole. Other contemplated end groups include azide, alkyne, maleimide, aldehyde, hydrazide, hydroxylamine, alkoxyamine, or thiol moieties. Those of ordinary skill in the art will know of methods and techniques for PEGylating a polymer, for example, by using EDC (1-ethyl-3-(3-dimethylaminopropyl) carbodiimide hydrochloride) and NHS (N-hydroxysuccinimide) to react a polymer to a PEG group terminating in an amine, by ring opening polymerization techniques (ROMP), or the like.

In one embodiment, the molecular weight of the polymers can be optimized for effective treatment as disclosed herein. For example, the molecular weight of a polymer may influence particle degradation rate (such as when the molecular weight of a biodegradable polymer can be adjusted), solubility, water uptake, and drug release kinetics. For example, the molecular weight of the polymer can be adjusted such that the particle biodegrades in the subject being treated within a reasonable period of time (ranging from a few hours to 1-2 weeks, 3-4 weeks, 5-6 weeks, 7-8 weeks, etc.). A disclosed particle can for example comprise a diblock copolymer of PEG and PL(G)A, wherein for example, the PEG portion may have a number average molecular weight of about 1,000-20,000, e.g., about 2,000-20,000, e.g., about 2 to about 10,000, and the PL(G)A portion may have a number average molecular weight of about 5,000 to about 20,000, or about 5,000-100,000, e.g., about 20,000-70,000, e.g., about 15,000-50,000. An exemplary therapeutic nanoparticle may includes about 10 to about 99 weight percent poly(lactic) acid-poly(ethylene) glycol copolymer or poly(lactic)-co-poly(glycolic) acid-poly(ethylene)glycol copolymer, or about 20 to about 80 weight percent, about 40 to about 80 weight percent, or about 30 to about 50 weight percent, or about 70 to about 90 weight percent poly(lactic) acid-poly(ethylene)glycol copolymer or poly(lactic)-copoly(glycolic) acid-poly(ethylene) glycol copolymer. Exemplary poly(lactic) acid-poly(ethylene)glycol copolymers can include a number average molecular weight of about 2 to about 200 kDa of poly(lactic) acid and a number average molecular weight of about 2 kDa to about 10 kDa of poly(ethylene)glycol.

Disclosed nanoparticles may optionally include about 1 to about 50 weight percent poly(lactic) acid or poly(lactic) acidco-poly(glycolic) acid (which does not include PEG), or may optionally include about 1 to about 50 weight percent, or about 10 to about 50 weight percent or about 30 to about 50 weight percent poly(lactic) acid or poly(lactic) acidcopoly(glycolic) acid. For example, poly(lactic) or poly (lactic)-co-poly(glycolic) acid may have a number average molecule weight of about 5 to about 15 kDa, or about 5 to about 12 kDa. Exemplary PLA may have a number average molecular weight of about 5 to about 10 kDa. Exemplary PLGA may have a number average molecular weight of about 8 to about 12 kDa.

In certain embodiments, the polymers of the nanoparticles can be conjugated to a lipid. The polymer can be, for example, a lipid-terminated PEG. As described below, the lipid portion of the polymer can be used for self assembly with another polymer, facilitating the formation of a nanoparticle. For example, a hydrophilic polymer could be conjugated to a lipid that will self assemble with a hydrophobic polymer.

In some embodiments, lipids are oils. In general, any oil known in the art can be conjugated to the polymers used in the invention. In some embodiments, an oil can comprise one or more fatty acid groups or salts thereof. In some embodiments, a fatty acid group can comprise digestible, long chain (e.g., $C_8$-$C_{50}$), substituted or unsubstituted hydrocarbons. In some embodiments, a fatty acid group can be a $C_{10}$-$C_{20}$ fatty acid or salt thereof. In some embodiments, a fatty acid group can be a $C_{15}$-$C_{20}$ fatty acid or salt thereof. In some embodiments, a fatty acid can be unsaturated. In some embodiments, a fatty acid group can be monounsaturated. In some embodiments, a fatty acid group can be polyunsaturated. In some embodiments, a double bond of an unsaturated fatty acid group can be in the cis conformation. In some embodiments, a double bond of an unsaturated fatty acid can be in the trans conformation.

In some embodiments, a fatty acid group can be one or more of butyric, caproic, caprylic, capric, lauric, myristic, palmitic, stearic, arachidic, behenic, or lignoceric acid. In some embodiments, a fatty acid group can be one or more of palmitoleic, oleic, vaccenic, linoleic, alpha-linolenic, gamma-linoleic, arachidonic, gadoleic, arachidonic, eicosapentaenoic, docosahexaenoic, or erucic acid.

Targeting Moieties

Provided herein are targeted structure-specific particulate-based delivery systems comprising nanoparticles that may include an optional targeting moiety, i.e., a moiety able to bind to or otherwise associate with a biological entity, for example, a membrane component, a cell surface receptor, prostate specific membrane antigen, or the like. A targeting moiety present on the surface of the nanoparticle may allow the nanoparticle to become localized at a particular targeting site, for instance, a tumor, a disease site, a tissue, an organ, a type of cell, etc. As such, the nanoparticle may then be "target specific." The drug or other payload or gene construct may then, in some cases, be released from the particle and allowed to interact locally with the particular targeting site.

In one set of embodiments, a targeting portion may cause the nanoparticles to become localized to a tumor (e.g. a solid tumor) a disease site, a tissue, an organ, a type of cell, etc. within the body of a subject, depending on the targeting moiety used. For example, a Fn14 monoclonal antibody may become localized to a Fn14 cell surface receptor on a solid tumor, e.g. glioblastoma tumor or glioblastoma cancer cells. The subject may be a human or non-human animal. Examples of subjects include, but are not limited to, a mammal such as a dog, a cat, a horse, a donkey, a rabbit, a cow, a pig, a sheep, a goat, a rat, a mouse, a guinea pig, a hamster, a primate, a human or the like.

Small Molecules

Contemplated targeting moieties include small molecules. Small molecules typically have multiple carbon-carbon bonds. In certain embodiments, small molecules are less than about 2000 g/mol in size. In some embodiments, small molecules are less than about 1500 g/mol or less than about 1000 g/mol. In some embodiments, small molecules are less than about 800 g/mol or less than about 500 g/mol, for example about 100 g/mol to about 600 g/mol, or about 200 g/mol to about 500 g/mol. In some embodiments, small molecule targeting moieties that may be used to target cells associated with glioblastoma tumors include thiol and indole thiol derivatives, such as 2-MPPA and 3-(2-mercaptoethyl)-1H-indole-2-carboxylic acid derivatives. In some embodiments, For example, contemplated the targeting moieties may include a nucleic acid, polypeptide, glycoprotein, carbohydrate, or lipid. For example, a targeting moiety can be a nucleic acid targeting moiety (e.g. an aptamer, e.g., the A10 aptamer) that binds to a cell type specific marker. In general, an aptamer is an oligonucleotide (e.g., DNA, RNA, or an analog or derivative thereof) that binds to a particular target, such as a polypeptide.

Receptor Ligands

In some embodiments, a targeting moiety may be a naturally occurring or synthetic ligand for a cell surface receptor, e.g., a growth factor, cytokine, hormone, LDL, transferrin, etc. See also, Zhou, H., Mohamedali, K. A., Gonzalez-Angulo, A. M., Cao, Y., Migliorini, M., Cheung, L. H., LoBello, J., Lei, X., Qi, Y., Hittelman, W. N., Winkles, J. A., Tran, N. L. and Rosenblum, M. G. (2014). Development of human serine protease-based therapeutics targeting Fn14 and identification of Fn14 as a new target overexpressed in TNBC. *Molecular Cancer Therapeutics* 13:2688-2705 (where the Fn14 ligand TWEAK is used to target a cytotoxin to Fn14-positive breast tumors).

Antibodies

A targeting moiety can be an antibody, which term is intended to include antibody fragments, characteristic portions of antibodies, single chain targeting moieties can be identified, e.g., using procedures such as phage display. In one embodiment, a disclosed nanoparticle includes a targeting moiety that is a Fn14 monoclonal antibody, ITEM4, ITEM4-SH, ITEM4-scFv, or ITEM4 Fab. Other antibodies are contemplated that are available commercially (e.g., ITEM1) to target Fn14-positive tumors as described in Johnston, A. J., et al., "Targeting of Fn14 Prevents Cancer-Induced Cachexia and Prolongs Survival." *Cell.* 2015 Sep. 10; 162(6):1365-78.

The amino acids of an anti-Fn14 antibody or antigen-binding fragment thereof that interact with the Fn14 protein are preferably not mutated (or, if mutated, replaced by a conserved amino acid residue). In one embodiment of a variant of the ITEM4 antibody or a variant of a ITEM4 antibody is not changed.

In one embodiment, the antibody or antigen-binding fragment does not cross-react with other TNF and TNFR family members. An antibody or antigen-binding fragment described herein can be, for example, a humanized antibody, a fully human antibody, a monoclonal antibody, a single chain antibody, a monovalent antibody, a polyclonal antibody, a chimeric antibody, a multispecific antibody (e.g., a bispecific antibody), a multivalent antibody, an F^ fragment, an F(^)$_2$ fragment, an F$_{ab}$' fragment, an F$_{sc}$ fragment, or an F$_v$ fragment. An antibody or antigen-binding fragment described herein may be "multispecific," e.g., bispecific, trispecific or of greater multispecificity, meaning that it recognizes and binds to two or more different epitopes present on one or more different antigens (e.g., proteins) at the same time. Thus, whether a binding molecule is "monospecfic" or "multispecific," e.g., "bispecific," refers to the number of different epitopes with which the binding molecule reacts. Multispecific antibodies may be specific for different epitopes of an Fn14 protein, or may be specific for Fn14 as well as for a heterologous epitope, such as a heterologous polypeptide or solid support material.

As used herein the term "valent" (as used in "multivalent antibody") refers to the number of potential binding domains, e.g., antigen binding domains, present in a binding molecule. Each binding domain specifically binds one epitope. When a binding molecule comprises more than one binding domain, each binding domain may specifically bind the same epitope (for an antibody with two binding domains, termed "bivalent monospecific") or to different epitopes (for an antibody with two binding domains, termed "bivalent bispecific"). An antibody may also be bispecific and bivalent for each specificity (termed "bispecific tetravalent antibodies"). In another embodiment, tetravalent mmibodies or domain deleted antibodies can be made. Bispecific bivalent antibodies, and methods of making them, are described, for instance in U.S. Pat. Nos. 5,731,168; 5,807,706; 5,821,333; and U.S. Application Publication Nos. 2003/020734 and 2002/0155537, the disclosures of all of which are incorporated by reference herein. Bispecific tetravalent antibodies, and methods of making them are described, for instance, in WO 02/096948 and WO 00/44788, the disclosures of both of which are incorporated by reference herein. See generally, PCT publications WO 93/17715; WO 92/08802; WO 91/00360; WO 92/05793; WO 2007/109254; U.S. Pat. Nos. 4,474,893; 4,714,681; 4,925,648; 5,573,920; 5,601,819) These references are all incorporated by reference herein.

In certain embodiments, an anti-Fn14 antibody, e.g., one or the two heavy chains of the antibody, is linked to one or more scFv to form a bispecific antibody. In other embodiments, an anti-Fn14 antibody is in the form of an scFv that is linked to an antibody to form a bispecific molecule. Antibody-scFv constructs are described, e.g., in WO 2007/109254.

The heavy and light chains of the antibody can be substantially full-length. The protein can include at least one, and optionally two, complete heavy chains, and at least one, and optionally two, complete light chains or can include an antigen-binding fragment. In yet other embodiments, the antibody has a heavy chain constant region chosen from, e.g., IgG1, IgG2, IgG3, IgG4, IgM, IgA1, IgA2, IgD, and IgE. Typically, the heavy chain constant region is human or a modified form of a human constant region. In another embodiment, the antibody has a light chain constant region chosen from, e.g., kappa or lambda, particularly, kappa (e.g., human kappa).

In certain embodiments, the binding of antibodies or antigen binding fragments thereof results in cross-linking or clustering of the Fn14 receptor on the cell surface. For example, antibodies or antigen-binding fragments thereof may form a multimer, e.g., by binding to protein A, or may be multivalent. An antibody or antigen-binding fragment described herein can be modified to enhance effector function, e.g., so as to enhance antigen-dependent cell-mediated cytotoxicity (ADCC) and/or complement dependent cytotoxicity (CDC) of the antibody or enhance cross-linking of the target receptor/Fn14. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). Homodimeric antibodies with enhanced anti-tumor activity may also be prepared using heterobifunctional cross-linkers as described in Wolff et al.

Cancer Research 53:2560-2565 (1993). Alternatively, an antibody can be engineered which has dual Fc regions and may thereby have enhanced complement lysis and ADCC capabilities. See Stevenson et al. Anti-Cancer Drug Design 3:219-230 (1989). In addition, an antibody can be defucosylated such that the modified antibody exhibits enhanced ADCC as compared to the non-defucosylated form of the antibody. See. e.g., WO2006089232.

This disclosure includes, but is not limited to specific examples of anti-Fn14 antibodies, such as ITEM4, ITEM4-SH, or ITEM4-scFv, or ITEM4 Fab. Particular antibodies, such as these, can be made, for example, by preparing and expressing synthetic genes that encode the recited amino acid sequences or by mutating human germline genes to provide a gene that encodes the recited amino acid sequences. Moreover, these antibodies and other anti-Fn14 antibodies (e.g., antibodies) can be produced, e.g., using one or more methods. Numerous methods are available for obtaining antibodies, particularly human antibodies. One exemplary method includes screening protein expression libraries, e.g., phage or ribosome display libraries. Phage display is described, for example, U.S. Pat. No. 5,223,409; Smith (1985) Science 228:1315-1317; WO 92/18619; WO 91/17271; WO 92/20791; WO 92/15679; WO 93/01288; WO 92/01047; WO 92/09690; and WO 90/02809. The display of Fab' s on phage is described, e.g., in U.S. Pat. Nos. 5,658,727; 5,667,988; and 5,885,793. In addition to the use of display libraries, other methods can be used to obtain a Fn14-binding antibody. For example, the Fn14 protein or a peptide thereof can be used as an antigen in a non-human animal, e.g., a rodent. e.g., a mouse, hamster, or rat. In addition, cells transfected with a cDNA encoding Fn14 can be injected into a non-human animal as a means of producing antibodies that effectively bind the cell surface FnI 4 protein.

In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See, e.g., XENOMOUSE™, Green et al. (1994) Nature Genetics 7:13-21, U.S. 2003-0070185. WO 96/34096, and WO 96/33735. In another embodiment, a monoclonal antibody is obtained from the non-human animal, and then modified, e.g., humanized or deimmunized. Winter describes an exemplary CDR-grafting method that may be used to prepare humanized antibodies described herein (U.S. Pat. No. 5,225,539). All or some of the CDRs of a particular human antibody may be replaced with at least a portion of a non-human antibody. It may only be necessary to replace the CDRs required for binding or binding determinants of such CDRs to arrive at a useful humanized antibody that binds to Fn14. Humanized antibodies can be generated by replacing sequences of the Fv variable region that are not directly involved in antigen binding with equivalent sequences from human Fv variable regions. General methods for generating humanized antibodies are provided by Morrison, S. L. (1985) Science 229:1202-1207, by Oi et al. (1986) BioTechniques 4:214, and by U.S. Pat. Nos. 5,585,089; 5,693,761; 5,693,762; 5,859,205; and 6,407,213. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a predetermined target, as described above, from germline immunoglobulin genes, or from synthetic constructs. The recombinant DNA encoding the humanized antibody can then be cloned into an appropriate expression vector.

Human germline sequences, for example, are disclosed in Tomlinson, L A. et al. (1992) J MoI. Biol. 227:776-798; Cook, G. P. et al. (1995) Immunol. Today 16: 237-242; Chothia, D. et al. (1992) J MoI. Bio. 227:799-817; and Tomlinson et al. (1995) EMBO J 14:4628-4638. The V BASE directory provides a comprehensive directory of human immunoglobulin variable region sequences (compiled by Tomlinson, L A. et al. MRC Centre for Protein Engineering, Cambridge, UK). These sequences can be used as a source of human sequence, e.g., for framework regions and CDRs. Consensus human framework regions can also be used, e.g., as described in U.S. Pat. No. 6,300,064.

A non-human Fn14-binding antibody may also be modified by specific deletion of human T cell epitopes or "deimmunization" by the methods disclosed in WO 98/52976 and WO 00/34317. Briefly, the heavy and light chain variable regions of an antibody can be analyzed for peptides that bind to MHC Class 11; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the $V_H$ and $V_L$ sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable regions, or preferably, by single amino acid substitutions. As far as possible, conservative substitutions are made. Often, but not exclusively, an amino acid common to a position in human germline antibody sequences may be used. After the deimmunizing changes are identified, nucleic acids encoding $V_H$ and VL can be constructed by mutagenesis or other synthetic methods (e.g., de novo synthesis, cassette replacement, and so forth). A mutagenized variable sequence can, optionally, be fused to a human constant region, e.g., human IgG1 or kappa constant regions.

Other methods for humanizing antibodies can also be used. For example, other methods can account for the three dimensional structure of the antibody, framework positions that are in three dimensional proximity to binding determinants, and immunogenic peptide sequences. See, e.g., WO 90/07861; U.S. Pat. Nos. 5,693,762; 5,693,761; 5,585,089; 5,530,101; and 6,407,213; Tempest et al. (1991) Biotechnology 9:266-271. Still another method is termed "humaneering" and is described, for example, in U.S. 2005-008625. The antibody can include a human Fc region, e.g., a wild-type Fc region or an Fc region that includes one or more alterations. In one embodiment, the constant region is altered, e.g., mutated, to modify the properties of the antibody (e.g., to increase or decrease one or more of: Fc receptor binding, antibody glycosylation, the number of cysteine residues, effector cell function, or complement function). For example, the human IgG1 constant region can be mutated at one or more residues, e.g., one or more of residues 234 and 237. Antibodies may have mutations in the CH2 region of the heavy chain that reduce or alter effector function, e.g., Fc receptor binding and complement activation. For example, antibodies may have mutations such as those described in U.S. Pat. Nos. 5,624,821 and 5,648,260. Antibodies may also have mutations that stabilize the disulfide bond between the two heavy chains of an immunoglobulin, such as mutations in the hinge region of IgG4, as disclosed in the art (e.g., Angal et al. (1993) MoL Immunol. 30:105-08). See also, e.g., U.S. 2005-0037000.

In one embodiment, an anti-Fn14 antibody is modified, e.g., by mutagenesis, to provide a pool of modified antibodies. The modified antibodies are then evaluated to identify one or more antibodies which have altered functional properties (e.g., improved binding, improved stability, reduced antigenicity, or increased stability in vivo). In one implementation, display library technology is used to select or screen the pool of modified antibodies. Higher affinity antibodies are then identified from the second library, e.g., by using higher stringency or more competitive binding and washing conditions. Other screening techniques can also be used.

In some implementations, the mutagenesis is targeted to regions known or likely to be at the binding interface. If, for example, the identified binding proteins are antibodies, then mutagenesis can be directed to the CDR regions of the heavy or light chains as described herein. Further, mutagenesis can be directed to framework regions near or adjacent to the CDRs, e.g., framework regions, particularly within 10, 5, or 3 amino acids of a CDR junction. In the case of antibodies, mutagenesis can also be limited to one or a few of the CDRs, e.g., to make step-wise improvements. hi one embodiment, mutagenesis is used to make an antibody more similar to one or more germline sequences. One exemplary germlining method can include: identifying one or more germline sequences that are similar (e.g., most similar in a particular database) to the sequence of the isolated antibody. Then mutations (at the amino acid level) can be made in the isolated antibody, either incrementally, in combination, or both. For example, a nucleic acid library that includes sequences encoding some or all possible germline mutations is made. The mutated antibodies are then evaluated, e.g., to identity an antibody that has one or more additional germline residues relative to the isolated antibody and that is still useful (e.g., has a functional activity). In one embodiment, as many germline residues are introduced into an isolated antibody as possible.

In one embodiment, mutagenesis is used to substitute or insert one or more germline residues into a CDR region. For example, the germline CDR residue can be from a germline sequence that is similar (e.g., most similar) to the variable region being modified. After mutagenesis, activity (e.g., binding or other functional activity) of the antibody can be evaluated to determine if the germline residue or residues are tolerated. Similar mutagenesis can be performed in the framework regions.

Selecting a germline sequence can be performed in different ways. For example, a germline sequence can be selected if it meets a predetermined criteria for selectivity or similarity, e.g., at least a certain percentage identity, e.g., at least 75, 80, 85, 90, 91, 92, 93, 94, 95, 96, 97, 98, 99, or 99.5% identity, relative to the donor non-human antibody. The selection can be performed using at least 2, 3, 5, or 10 germline sequences. In the case of CDR1 and CDR2, identifying a similar germline sequence can include selecting one such sequence. In the case of CDR3, identifying a similar germline sequence can include selecting one such sequence, but may include using two germline sequences that separately contribute to the amino-terminal portion and the carboxy-terminal portion. In other implementations, more than one or two germline sequences are used, e.g., to form a consensus sequence.

In other embodiments, the antibody may be modified to have an altered glycosylation pattern (i.e., altered from the original or native glycosylation pattern). As used in this context, "altered" means having one or more carbohydrate moieties deleted, and/or having one or more glycosylation sites added to the original antibody. Addition of glycosylation sites to the presently disclosed antibodies may be accomplished by altering the amino acid sequence to contain glycosylation site consensus sequences; such techniques are well known in the art. Another means of increasing the number of carbohydrate moieties on the antibodies is by chemical or enzymatic coupling of glycosides to the amino acid residues of the antibody. These methods are described in, e.g., WO 87/05330, and Aplin and Wriston (1981) CRC Crit. Rev. Biochem. 22:259-306. Removal of any carbohydrate moieties present on the antibodies may be accomplished chemically or enzymatically as described in the art (Hakimuddin et al. (1987) Arch. Biochem. Biophys. 259:52; Edge et al. (1981) Anal. Biochem. 118:131; and Thotakura et al. (1987) Meth. Enzymol. 138:350). See, e.g., U.S. Pat. No. 5,869,046 for a modification that increases in vivo half life by providing a salvage receptor binding epitope.

In one embodiment, an antibody has CDR sequences that differ only insubstantially from those of described. Insubstantial differences include minor amino acid changes, such as substitutions of 1 or 2 out of any of typically 5-7 amino acids in the sequence of a CDR, e.g., a Chothia or Kabat CDR. Typically an amino acid is substituted by a related amino acid having similar charge, hydrophobic, or stereochemical characteristics. Such substitutions would be within the ordinary skills of an artisan. Unlike in CDRs, more substantial changes in structure framework regions (FRs) can be made without adversely affecting the binding properties of an antibody. Changes to FRs include, but are not limited to, humanizing a nonhuman-derived framework or engineering certain framework residues that are important for antigen contact or for stabilizing the binding site, e.g., changing the class or subclass of the constant region, changing specific amino acid residues which might alter an effector function such as Fc receptor binding (Lund et al. (1991) J Immun. 147:2657-62; Morgan et al. (1995) Immunology 86:319-24), or changing the species from which the constant region is derived. The anti-Fn14 antibodies can be in the form of full length antibodies, or in the form of fragments of antibodies, e.g., Fab, F(ab')$_2$, Fd, dAb, and scFv fragments. A fragment of an antibody can be an antigen-binding fragment, such as a variable region, e.g., VH or VL. Additional forms include a protein that includes a single variable domain, e.g., a camel or camelized domain. See, e.g., U.S. 2005-0079574 and Davies et al. (1996) Protein Eng. 9(6):531-7.

Targeting moieties disclosed herein are typically conjugated to a disclosed polymer or copolymer (e.g. PLA-PEG), and such a polymer conjugate may form part of a disclosed nanoparticle. For example, a disclosed therapeutic nanoparticle may optionally include about 0.2 to about 10 weight percent of a PLA-PEG or PLGA-PEG, wherein the PEG is functionalized with a targeting ligand (e.g. PLA-Fn14 monoclonal antibody). Such a targeting ligand may be, in some embodiments, covalently bound to the PEG, for example, bound to the PEG via a methoxy-PEG5k-amine linker by EDC carbodiimide chemistry.

Nanoparticles

Disclosed nanoparticles may have a substantially spherical (i.e., the particles generally appear to be spherical), or nonspherical configuration. For instance, the particles, upon swelling or shrinkage, may adopt a non-spherical configuration. In some cases, the particles may include polymeric blends. For instance, a polymer blend may be formed that includes a first polymer comprising a targeting moiety and a biocompatible polymer, and a second polymer comprising a biocompatible polymer but not comprising the targeting moiety. By controlling the ratio of the first and second polymers in the final polymer, the concentration and location of targeting moiety in the final polymer may be readily controlled to any suitable degree.

Disclosed nanoparticles may have a characteristic dimension of less than about 1 micrometer, where the characteristic dimension of a particle is the diameter of a perfect sphere having the same volume as the particle. For example, the particle can have a characteristic dimension of the particle can be less than about 200 nm, less than about 150 nm, less than about 100 nm, less than about 50 nm, less than about 30 nm, less than about 10 nm, less than about 3 nm, or less than about 1 nm in some cases. In particular embodiments, the nanoparticle of the present invention has a diameter of about 20 nm-200 nm.

In one set of embodiments, the particles can have an interior and a surface, where the surface has a composition different from the interior, i.e., there may be at least one compound present in the interior but not present on the surface (or vice versa), and/or at least one compound is present in the interior and on the surface at differing concentrations. For example, in one embodiment, a compound, such as a targeting moiety of a polymeric conjugate of the present invention, may be present in both the interior and the surface of the particle, but at a higher concentration on the surface than in the interior of the particle, although in some cases, the concentration in the interior of the particle may be essentially nonzero, i.e., there is a detectable amount of the compound present in the interior of the particle. In some cases, the interior of the particle is more hydrophobic than the surface of the particle. For instance, the interior of the particle may be relatively hydrophobic with respect to the surface of the particle, and a drug or other payload may be hydrophobic, and readily associates with the relatively hydrophobic center of the particle. The drug or other payload can thus be contained within the interior of the particle, which can shelter it from the external environment surrounding the particle (or vice versa). For instance, a drug or other payload contained within a particle administered to a subject will be protected from a subject's body, and the body will also be isolated from the drug. In certain embodiments, polymer particles having more than one polymer or macromolecule present, and libraries involving such polymers or macromolecules.

For example, in one set of embodiments, particles may contain more than one distinguishable polymers (e.g., copolymers, e.g., block copolymers), and the ratios of the two (or more) polymers may be independently controlled, which allows for the control of properties of the particle. For instance, a first polymer may be a polymeric conjugate comprising a targeting moiety and a biocompatible portion, and a second polymer may comprise a biocompatible portion but not contain the targeting moiety, or the second polymer may contain a distinguishable biocompatible portion from the first polymer. Control of the amounts of these polymers within the polymeric particle may thus be used to control various physical, biological, or chemical properties of the particle, for instance, the size of the particle (e.g., by varying the molecular weights of one or both polymers), the surface charge (e.g., by controlling the ratios of the polymers if the polymers have different charges or terminal groups), the surface hydrophilicity (e.g., if the polymers have different molecular weights and/or hydrophilicities), the surface density of the targeting moiety (e.g., by controlling the ratios of the two or more polymers), etc.

As a specific example, a particle can comprise a first polymer comprising a first biocompatible portion and a targeting moiety, and a second polymer comprising a second biocompatible portion different from the first biocompatible portion (e.g., having a different composition, a substantially different number of repeat units, etc.) and the targeting moiety. As yet another example, a first polymer may comprise a biocompatible portion and a first targeting moiety, and a second polymer may comprise a biocompatible portion and a second targeting moiety different from the first targeting moiety. For example, disclosed herein is a therapeutic polymeric nanoparticle capable of binding to a target, comprising a first non-functionalized polymer; an optional second non-functionalized polymer; a functionalized polymer comprising a targeting moiety; and a biologically active agent; wherein said nanoparticle comprises about 15 to about 300 molecules of functionalized polymer, or about 20 to about 200 molecule, or about 3 to about 100 molecules of functionalized polymer.

In a particular embodiment, the polymer of the first or second macromolecules of the nanoparticle of the invention is PLA, PLGA, or PEG, or copolymers thereof. In a specific embodiment, the polymer of the first macromolecule is a PLGA-PEG copolymer, and the second macromolecule is a PLGA-PEG copolymer, or a PLA-PEG copolymer. For example, exemplary nanoparticle may have a PEG corona with a density of about 0.065 g/cm$^3$, or about 0.01 to about 0.10 g/cm$^3$. Disclosed nanoparticles may be stable (e.g. retain substantially all biologically active agents) for example in a solution that may contain a saccharide, for at least about 3 days, about 4 days or at least about 5 days at room temperature, or at 25° C.

In some embodiments, disclosed nanoparticles may also include a fatty alcohol, which may increase the rate of drug release. For example, disclosed nanoparticles may include a $C_8$-$C_{30}$ alcohol such as cetyl alcohol, octanol, stearyl alcohol, arachidyl alcohol, docosonal, or octasonal. Nanoparticles may have controlled release properties, e.g., may be capable of delivering an amount of biologically active agent to a patient, e.g., to specific site in a patient, over an extended period of time, e.g. over 1 day, 1 week, or more. In some embodiments, disclosed nanoparticles substantially immediately releases (e.g. over about 1 minute to about 30 minutes) less than about 2%, less than about 5%, or less than about 10% of a biologically active agent (e.g. a therapeutic agent such as taxane), for example when places in a phosphate buffer solution at room temperature and/or at 37° C.

For example, disclosed nanoparticles that include a biologically active agent, may, in some embodiments, may release the biologically active agent when placed in an aqueous solution at e.g., 25° C. with a rate substantially corresponding to a) from about 0.01 to about 20% of the total biologically active agent is released after about 1 hour; b) from about 10 to about 60% of the biologically active agent is released after about 8 hours; c) from about 30 to about 80% of the total biologically active agent is released after about 12 hours; and d) not less than about 75% of the total is released after about 24 hours.

In some embodiments, after administration to a subject or patient of a disclosed nanoparticle or a composition that includes a disclosed nanoparticle, the peak plasma concentration ($C_{max}$) of the biologically active agent in the patient substantially higher as compared to a $C_{max}$ of the biologically active agent if administered alone (e.g., not as part of a nanoparticle).

In another embodiment, a disclosed nanoparticle including a biologically active agent, when administered to a subject, may have a $t_{max}$ of biologically active agent substantially longer as compared to a $t_{max}$ of the biologically active agent administered alone. As a specific example, the nanoparticle may contain polymers including a relatively hydrophobic biocompatible polymer and a relatively hydrophilic targeting moiety, such that, during nanoparticle formation, a greater concentration of the hydrophilic targeting moiety is exposed on the surface and a greater concentration of the hydrophobic biocompatible polymer is present within the interior of the particle.

In some embodiments, the biocompatible polymer is a hydrophobic polymer. Non-limiting examples of biocompatible polymers include polylactide, polyglycolide, and/or poly(lactide-co-glycolide). In a different embodiment, this disclosure provides for a nanoparticle comprising 1) a polymeric matrix; 2) optionally, an amphiphilic compound or layer that surrounds or is dispersed within the polymeric matrix forming a continuous or discontinuous shell for the particle; 3) a non-functionalized polymer that may form part of the polymeric matrix, and 4) a low molecular weight PSMA ligand covalently attached to a polymer, which may form part of the polymeric matrix. For example, an amphiphilic layer may reduce water penetration into the nanoparticle, thereby enhancing drug encapsulation efficiency and slowing drug release. As used herein, the term "amphiphilic" refers to a property where a molecule has both a polar portion and a non-polar portion. Often, an amphiphilic compound has a polar head attached to a long hydrophobic tail. In some embodiments, the polar portion is soluble in water, while the non-polar portion is insoluble in water. In addition, the polar portion may have either a formal positive charge, or a formal negative charge. Alternatively, the polar portion may have both a formal positive and a negative charge, and be a zwitterion or inner salt. For purposes of the invention, the amphiphilic compound can be, but is not limited to, one or a plurality of the following: naturally derived lipids, surfactants, or synthesized compounds with both hydrophilic and hydrophobic moieties. Specific examples of amphiphilic compounds include, but are not limited to, phospholipids, such as 1,2 distearoyl-snglycero-3-phosphoethanolamine (DSPE), dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), and dilignoceroylphatidylcholine (DLPC), incorporated at a ratio of between 0.01-60 (weight lipid/w polymer), most preferably between 0.1-30 (weight lipid/w polymer). Phospholipids which may be used include, but are not limited to, phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and .beta.-acyl-y-alkyl phospholipids. Examples of phospholipids include, but are not limited to, phosphatidylcholines such as dioleoylphosphatidylcholine, dimyristoylphosphatidylcholine, ipentadecanoylphosphatidylcholine dilauroylphosphatidylcholine, dipalmitoylphosphatidylcholine (DPPC), distearoylphosphatidylcholine (DSPC), iarachidoylphosphatidylcholine (DAPC), dibehenoylphosphatidylcho-line (DBPC), itricosanoylphosphatidylcholine (DTPC), dilignoceroylphatidylcholine (DLPC); ndphosphatidylethanolamines such as dioleoylphosphatidylethanolamine or 1-hexadecyl-2-almitoylglycerophosphoethanolamine.

Synthetic phospholipids with asymmetric acyl chains (e.g., with one acyl chain of 6 carbons and another acyl chain of 12 carbons) may also be used. In a particular embodiment, an amphiphilic component that can be used to form an amphiphilic layer is lecithin, and, in particular, phosphatidylcholine. Lecithin is an amphiphilic lipid and, as such, forms a phospholipid bilayer having the hydrophilic (polar) heads facing their surroundings, which are oftentimes aqueous, and the hydrophobic tails facing each other. Lecithin has an advantage of being a natural lipid that is available from, e.g., soybean, and already has FDA approval for use in other delivery devices. In addition, a mixture of lipids such as lethicin is more advantageous than one single pure lipid. In certain embodiments a disclosed nanoparticle has an amphiphilic monolayer, meaning the layer is not a phospholipid bilayer, but exists as a single continuous or discontinuous layer around, or within, the nanoparticle. The amphiphilic layer is "associated with" the nanoparticle of the invention, meaning it is positioned in some proximity to the polymeric matrix, such as surrounding the outside of the polymeric shell, or dispersed within the polymers that make up the nanoparticle.

PEG density, targeting molecule type and/or density, and polymer type may be altered in certain embodiments to optimize Fn14 binding. Table 1 is an example of a summary of formulation variables for synthesis and screening of Fn14-targeted BPNs.

TABLE 1

| Polymers | Therapeutics | Targeting Molecule | Formulation variables | Characterization methods |
|---|---|---|---|---|
| PLGA (50:50) | Cisplatin | ITEM4 | Polymer blend composition PEG MW (2 kDa, 5 kDa, 10 kDa) PEG surface density (PEG to polymer ratio) Targeting molecule density | Dynamic light scattering (size, ζ-potential) Electron microscopy (morphology) NMR & protein assays (quantitation of PEG density and targeting molecule density) Surface plasmon resonance particle binding to Fn14 and brain ECM) |
| PLGA (75:25) | Doxorubicin | ITEM4 scFv | | |
| PLA | Etoposide | ITEM4 Fab | | |
| PGA | Paclitaxel | TWEAK | | |
| PAA | Small molecule drugs Pathway inhibitors | | | |

Preparation of Nanoparticles

Another aspect of this disclosure is directed to methods of making the disclosed nanoparticles. In some embodiments, 40-nm to 200-nm red fluorescent COOH-modified polystyrene (PS) particles were covalently modified with methoxy (MeO)-PEG-amine (NH2) (5kDA MW) by carboxyl amine reaction, following a modified protocol previously described [32-33]. These two protocols were combined and optimized to obtain dense PEG coatings, a near-neutral ξ-potential, and low PDI, for 40 nm-200 nm PS particles. In embodiments to formulate brain tissue penetrating coated nanoparticles, 100 nm carboxylate-modified polystyrene (PS—COOH) nanoparticles were covalently modified with methoxy-PEG5k-amine by EDC carbodiimide chemistry, following a modified protocol described previously [33-34]. In other embodiments, coated-ITEM4 nanoparticles, were prepared using a different proportion of PEG (methoxy-PEG5k-amine to malemide-PEG5k-amine) for initial particle PEGylation; specifically, 10 mol % and 50 mol % of maleimide-PEG5k-amine was used for CNP-ITEM4 (low) and CNP-ITEM4 (high) nanoparticles, respectively. ITEM 4-SH was conjugated onto the surface of the nanoparticles containing maleimide-functionalized PEG by maleimide-thiol chemistry.

Biologically Active Agents

According to the present invention, any biologically active agents including, for example, therapeutic agents (anti-cancer agents, anti-AD agents, anti-PD agents, anti-HD agents, anti-epilepsy agents), diagnostic agents (e.g. contrast agents; radionuclides; and fluorescent, luminescent, and magnetic moieties), prophylactic agents (e.g. vaccines), nutraceutical agents (e.g. vitamins, minerals, etc.), imaging agents (e.g., via magnetic resonance imaging, positron emission imaging, radio-isotope imagining) and/or gene therapy agents (e.g. nucleic acids such as RNA and DNA) may be delivered by the disclosed nanoparticles. Exemplary biologically active agents to be delivered in accordance with the present invention include, but are not limited to, drugs, small molecules (e.g. cytotoxic agents), nucleic acids (e.g., DNA, RNA, siRNA, RNAi, and microRNA agents), proteins (e.g. antibodies), peptides, lipids, carbohydrates, hormones, metals, radioactive elements and compounds, vaccines, immunological agents, etc., and/or combinations thereof. Molecular imaging agents are known in the art and are readily available in the MICAD database developed by the NIH and online. They enable the visualization of phenomena with cellular and subcellular level resolutions and therefore have enormous potential in improving disease diagnosis and therapy assessment and are known in the art. In certain embodiments, the nanoparticle has from a 1% to 100% load capacity for the biologically active agent. In some embodiments, the therapeutic agent to be delivered is a drug useful in the treatment of cancer (e.g., brain cancer, specifically glioblastoma).

In certain embodiments, a targeting moiety, if used, may target or cause the nanoparticle to become localized at specific portions within a subject, and the payload may be delivered to those portions. In a particular embodiment, the drug or other payload may is released in a controlled release manner from the particle and allowed to interact locally with the particular targeting site (e.g., a tumor). The term "controlled release" (and variants of that term) as used herein (e.g., in the context of "controlled-release system") is generally meant to encompass release of a substance (e.g., a drug) at a selected site or otherwise controllable in rate, interval, and/or amount. Controlled release encompasses, but is not necessarily limited to, substantially continuous delivery, patterned delivery (e.g., intermittent delivery over a period of time that is interrupted by regular or irregular time intervals), and delivery of a bolus of a selected substance (e.g., as a predetermined, discrete amount if a substance over a relatively short period of time (e.g., a few seconds or minutes)).

The biologically active agent may be a therapeutic agent such a taxane such as paclitaxel (or its derivatives such as DHA-paclitaxel or PG-paclitaxel) or docetaxel. In one set of embodiments, the payload is a drug or a combination of more than one drug. Such particles may be useful, for example, in embodiments where a targeting moiety may be used to direct a particle containing a drug to a particular localized location within a subject, e.g., to allow localized delivery of the drug to occur. For example, biodegradable NPs may be composed of block copolymers of poly(lactic-co-glycolic acid) (PLGA) and PEG and loaded with 2.5% wt % paclitaxel Exemplary therapeutic agents include chemotherapeutic agents such as doxorubicin (adriamycin), gemcitabine (gemzar), daunorubicin, procarbazine, mitomycin, cytarabine, etoposide, methotrexate, venorelbine, 5-fluorouracil (5-FU), vinca alkaloids such as vinblastine or vincristine; bleomycin, paclitaxel (taxol), docetaxel (taxotere), aldesleukin, asparaginase, busulfan, carboplatin, cladribine, camptothecin, CPT-11, 10-hydroxy-7-ethyl-camptothecin (SN38), dacarbazine, S—I capecitabine, ftorafur, 5'deoxyfluorouridine, UFT, eniluracil, deoxycytidine, 5-azacytosine, 5-azadeoxycytosine, allopurinol, 2-chloroadenosine, trimetrexate, aminopterin, methylene-10-deazaminopterin (MDAM), oxaplatin, picoplatin, tetraplatin, satraplatin, platinum-DACH, ormaplatin, CI-973, JM-216, and analogs thereof, epirubicin, etoposide phosphate, 9-aminocamptothecin, 10,11-methylenedioxycamptothecin, karenitecin, 9-nitrocamptothecin, TAS 103, vindesine, L-phenylalanine mustard, ifosphamidemefosphamide, perfosfamide, trophosphamide carmustine, semustine, epothilones A-E, tomudex, 6-mercaptopurine, 6-thioguanine, amsacrine, etoposide phosphate, karenitecin, acyclovir, valacyclovir, ganciclovir, amantadine, rimantadine, lamivudine, zidovudine, bevacizumab, trastuzumab, rituximab, 5-Fluorouracil, and combinations thereof. Non-limiting examples of potentially suitable drugs include anticancer agents, including, for example, docetaxel, mitoxantrone, and mitoxantrone hydrochloride.

In another embodiment, the payload may be an anti-cancer drug such as 20-epi-1,25 dihydroxyvitamin D3, 4-ipomeanol, 5-ethynyluracil, 9-dihydrotaxol, abiraterone, acivicin, aclarubicin, acodazole hydrochloride, acronine, acylfiilvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, anti-dorsalizdng morphogenetic protein-1, antiestrogen, antineoplaston, antisense oligonucleotides, aphidicolin glycinate, apoptosis gene modulators, apoptosis regulators, apurinic acid, ARA-CDP-DLPTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisazuidinyl-spermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caraceraide, carbetimer, carboplatin, carboxamide-amino-triazole, carboxyamidotriazole, carest M3, carmustine, earn 700, cartilage derived inhibitor, carubicin hydrochloride, carzelesin, casein kinase inhibitors, castanospermine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethyhiorspermine, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocannycin SA, ebselen, ecomustine, edatrexate, edelfosine, edrecolomab, eflomithine, eflomithine hydrochloride, elemene, elsarnitrucin, emitefur, enloplatin, enpromate, epipropidine, epirubicin, epirubicin hydrochloride, episteride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, fluorocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ihnofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatm, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide, lobaplatin, lombricine, lometrexol, lometrexol sodium, lomustine, lonidamine, losoxantrone, losoxantrone hydrochloride, lovastatin, loxoribine, lurtotecan, lutetium texaphyrin lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, O6-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazorurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RH retinamide, RNAi, rogletimide, rohitukine, romurtide, roquinimex, rubiginone B1, ruboxyl, safingol, safingol hydrochloride, saintopin, sarcnu, sarcophytol A, sargramostim, SDI1 mimetics, semustine, senescence derived inhibitor 1, sense oligonucleotides, signal transduction inhibitors, signal transduction modulators, simtrazene, single chain antigen binding protein, sizofiran, sobuzoxane, sodium borocaptate, sodium phenylacetate, solverol, somatomedin binding protein, sonermin, sparfosafe sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine or vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride.

The biologically active agent may be a therapeutic agent such as a drug used to treat Parkinson's disease which include L-dopa, selegiline, apomorphine and anticholinergics. L-dopa (levodihydroxy-phenylalanine) (sinemet) is a dopamine precursor which can cross the blood-brain barrier and be converted todopamine in the brain. Unfortunately, L-dopa has a short half life in the body and it is typical after long use (i.e. after about 4-5 years) for the effect of L-dopa to become sporadic and unpredictable, resulting in fluctuations in motor function, dyskinesias and psychiatric side effects. Additionally, L-dopa can cause B vitamin deficiencies to arise. Selegiline (Deprenyl®, Eldepryl®) has been used as an alternative to L-dopa, and acts by reducing the breakdown of dopamine in the brain. Unfortunately, Selegiline becomes ineffective after about nine months of use. Apomorphine, a dopamine receptor agonist, has been used to treat Parkinson's disease, although is causes severe vomiting when used on its own, as well as skin reactions, infection, drowsiness and some psychiatric side effects. Systemically administered anticholinergic drugs (such as benzhexol and orphenedrine) have also been used to treat Parkinson's disease and act by reducing the amount of acetylcholine produced in the brain and thereby redress the dopamine/acetylcholine imbalance present in Parkinson's disease. Unfortunately, about 70% of patients taking systemically administered anticholinergics develop serious neuropsychiatric side effects, including hallucinations, as well as dyskinetic movements, and other effects resulting from wide anticholinergic distribution, including vision effects, difficulty swallowing, dry mouth and urine retention. [34].

Biologically active agents such as therapeutic agents that are drugs for treatment of AD cannot cure AD or stop it from progressing, but they may help lessen symptoms, such as memory loss and confusion, for a limited time. The FDA has approved two types of medications—cholinesterase inhibitors (Aricept®, Exelon®, Razadyne®, Cognex®) and memantine (Namenda®)—to treat the cognitive symptoms (memory loss, confusion, and problems with thinking and reasoning) of Alzheimer's disease. As Alzheimer's progresses, brain cells die and connections among cells are lost, causing cognitive symptoms to worsen. While current medications cannot stop the damage Alzheimer's causes to brain cells, they may help lessen or stabilize symptoms for a limited time by affecting certain chemicals involved in carrying messages among the brain's nerve cells. Doctors sometimes prescribe both types of medications together. Some doctors also prescribe high doses of vitamin E for cognitive changes of Alzheimer's disease.

No treatments can alter the course of Huntington's disease. But therapeutic agents can lessen some symptoms of movement and psychiatric disorders. And multiple interventions can help a person adapt to changes in his or her abilities for a certain amount of time. Medication management is likely to evolve over the course of the disease, depending on the overall treatment goals. Also, drugs to treat some symptoms may result in side effects that worsen other symptoms. Therefore, the treatment goals and plan will be regularly reviewed and updated. Drugs to treat movement disorders include the following: Tetrabenazine (Xenazine) is specifically approved by the FDA to suppress the involuntary jerking and writhing movements (chorea) associated with Huntington's disease. Other possible side effects include drowsiness, nausea and restlessness. Antipsychotic drugs, such as haloperidol (Haldol®) and chlorpromazine, have a side effect of suppressing movements. Therefore, they may be beneficial in treating chorea. These drugs may, however, worsen involuntary contractions (dystonia) and muscle rigidity. Newer drugs, such as risperidone (Risperdal®) and quetiapine (Seroquel®), may have fewer side effects but still should be used with caution, as they may also worsen symptoms. Other medications that may help suppress chorea include amantadine, levetiracetam (Keppra®) and clonazepam (Klonopin®). At high doses, amantadine can worsen the cognitive effects of Huntington's disease. It may also cause leg swelling and skin discoloration. Side effects of levetiracetam include nausea, stomach upset and mood swings. Clonazepam may worsen the cognitive side effects of Huntington's disease and cause drowsiness. It also has a high risk of dependence and abuse.

In certain embodiments, it will be appreciated that the exact dosage of the biologically active agent (e.g., therapeutic agent) is chosen by the individual physician in view of the patient to be treated, in general, dosage and administration are adjusted to provide an effective amount of the therapeutic agent to the patient being treated. The effective amount of a therapeutic agent refers to the amount necessary to elicit the desired biological response. As will be appreciated by those of ordinary skill in this art, the effective amount of a therapeutic agent may vary depending on such factors as the desired biological endpoint, the drug to be delivered, the target tissue, the route of administration, etc. In certain embodiments, the nanoparticle releases an effective amount of the biologically active agent over a period of at least 10 minutes, 20 minutes, 30 minutes, one hour, two hours, four hours, six hours, ten hours, one day, three days, seven days, ten days, two weeks, one month, or longer. The effective amount of an anti-cancer drug might be the amount that results in a reduction in tumor size by a desired amount over a desired period of time. Additional factors which may be taken into account include the severity of the disease state; age, weight and gender of the patient being treated; diet, time and frequency of administration; drug combinations; reaction sensitivities; and tolerance/response to therapy. It will be understood, however, that the total daily usage of the therapeutic agents in the delivery system of the present invention will be decided by the attending physician within the scope of sound medical judgment. Such information can then be used to determine useful doses and routes for administration in humans.

Pharmaceutical Formulations

Nanoparticles disclosed herein may be combined with pharmaceutical acceptable carriers to form a pharmaceutical composition, according to another aspect of the invention. As would be appreciated by one of skill in this art, the carriers may be chosen based on the route of administration as described below, the location of the target issue, the drug being delivered, the time course of delivery of the drug, etc.

The pharmaceutical compositions of this invention can be administered to a patient by any means known in the art including but not limited to stereotaxic injection. The pharmaceutical compositions of the present invention may be prepared for administration by injection to the target area of the brain. Further within other embodiments the compounds or compositions provided herein may be admixed with other carriers (e.g., polymers), imaging agents (e.g. via magnetic resonance imaging, optical imaging, positron emission tomography, X-ray computed tomography, and ultrasound imaging) and implanted on or contained within devices which are designed to release such compounds. Within further embodiments, the compounds may be delivered under radioscopic or other visual guidance to a desired site.

Pharmaceutical compositions of the present invention may be placed within containers, or kits, along with packaging material which provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) which may be necessary to reconstitute the pharmaceutical composition.

Sterile injectable solutions can be prepared by incorporating the nanoparticle in the required amount in an appropriate solvent with one or a combination of the ingredients known in the art, as required, followed by filter sterilization. These injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

In certain embodiments, it will be appreciated that the exact dosage of the Fn14 protein targeted nanoparticle is chosen by the individual physician in view of the patient to be treated, in general, dosage and administration are adjusted to provide an effective amount of the nanoparticle to the patient being treated. As used herein, the "effective amount" of an Fn14 protein-targeted nanoparticle refers to the amount necessary to elicit the desired biological response. As will be appreciated by those of ordinary skill in this art, the effective amount of Fn14 protein-targeted particle may vary depending on such factors as the desired biological endpoint, the drug to be delivered, the target tissue, the route of administration, etc. For example, the effective amount of Fn14 protein-targeted particle containing an anti-cancer drug might be the amount that results in a reduction in tumor size by a desired amount over a desired period of time. Additional factors which may be taken into account include the severity of the disease state; age, weight and gender of the patient being treated; diet, time and frequency of administration; drug combinations; reaction sensitivities; and tolerance/response to therapy. The nanoparticles of the invention may be formulated in dosage unit form for ease of administration and uniformity of dosage. In certain embodiments, the Fn14 targeted nanoparticle releases an effective amount of the biologically active agent over a period of at least 10 minutes, 20 minutes, 30 minutes, one hour, two hours, four hours, six hours, ten hours, one day, three days, seven days, ten days, two weeks, one month, or longer. The expression "dosage unit form" as used herein refers to a physically discrete unit of nanoparticle appropriate for the patient to be treated. It will be understood, however, that the total daily usage of the compositions of the present invention will be decided by the attending physician within the scope of sound medical judgment. For any nanoparticle, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans.

Therapeutic efficacy and toxicity of nanoparticles can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices may be useful in some embodiments. The data obtained from cell culture assays and animal studies can be used in formulating a range of dosage for human use.

In an exemplary embodiment, a pharmaceutical composition is disclosed that includes a plurality of nanoparticles each comprising a biologically active agent; about 0.1 to about 30 mole percent of the total polymer content, or about 0.1 to about 20 mole percent, or about 0.1 to about 10 mole percent, or about 1 to about 5 mole percent of the total polymer content of a nanoparticle, that is conjugated to Fn14 monoclonal antibody having a molecular weight between about 100 g/mol and 500 g/mol; and a pharmaceutically acceptable excipient. For example, the polymer may have about 0.001 and 5 weight percent of the Fn14 antibody with respect to total polymer content. In some embodiments, a composition suitable for freezing is contemplated, including nanoparticles disclosed herein and a solution suitable for freezing, e.g. a sucrose solution is added to the nanoparticle suspension. The sucrose may e.g., as a cryoprotectant to prevent the particles from aggregating upon freezing. For example, provided herein is a nanoparticle formulation comprising a plurality of disclosed nanoparticles, sucrose and water; wherein the nanoparticles/sucrose/water is about 3-30%/10-30%/50-90% (w/w/w) or about 5-10%/10-15%/80-90% (w/w/w).

Methods of Treatment

In some embodiments, targeted structure-specific particulate-based delivery systems in accordance with the present invention may be used to treat, alleviate, ameliorate, relieve, delay onset of, inhibit progression of, reduce severity of and/or reduce incidence of one or more symptoms or features of a disease, disorder, and/or condition of the brain. In some embodiments, these targeted structure-specific particulate-based delivery systems may be used to treat solid tumors, e.g., cancer and/or cancer cells. In certain embodiments, inventive targeted particles may be used to treat any cancer wherein Fn14 is expressed on the surface of cancer cells or in the tumor neovasculature in a subject in need thereof, including the neovasculature of glioblastoma tumors.

In one aspect of the invention, a method for the treatment of a disease or disorder, specifically, cancer (e.g. of the brain, glioblastoma, of the lung, of the breast) is provided. In some embodiments, the treatment of cancer comprises administering a therapeutically effective amount of targeted nanoparticles to a subject in need thereof, in such amounts and for such time as is necessary to achieve the desired result. In one aspect of the invention, a method for administering inventive compositions to a subject suffering from cancer (e.g. glioblastoma) is provided. In some embodiments, particles to a subject in such amounts and for such time as is necessary to achieve the desired result (i.e. treatment of cancer). Inventive therapeutic protocols involve administering a therapeutically effective amount of an inventive targeted particle to a healthy individual (i.e., a subject who does not display any symptoms of cancer and/or who has not been diagnosed with cancer). For example, healthy individuals may be "immunized" with an inventive targeted particle prior to development of cancer and/or onset of symptoms of cancer; at risk individuals (e.g., patients who have a family history of cancer; patients carrying one or more genetic mutations associated with development of cancer; patients having a genetic polymorphism associated with development of cancer; patients infected by a virus associated with development of cancer; patients with habits and/or lifestyles associated with development of cancer; etc.) can be treated substantially contemporaneously with (e.g., within 48 hours, within 24 hours, or within 12 hours of) the onset of symptoms of cancer. Of course individuals known to have cancer may receive inventive treatment at any time.

In other embodiments, the nanoparticles of the present invention can be used to inhibit the growth of cancer cells, e.g., glioblastoma cells. Preferably, such an inhibition at the cellular level may reduce the size, deter the growth, reduce the aggressiveness, or prevent or inhibit metastasis of a cancer in a patient. Those skilled in the art can readily determine, by any of a variety of suitable indicia, whether cancer cell growth is inhibited. Inhibition of cancer cell growth may be evidenced, for example, by arrest of cancer cells in a particular phase of the cell cycle, e.g., arrest at the G2/M phase of the cell cycle. Inhibition of cancer cell growth can also be evidenced by direct or indirect measurement of cancer cell or tumor size. In human cancer patients, such measurements generally are made using well known imaging methods such as magnetic resonance imaging, computerized axial tomography and X-rays. Cancer cell growth can also be determined indirectly, such as by determining the levels of circulating carcinoembryonic antigen, prostate specific antigen or other cancer-specific antigens that are correlated with cancer cell growth. Inhibition of cancer growth is also generally correlated with prolonged survival and/or increased health and well-being of the subject.

Also provided herein are methods of administering to a patient a nanoparticle disclosed herein including an active agent, wherein, upon administration to a patient, such nanoparticles substantially reduces the volume of distribution and/or substantially reduces free Cmax, as compared to administration of the agent alone (i.e. not as a disclosed nanoparticle).

Gene Therapy

Complex genetic mutations are common in brain cancer, making gene therapy an attractive approach to repair or modulate altered genes and cellular pathways. Gene therapy is the administration of a gene encoding a protein of interest as a pharmaceutical agent to treat disease. It derives its name from the idea that a gene can be administered to supplement or alter other genes within an individual's cells as a therapy to treat disease. Scientists first took the logical step of trying to introduce genes directly into human cells, focusing on diseases caused by single-gene defects, such as cystic fibrosis, hemophilia, muscular dystrophy and sickle cell anemia. However, this has proven more difficult than modifying bacteria, primarily because of the problems involved in carrying large sections of DNA and delivering them to the correct site on the comparatively large target genome. Today, most gene therapy studies are aimed at cancer and hereditary diseases linked to a genetic defect. There are a variety of different methods to replace or repair the genes targeted in gene therapy. A normal gene may be inserted into a nonspecific location within the genome to replace a nonfunctional gene. Or, an abnormal gene could be swapped for a normal gene through homologous recombination. On the other hand, the abnormal gene could be repaired through selective reverse mutation, which returns the gene to its normal function. The regulation (the degree to which a gene is turned on or off) of a particular gene could be altered.

The most common form of gene therapy involves using DNA that encodes a functional, therapeutic gene in order to replace a mutated gene. Other forms involve directly correcting a mutation, or using DNA that encodes a therapeutic protein drug (rather than a natural human gene) to provide treatment. In gene therapy, the gene is packaged within a "vector," which is used to transfer the gene to the targeted cells within the body. Once inside, the DNA is expressed by the cell machinery, resulting in the production of therapeutic protein, which in turn treats the patient's disease. Gene therapy utilizes the delivery of DNA into cells, which can be accomplished by a number of methods, summarized below.

The majority of current gene therapy-based clinical trials have used viruses to deliver therapeutic DNA. While some viruses can provide safe gene transfer in humans, Phase III clinical trials have failed to show therapeutic efficacy due in part to significant host immune responses, limited therapeutic distribution, and rapid clearance. Non-viral gene vectors can offer DNA delivery without the risk of immunogenicity and/or insertional mutagenesis that are common with viral vectors and have emerged as an alternative to viral strategies. Benefits of non-viral vectors include reduced immunogenicity, ease of manufacturing, lack of risk of vector replication and insertion, and ability to accommodate larger plasmid DNA compared to commonly tested viruses such as adeno-associated viruses. The clinical development of non-viral vectors has been hindered in part by relatively low gene transfer efficiencies compared to viral vectors. This may be due to the inability to overcome various biological barriers. A particularly challenging barrier involves endo-lysosomal trafficking within cells, where therapeutic DNA is often degraded in the acidic and enzyme-rick late-endosomes and lysosomes before reaching the nucleus. A common strategy to overcome this barrier is to incorporate functional groups with acid-base buffering capacity between pH 5.1-7.4, which presumably mediates escape from lower pH endo-lysosomal degradation.

In certain embodiments, targeted structure-specific particulate-based delivery systems may comprise highly compacted DNA nanoparticles, composed of 30-mer lysine are conjugated to polyethylene glycol via a single cysteine moiety ($CK_{30}PEG$) and represent a promising non-viral technology that has demonstrated remarkable effectiveness in delivering genes to the brain, eyes and lungs, with minimal toxicity and immunogenicity. A pH-responsive DNA nanoparticle, $CH_{12}K_{18}PEG_5K$ was developed by inserting a poly-L-histidine segment between PEG and poly-L-lysine to engineer a triblock copolymer. [35]. In vitro gene transfer efficiency of $CH_{12}K_{18}PEG_5K$ DNA nanoparticles was evaluated in GL261 cells using the reporter plasmid, pRNAT-H1.3/Hygro/siFlu. Highly compacted $CH_{12}K_{18}PEG_{5k}$ DNA nanoparticles tested in brain tumor gene delivery studies also showed efficient gene transfer to brain tumor cells in vivo and effectively silenced a tumor-specific transgene (firefly luciferase) following direct injection into mouse intracranial GBM. Simply, $CH_{12}K_{18}PEG_{5K}$ DNA nanoparticles were able to knockdown luciferase in an intracranial GL261 mouse glioma model. These results demonstrate the utility of using this DNA nanoparticle-based technology for delivering genes to tumor cells as a possible therapeutic approach for patients with brain cancer.

It is further contemplated that in other embodiments, any potential non-specific binding of these DNA nanoparticles to the brain can be minimized by enabling active targeting of Fn14-positive glioblastoma cells by incorporating a targeting moiety onto the highly compacted DNA nanoparticle having the gene construct of interest. Achieving effective distribution of therapies to the complete extent of invasive gliomas and delivering those therapies as directly as possible to the tumor cells, while having minimal bystander effects on adjacent neurons and glia, it a major goal of advanced delivery systems for this disease. Therefore, targeting of therapeutics to tumor cells and/or the close microenvironment represents a critical next step. Previous studies exploring this approach for GBM have included: targeting tumor cell surface molecules such as epidermal growth factor receptor [35] and interleukin 13 receptor [36], and targeting tumor-associated extracellular matrix components such as Tenascin C21. These targeting moieties have been limited by three major problems: (1) adhesive interactions with non-target structures, (2) target present on only a relatively small percentage of tumor cells or regions, and (3) target not specific for invading cells. To address these problems, the DNA nanoparticle can be further developed to be coupled with tumor cell targeting molecules to specifically adhere to the structure(s) of interest.

To deliver the DNA nanoparticle specifically to a particular region of the brain and/or to a particular population of cells of the CNS, the vector may be administered by stereotaxic microinjection. For example, patients have the stereotactic frame base fixed in place (screwed into the skull). The brain with stereotactic frame base (MRI compatible with fiducial markings) is imaged using high resolution MRI. The MRI images are then transferred to a computer which runs stereotactic software. A series of coronal, sagittal and axial images are used to determine the target (site of nanoparticle injection) and trajectory. The software directly translates the trajectory into 3 dimensional coordinates appropriate for the stereotactic frame. Burr holes are drilled above the entry site and the stereotactic apparatus positioned with the needle implanted at the given depth. The nanoparticle is then injected at the target sites. Since the nanoparticle integrates into the target cells, rather than producing viral particles, the subsequent spread of the vector is minor, and mainly a function of passive diffusion from the site of injection and of course the desired transsynaptic transport, prior to integration. The degree of diffusion may be controlled by adjusting the ratio of vector to fluid carrier.

The target cells of the nanoparticles of the present invention may include glioblastoma cells in brain cancer patients, and cells of the central nervous systems of a subject afflicted a neurodegenerative disease such as Parkinson's disease, Alzheimer's disease, or Huntington's disease, preferably neural cells. Preferably the subject is a human being, generally an adult.

However the invention encompasses delivering the DNA nanoparticle to biological models of the disease. In that case, the biological model may be any mammal at any stage of development at the time of delivery, e.g., embryonic, fetal, infantile, juvenile or adult, preferably it is an adult. Furthermore, the target CNS cells may be essentially from any source, especially nonhuman primates and mammals of the orders Rodenta (mice, rats, rabbit, hamsters), Carnivora (cats, dogs), and Arteriodactyla (cows, pigs, sheep, goats, horses) as well as any other non-human system (e.g. zebrafish model system).

Biodegradable polymeric nanoparticles facilitate nonviral gene transfer to human embryonic stem cells (hESCs). Small (approximately 200 nm), positively charged (approximately 10 mV) particles are formed by the self-assembly of cationic, hydrolytically degradable poly(beta-amino esters) and plasmid DNA.

5. Examples

The invention is illustrated herein by the experiments described by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

Example 1: Materials and Methods 5 kDa MW PEG, methoxy-PEG5k-amine and thiol reactive malemide-PEG5k-amine, were purchased from Creative PEGWorks (Winston Salem, N.C.). Lab-Tek glass-bottom tissue culture plates and Zeba Spin Columns (7 kDa MW cut-off) were purchased from ThermoFisher Scientific (Rochester, N.Y.). ITEM4 monoclonal antibody was purchased from eBioscience (San Diego, Calif.). Red (0.1 μm, 540/590 excitation/emission) and Blue (0.1 μm, 350/440 excitation/emission) carboxylate-modified FluoSpheres and Hoechst 34580 were purchased from Invitrogen (Carlsbad, Calif.). Non-fluorescent carboxyl microspheres (0.1 μm) were purchased from Bang's Laboratories (Fishers, Ind.). D-Luciferin was obtained from Promega (Madison, Wis.). Thiol Quantification Assay Kit (Fluorometric) was from Abcam (Cambridge, Mass.). 1-Ethyl-3-[3-dimethylaminopropyl]carbodiimide hydrochloride (EDC), N-hydroxysulfosuccinimide (sulfo-NHS), Phosphate Buffer, 2-iminothilane hydrochloride, and all other chemicals were purchased from Sigma-Aldrich (St. Louis, Mo.).

Preparation of ITEM4-SH

ITEM4 was thiol-modified via reaction of free amines with 2-iminothiolane. Briefly, ITEM4 (0.5 mg/mL) was mixed with 2-iminothiolane (400× molar excess to ITEM4) in 100 mM phosphate buffer with EDTA (pH 7.2, 150 mM NaCl, 5 mM EDTA) in a siliconized tube. The reaction was allowed to proceed for 2 h at room temperature to yield thiolated ITEM4 (ITEM4-SH). After the reaction, resulting solution was purified with Zeba Spin Columns (7 kDa MW cut-off) and frozen immediately to avoid potential disulfide bond formation (S—S) between newly generated thiol groups. The degree of thiolation of ITEM 4-SH was determined using the Thiol Quantification Assay Kit (Fluorometric assay, Abcam, Cambridge, Mass.) as per the manufacturer's recommendations. Gluathione (GSH) standard was used to generate a standard curve to determine the number of thiol groups per ITEM4.

Nanoparticle Preparation

The detailed methods below are the main formulation methods used for generation of tissue penetrating nanoparticles (TPN). However, there are a wide variety of formulation methods, polymers, ligands, and chemistries that can be used to achieve targeted, tissue penetrating nanoparticles as described in U.S. Patent Application No. 2013/0183244A.

a. Non-Biodegradable Nanoparticles

Nanoparticles were synthesized from COOH-modified polystyrene (PS) NP (PS—COOH). First, PS—COOH nanoparticles were added to a siliconized microcentrifuge tube (Sigma) and completed to a volume of 500 µL with phosphate buffer (50 mM NaCl, 100 mM Na(P03)4, pH 7.2). PEG (a mixture of NHrPEGsk-OCH3 and NHr PEGsk-maleimide or of NHrPEG$_5$k-OCH$_3$ and NHrPEG$_5$k-N$_3$) was dissolved directly (10× equivalent to COOH groups on surface of PS—COOH spheres), followed by excess sulfo-NHS (~5-6 mg), and excess EDC (~3-4 mg). The reaction was allowed to proceed for 4 hours at 25° C. Nanoparticles were purified by ultracentrifugation through a 100 kDa AmiconUltra 15 ml ultrafiltration device (Millipore) and washing with 15 ml of ultrapure water (3 washes total).

Maleimide-thiol or N$_3$-alkyne chemistry was performed to conjugate a thiol-modified or alkyne-modified ligand to the surface of the nanoparticle. Briefly, purified nanoparticles were mixed with modified ligand in phosphate buffer and allowed to react overnight under stirring at 4° C. Nanoparticles were purified from unreacted ligand via dialysis over 5 days using Float-a-Lyzer dialysis cassettes (1000 kDa MWCO, Spectrum Labs).

b. Biodegradable Polymers

The methods described below are ones using one polymer (poly(lactic-co-glycolic acid) or PLGA). This method can be used to generate ligand modified, brain penetrating particles with a variety of different hydrophobic polymers (e.g. other polyesters such as poly(lactic acid), polycaprolactone, as well as polyanhydrides and many others). Further, in certain embodiments, several other standard hydrophobic particle formulation techniques (e.g. single emulsion, double emulsion, salting-out, etc.) can be used. The ligand used could be a small molecule, antibody, antibody fragment, protein, nucleic acid, etc. The coupling chemistry between the particle/polymer and ligand can also be modified as needed based on the ligand.

Direct Conjugation to Polymer Prior to Particle Formulation (for Organic Solvent Soluble and Stable Ligands)

PLGA, PLGA-PEG, and PLGA-PEG-ligand were dissolved at 25 mg/ml in tetrahydrofuran (THF), along with a quantity of drug/therapeutic. Nanoparticles were formed by nanoprecipitation upon the addition of the THF solutions to stirred ultrapure water (or appropriate buffer to ensure ligand stability). Solvent (THF) was allowed to evaporate under stirring for two hours and nanoparticles were subsequently concentrated and washed three times with UP water via ultrafiltration with 100 kDa centrifugal filter units (Millipore).

Conjugation of Ligand to Particles after Particle Formulation (for Ligands that are not Soluble or Stable in Organic Solvents)

PLGA, PLGA-PEG, and PLGA-PEG-maleimide (or PLGA-PEG-azide) were dissolved at 25 mg/ml in tetrahydrofuran (THF), along with a quantity of drug/therapeutic. Nanoparticles were formed by nanoprecipitation upon the addition of the THF solutions to stirred ultrapure water (or appropriate buffer to ensure ligand stability). Solvent (THF) was allowed to evaporate under stirring for two hours and nanoparticles were subsequently concentrated and washed three times with UP water via ultrafiltration with 100 kDa centrifugal filter units (Millipore).

Maleimide-thiol or N3-alkyne chemistry was performed to conjugate a thiol-modified or alkyne-modified ligand to the surface of the NP. Briefly, purified NP are mixed with modified ligand in phosphate buffer and allowed to react overnight under stirring at 4° C. Nanoparticles were purified from unreacted ligand via dialysis over 5 days using Float-a-Lyzer dialysis cassettes (1000 kDa MWCO, Spectrum Labs).

Detailed Formulation of Targeted, Biodegradable TPNs—Hydrophilic Polymers Via Chelation The detailed method below uses one specific polymer (PGA) and one specific chelating agent/drug (cisplatin or CDDP). This method can be used to generate ligand modified, brain penetrating particles with a variety of different hydrophilic polymers with a high density of carboxyl acid side chains (e.g. hyaluronic acid and polyaspartic acid).

Polymer stock solutions were created by dissolving polymers in nuclease-free water (PGA, PGA-PEG, and PGA-PEG-azide). Nanoparticles were made by mixing an equal volume of polymer stock solutions with cisplatin (CDDP), or other chelating drug/molecule, stock solution (1.5 mg/ml CDDP in nuclease free water). After mixing, particles were allowed to self-assemble for 3+ days under continuous stirring at 45° C. After particle formation, particles were washed three times in ultrapure water and concentrated by ultrafiltration with 100 kDa centrifugal filters (Amicon® Ultra, Millipore).

N$_3$-alkyne chemistry was performed to conjugate an alkyne-modified ligand to the surface of the nanoparticle. Purified nanoparticles were mixed with modified ligand in dilute phosphate buffer and allowed to react overnight under stirring at 4° C. Nanoparticles were purified from unreacted ligand via dialysis over 5 days using Float-a-Lyzer dialysis cassettes (1000 kDa MWCO, Spectrum Labs).

Detailed Formulation of Targeted, Lipid- and Amphiphilic Block Copolymer-Based TPNs The detailed method below uses one specific phospholipid (DSPE) and one specific diblock copolymer (PBD-PEO). This method can be used to generate ligand modified, brain penetrating particles with a variety of different lipids or amphiphilic block copolymers. Further, several other standard drug encapsulation techniques (e.g., pH gradient, hydration, etc) can be used to encapsulate different drugs/therapeutics. The ligand used could be a small molecule, antibody, antibody fragment, protein, nucleic acid, etc. The coupling chemistry between the particle/polymer and ligand can also be modified as needed based on the ligand.

a. Liposome-Based Formulation 1,2-distearoyl-sn-glycero-3-phosphoethanolamine (DSPE) lipid was blended with DSPE-polyethylene glycol (DSPE-PEG-malemide or DSPE-PEG-azide; 5-10 wt %) in Methylene Chloride. Liposomes were formed by hydration/sonication in 1×PBS along with a quantity of drug/therapeutic at 65° C. for 1 h. A narrow size distribution of nanosized polymersomes was achieved with serial extrusion using a Liposofast Basic hand-held extruder equipped with 400, 200, 100, and 50 nm polycarbonate membranes (Avestin Inc., Ottawa, Ontario).

Maleimide-thiol or N3-alkyne chemistry was performed to conjugate a thiol-modified or alkyne-modified ligand to the surface of the liposomes. Purified liposomes were mixed with modified ligand in phosphate buffer and allowed to react overnight under stirring at 4° C. Liposomes were purified from unreacted ligand via dialysis over 5 days using Float-a-Lyzer dialysis cassettes (1000 kDa MWCO, Spectrum Labs).

b. Polymersome-Based Formulation

The PEO terminal hydroxyl end of the copolymer (PEO-b-PBD (PEO=polyethyleneoxide; PBD=polybutadiene); Polymer Source, Inc., Montreal, Quebec) was first modified with 4-fluoro-3-nitrobenzoic acid, succinimidyl carbonate, or carboxylic acid through an esterification procedure. The activated polymer was then precipitated using diethyl ether and purified using high performance liquid chromatography (HPLC). Targeting ligands were attached to the modified polymer through a nucleophilic aromatic substitution and/or via EDC/NHS reaction. Nonconjugated Tat was removed following polymersome formation by extensive dialysis in isotonic phosphate buffered saline (PBS), pH 7.4.

The selected polymer and drug/therapeutic (hydrophobic) were dissolved in methylene chloride and then deposited onto a roughened Teflon square and dried overnight under vacuum. 1×PBS along with a quantity of drug/therapeutic (hydrophilic) was then added to a glass vial containing the film; the vial was then sealed and allowed to sonicate at 65° C. for 1 h. A narrow size distribution of nanosized polymersomes was achieved with serial extrusion using a Liposofast Basic hand-held extruder equipped with 400, 200, 100, and 50 nm polycarbonate membranes (Avestin Inc., Ottawa, Ontario).

To formulate brain tissue penetrating 'coated nanoparticles' (CNPs), 100 nm carboxylate-modified polystyrene (PS—COOH) nanoparticles were covalently modified with methoxy-PEG5k-amine by EDC carbodiimide chemistry, following a modified protocol described previously [34, 33]. For protein quantification assay, CNPs were made with 100 nm non-fluorescent PS—COOH nanoparticles. For all other experiments, 100 nm red or blue fluorescent PS—COOH 'uncoated nanoparticles' (UNP) were used. Briefly, PS—COOH nanoparticles (1 mg) were mixed with methoxy-PEG5k-amine (10× equivalent to total COOH groups on surface of PS—COOH particles) in 100 mM phosphate buffer (pH 7.2, 150 mM NaCl), followed by addition of excess sulfo-NHS (~5-6 mg), and EDC (~3-4 mg) to a volume of 500 µL. Particle suspensions were placed on a rotary incubator and the reaction was allowed to proceed for 4 h at 25° C. After the reaction, particles were purified by ultracentrifugation (Amicon Ultra-15 mL 100 kDa MW cut-off) with ultrapure water (3 washes total). CNPs were resuspended in ultrapure water and stored at 4° C. until use.

For CNP-ITEM4 nanoparticles, a different proportion of PEG (methoxy-PEG5k-amine to malemide-PEG5k-amine) was used for initial particle PEGylation; specifically, 10 mol % and 50 mol % of maleimide-PEG5k-amine was used for CNP-ITEM4 (low) and CNP-ITEM4 (high) nanoparticles, respectively. ITEM4-SH was conjugated onto the surface of the nanoparticles containing maleimide-functionalized PEG by maleimide-thiol chemistry. Briefly, purified CNP-maleimide particles were mixed with ITEM4-SH (1.2× excess ITEM4-SH to maleimide) in 100 mM phosphate buffer (pH 7.2, 150 mM NaCl) and allowed to react overnight at 4° C. This reaction was performed immediately following nanoparticle PEGylation, as longer incubation times resulted in increased hydrolysis of the maleimide groups. After the reaction, nanoparticles were purified from unconjugated free ITEM4-SH via dialysis (1000 kDa Float-a-Lyzer dialysis cassettes) against 1×PBS for 5 days. The amount of ITEM4 molecules conjugated on CNP-ITEM4 nanoparticles was quantified via the LavaPep protein assay (Gel Company, San Francisco, Calif.) using ITEM4 as a standard. Nanoparticle samples were diluted to a concentration of ~100 ug/mL and assayed as per manufacturer's protocol.

Physicochemical Characterization of Nanoparticles

The physicochemical characteristics of nanoparticles were measured in 15× diluted PBS (~10 mM NaCl, pH 7.4) at 25° C. Hydrodynamic diameter and ζ-potential (surface charge) were determined by dynamic light scattering and laser Doppler anemometry, respectively, using a Zetasizer NanoZS (Malvern Instruments, Southborough, Mass.). Particle size measurement was performed at 25° C. at a scattering angle of 173° and is reported as the number-average mean. The zeta-potential values were calculated using the Smoluchowski equation and is reported as the mean zeta-potential.

Nanoparticle Binding to Fn14 Extracellular Domain

Nanoparticle binding affinities to Fn14 extracellular domain was evaluated by SPR using a Biacore 3000 instrument at 25° C. The Fn14 extracellular domain (Cell Sciences, Canton, Mass.) was conjugated to a CM5 Biacore chip, with three different Fn14 ligand RU values ranging from 50 to 300. The first flow path (Fc1) was activated and blocked with ethanolamine to serve as a reference for each binding run, as suggested per manufacturer's protocol. The running buffer was degassed 10 mM HEPES buffer (pH 7.4) containing 150 mM NaCl, 0.05% surfactant P-20 with 50 µM EDTA (HBS-P+). For SPR experiments, samples were run at a flow rate of 20 µL/min with an injection time of 3 min followed by a 2.5 min wait time for dissociation, before chip regeneration with either 100 mM phosphoric acid, pH 3 or 10 mM glycine, pH 1.75 (GE Healthcare). IgG isotype (25 nM) was used as a negative control and ITEM4 (25 nM) as a positive control. Nanoparticle binding was assayed with particle concentrations ranging between 1 µg/mL and 200 µg/mL diluted in running buffer. Data were analyzed using Biacore 3000 Evaluation Software, where data from Fc1 was subtracted from the Fc2, Fc3, and Fc4 data to give the final sensorgrams. Equilibrium binding affinities ($K_D$) were calculated as previously described [37].

Nanoparticle Binding to Brain Extracellular Matrix Proteins

Brain extracellular matrix (ECM) proteins were isolated from freshly collected mouse brain as previously described [38]. Briefly, resected whole mouse brain was frozen for at least 24 h at −80° C. and subsequently thawed and decellularized in a series of steps: ultrapure water (16 h at 4° C.), 0.02% trypsin/0.05% EDTA (1 h at 37° C.), 3% Triton-X 100 (1 h), 1.0 M sucrose (15 min), ultrapure water (15 min), 4% deoxycholate (1 h), 0.1% periacetic acid in 4% ethanol (2 h), 1×PBS (15 min), ultrapure water (15 min), and 1×PBS (15 min). The decellularized proteins were filtered (0.2 µm filter) to remove insoluble proteins and then frozen and stored at −80° C. until use.

The isolated mouse brain ECM proteins were conjugated to the second flow channel (Fc2) of a CM5 Biacore chip with ligand RU values ranging from 140 to 250. The first flow path was activated and blocked with ethanolamine to serve as a reference for each binding run. For binding experiments, samples were assayed at a flow rate of 20 μL/min with an injection time of 3 min followed by a 2.5 min wait time for dissociation, before chip regeneration with either 100 mM phosphoric acid, pH 3 or 10 mM glycine, pH 1.75 (GE Healthcare). Nanoparticle binding was assayed with particle concentrations ranging between 1 μg/mL and 200 μg/mL, diluted in running buffer.

Cell Culture

Human U87 glioblastoma cells that constitutively express firefly luciferase (U87-Luc) were provided by Dr. Andrew Kung (Columbia University Medical Center). In order to generate a GFP-positive U87-Luc cell line, pGIPZ lentiviral particles encoding TurboGFP (provided by Dr. Nhan Tran, TGen) were mixed with 8 μg/mL polybrene and added to subconfluent cultures of U87-Luc cells. Positively transduced cells were enriched by mass sorting the GFP-positive cells using a MoFlo flow cytometer (Dako, Carpinteria, Calif.). U87-Luc/GFP cells were cultured at 37° C. and 5% $CO_2$ in DMEM (Invitrogen Corp., Carlsbad, Calif.) supplemented with 10% fetal bovine serum (FBS, Invitrogen Corp.), 0.5 mg/mL G418, and 1% penicillin/streptomycin (Invitrogen Corp.). A mouse embryonic fibroblast (MEF) cell line generated from Fn14-null mice (MEF 3.5−/−) and a derivative stably transfected MEF 3.5−/− cell line expressing human Fn14 (MEF Fn14-V5) [39] were provided by Dr. Matthew Hayden (Columbia University Medical Center). Both cell lines were maintained at 37° C. and 5% $CO_2$ in DMEM supplemented with 10% FBS and 1% penicillin/streptomycin; the Fn14-V5 cell media also contained 10 ug/ml blasticidin.

Evaluation of Fn14 Expression in Cells

To examine Fn14 surface expression in the U87-Luc/GFP cell line, we performed flow cytometry analysis. Briefly, cells (~$10^6$) were incubated with no antibody, IgG isotype, or ITEM4 for 30 min on ice. Next, cells were washed 3 times with FACS buffer and a fluorescent secondary antibody (anti-mouse IgG-APC) was added and allowed to incubate for 15 min. After washing 3 times in FACS buffer, cells were assayed for APC mean fluorescence intensity using a FACSCalibur flow cytometer (Becton Dickinson, Franklin Lake, N.J.). Data from 10,000 events were gated using forward and side scatter parameters to exclude dying cells and debris.

Fn14 expression in the two MEF cell lines, MEF 3.5−/− and MEF Fn14-V5, was determined using both Western blot and flow cytometry analyses. For Western blotting, cells were harvested by scraping and lysed in 20 mM HEPES, 150 mM NaCl, 1.5 mM $MgCl_2$, 10% glycerol, and 1% Triton X-100 supplemented with a protease inhibitor cocktail (Sigma-Aldrich, St. Louis, Mo.) and two phosphatase inhibitor cocktails (Calbiochem, Billerica, Mass.). The protein concentration of each lysate was determined by BCA protein assay (Pierce Protein Biology, Rockford, Ill.). Equal amounts of protein were subjected to SDS-PAGE (Life Technologies, Grand Island, N.Y.) and electrotransferred to PVDF membranes (Millipore, Billerica, Mass.). Membranes were blocked in 5% non-fat dry milk (NFDM) in TBST buffer and then sequentially incubated with either an anti-Fn14 antibody (Cell Signaling Technology, Danvers, Mass.) or an anti-tubulin antibody (Sigma-Aldrich, St. Louis, Mo.) and then horseradish peroxidase (HRP)-conjugated secondary antibody (Cell Signaling Technology, Danvers, Mass.). The membranes were washed in TBST and then immunoreactive proteins were detected using the Amersham Enhanced Chemiluminescence Plus kit (GE Healthcare, Piscataway, N.J.) according to the manufacturer's instructions. For flow cytometry, MEFs (~$10^6$) were incubated with Mouse Fc Bloc (BD Biosciences, San Jose, Calif.) for 15 min and then incubated with: no antibody, IgG isotype-APC, or ITEM4-APC for 30 min on ice. Cells were then washed 3 times with FACS buffer and then assayed for APC mean fluorescence intensity by flow cytometry as described above.

Nanoparticle Uptake in Fn14-Positive and Fn14-Negative Cells

Nanoparticle uptake in the MEF 3.5−/−, MEF Fn14-V5, and U87-Luc/GFP cell lines was determined via flow cytometry. Briefly, cells were plated in 24-well plates at a seeding density of $10^5$ cells per well. Cells were allowed to attach overnight and the following day the media was replaced with serum-free DMEM along with nanoparticles (2 μg per well). Cells were incubated with nanoparticles for 1 h, washed 3 times with 1×PBS, detached with trypsin, and diluted in cold 1×PBS for flow cytometry analysis. Mean fluorescence intensity was analyzed using a BD LSR Fortessa flow cytometer (Becton Dickinson, Franklin Lake, N.J.). Data from 10,000 events were gated using forward and side scatter parameters to exclude dying cells and debris.

Nanoparticle Internalization in Fn14-Positive GBM Cells

The internalization of CNP-ITEM4 in U87-Luc/GFP cells was confirmed by live-cell confocal microscopy at 37° C. and 5% $CO_2$. Briefly, cells were seeded between 2.0 to 2.5×$10^3$ cells per plate onto Lab-Tek glass-bottom culture plates and incubated overnight at 37° C. After overnight incubation, culture medium was replaced with fresh media before nanoparticles (2 μg per well) were added. Prior to imaging, the U87-Luc/GFP cells were treated for 15 min with Hoechst 34580 (5 μg/ml) to stain the nucleus. Following incubation, cells were washed 3 times with 1×PBS and replaced with Opti-MEM (Invitrogen Corp., Carlsbad, Calif.). Cells and nanoparticles were then imaged under a Zeiss LSM510 Meta confocal microscope (Carl Zeiss Inc., Thornwood, N.Y.) using a 63× Plan-Apo/1.4 NA oil-immersion lens. For multi-color microscopy, samples were excited with 405, 488, 543 and 633 nm laser lines, and images were captured by multi-tracking to avoid bleed-through between fluorophores.

Nanoparticle Transport in Rat Brain Slices

The diffusion of individual fluorescent nanoparticles in rat brain slices was quantified via multiple particle tracking (MPT) as previously described [34]. Briefly, Sprague-Dawley rats (6-8 weeks) were euthanized, the brain was harvested and incubated in artificial cerebrospinal fluid (aCSF, Tocris Bioscience, Bristol, UK) for 10 min on ice. Brain was sliced into 1.5 mm coronal sections using a Zivic brain matrix slicer (Zivic Instruments, Pittsburgh, Pa.). Slices were added to custom microscope slide chambers and fluorescent nanoparticles were injected (0.5 μL of 20 μg/mL stocks) into the middle of cortical tissue. Slides were sealed with super glue and allowed to incubate at room temperature for a minimum of 15 min before imaging. The movement of individual nanoparticles in brain slices was imaged, at a frame rate of 15 frames/s for a total of 300 frames (20 s), using an inverted epi-fluorescence microscope (Axiovert D1, Zeiss, Thornwood, N.Y.) with a 100×/1.46 NA oil-immersion objective equipped with an Evolve 512 EMCCD camera (Photometrics, Tucson, Ariz.). Movies were analyzed using a custom written MATLAB automated tracking code to extract x, y-coordinates of nanoparticles over time, as previously described [40]. At least three rat brains were imaged per each nanoparticle type with at least 100 particles tracked per sample. The geometric mean of the mean squared displacement (MSD) was calculated per sample and the average of different rodent brains was calculated as a function of time scale [40, 41].

Intracranial Implantation of U87-Luc/GFP Tumors

All animal procedures were approved by the University of Maryland Institutional Animal Care and Use Committee (IACUC) and the Office of Animal Welfare Assurance (OAWA). Athymic nude mice (age, 6-8 weeks) were purchased from the University of Maryland School of Medicine Veterinary Resources. For the tumor implantation procedure, animals were anesthetized via continuous flow of 2 to 3% isoflurane through a nose cone. Using a stereotactic frame and sterile technique, ~4.0×10$^5$ U87-Luc/GFP GBM cells were injected at a rate of 1 µL/min over 5 min into the left frontal lobe of the brain through a burr hole; drilled 2 mm lateral to the sagittal suture and 1 mm anterior to the coronal suture at a depth of 3 mm below the dura. Mice were given the analgesic buprenorphine (Buprenex, 0.05 mg/kg, subcutaneously) after the surgery. Animals were observed daily for any signs of deterioration or neurological dysfunction. If the symptoms persisted and resulted in debilitation, animals were euthanized according to protocol.

In Vivo Bioluminescence Imaging

Intracranial U87-Luc/GFP mouse tumors were imaged using a Xenogen IVIS system (Caliper Life Sciences, Hopkinton, Mass.). Anesthesia was induced in an induction chamber with 2.5% isoflurane in 100% oxygen at a flow rate of 1 L/min and maintained in the IVIS system with a 2.0% mixture at 0.5 L/min. The mice were injected with D-luciferin (150 mg/kg, intraperitoneally; dissolved in PBS) and returned to their home cages. Ten minutes following the D-luciferin injection, anesthesia was induced with isoflurane in an induction chamber. The animal was moved to the IVIS imaging chamber and maintained on 2 to 3% isoflurane. Photons emitted from live mice were acquired as photons/s/cm$^2$/steradian (p/s/cm$^2$/sr) and analyzed using LivingImage software (PerkinElmer, Mass.).

Intracranial Injection of Nanoparticles

At day 7 after the implantation of U87-Luc/GFP tumor cells, bioluminescent signal from the engrafted brain tumors was confirmed in each animal. Once tumor signal was confirmed, the animals were anesthetized as described above and nanoparticles suspended in normal saline were administered sterilely into mouse brain (n=3) through the same burr hole using a stereotactic frame. CNP and CNP-ITEM4 (high) nanoparticles in normal saline were loaded into a sterile 30-gauge Hamilton syringe needle, lowered to a depth of 3.5 mm, and injected slowly: 5 µl (0.1 mg/ml nanoparticles) at a rate of 1 µl/min over 5 min.

Nanoparticle Distribution in the Brain and Intracranial Human GBM Xenograft

The distribution and co-localization of fluorescent nanoparticles with U87-Luc/GFP tumors in the brain was evaluated by imaging brain cryosections. The animals were euthanized with an overdose of isoflurane 24 h after the injection of nanoparticles. The euthanized animals were perfused with 30 mL of 1×PBS after which the brains were carefully removed, embedded in Optimal Cutting Temperature (OCT), and stored at −80° C. A cryostat (Leica CM3050 S) was used to cut serial 10 µm sagittal brain sections and mounted on positively charged microscope slides. The brain sections were stained with Prolong Gold antifade with or without DAPI (Invitrogen, Carlsbad, Calif.), sealed with coverslips, and imaged for cell nuclei (dark blue), CNPs (light blue), GFP-positive U87 tumors (green), and CNP-ITEM4 (high) nanoparticles (red) using a Nikon epifluorescence microscope under 10× and 20× magnification. High resolution stitched images (6×6) were obtained by using the montage imaging feature in the Nikon NX 2 software. Microscope settings were carefully optimized to avoid background fluorescence based on non-injected control mouse brains, where the exposure time for each channels were kept constant throughout the study.

Nanoparticle Biodistribution and Tumor-Specific Targeting to Breast Tumor Xenograft Following Systemic Administration Individual female Nu/Nu mice (6-8 weeks old) was injected with MDA-MB-231/Luc Ctrl and MDA-MB-231/Luc Fn14 shRNA 448 cells in the left and right flank, respectively (lx 10$^6$ cells each). Tumor growth was monitored by bioluminescence imaging (BLI) and caliper measurements. When each tumor reached ~100 mm$^3$ in volume, near infrared (NIR)-labeled non-targeted coated nanoparticles (CNPs) or ITEM4-CNPs were administered via the tail vein. At 72 hours after injection, the mice were euthanized and dissected. Blood, organs (heart, liver, spleen, kidney, lung, stomach, intestine, uterus, skin, muscle, bone, brain), and tumors were isolated and placed on a petri dish and assessed for biodistribution and tumor targeting capabilities by quantitative optical imaging.

Statistical Analysis

Statistical analysis of data was performed by a two-tailed Student's t test assuming unequal variances or one-way analysis of variance (ANOVA) followed by Tukey HSD or Games-Howell tests using SPSS 18.0 software (SPSS Inc., Chicago, Ill.). Differences were considered to be statistically significant at a level of P<0.05.

Example 2: BPNs

Previous studies suggested that the mesh spacing in brain ECS is no larger than ~20-40 nm, and a restricted movement of 35 nm polyethylene glycol (PEG)-coated quantum dots (QD) has been shown in rat brain [17, 26]. It was hypothesized that poor penetration of PEG-coated QD was due to adhesive interactions between the QDs and the ECM owing to inadequate coating of PEG on the QD surfaces. However, drawing on experience with mucus-penetrating particles [28], densely coated 40-200 nm polystyrene (PS) particles with low molecular weight PEG, were injected into rat brains, and then visualized particle spread. Uncoated PS nanoparticles did not penetrate, whereas dense PEG-coated PS penetrated >100 µm beyond the injection site within just 1 h. (FIG. 1). These highly dense PEG coated particles are referred to as "brain-penetrating nanoparticles" (BPN) and the non-coated counterparts "uncoated nanoparticles" (UCN).

Example 3: Fn14 is Highly Expressed by Invading GBM Cells

Figure 2B:
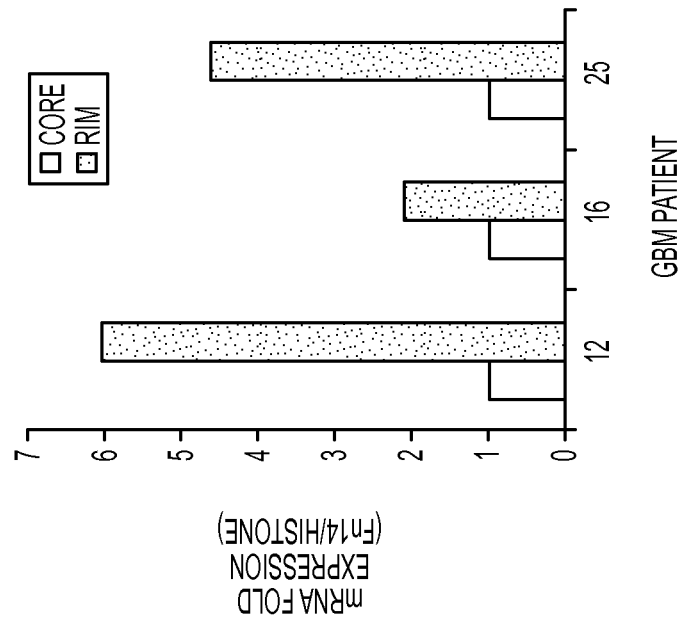
FIG. 2A is a photograph illustrating the approach used to generate the data in FIG. 2B, showing that Fn14 mRNA expression is higher in actively invading glioma cells compared to stationary core cells, according to an embodiment.
Figure 2A:
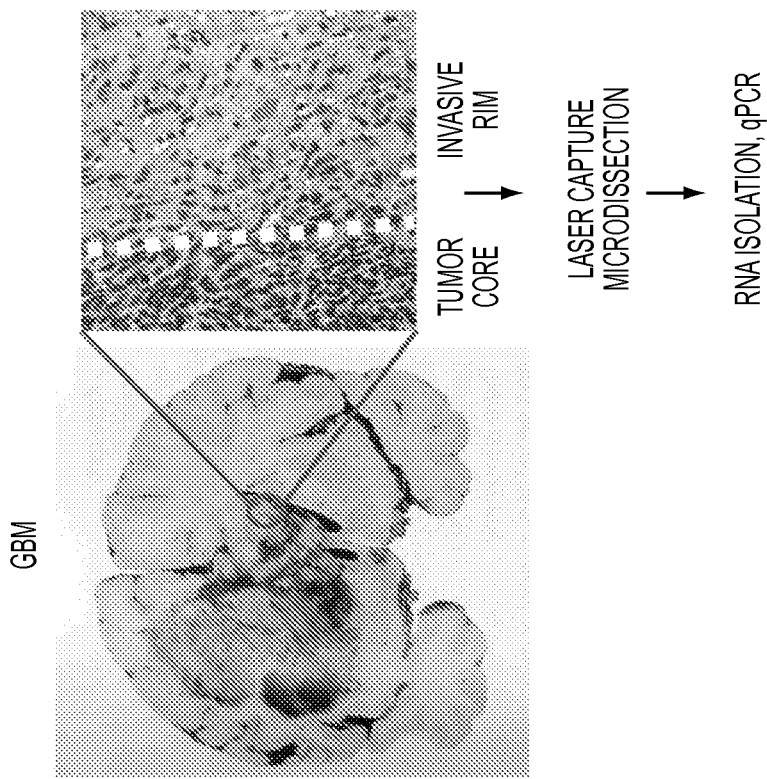

Fn14 is minimally expressed in normal human brain but highly expressed in high-grade gliomas with more malignant and invasive characteristics. Furthermore, high Fn14 expression correlates with poor patient outcome [12]. These findings suggest a major role for Fn14 in the pathobiology of GBM. Fn14 is overexpressed in GBM cells invading the normal brain parenchyma [12,13] (FIG. 2). In FIG. 2A, hematoxylin and eosin staining of the edge of a malignant glioma biopsy specimen shows the dense cellular tumor core and the infiltrating tumor cells at the rim of the tumor. Laser capture microdissection at the tumor edge in FIG. 2B followed by RNA isolation and quantification of Fn14 mRNA levels using real time quantitative polymerase chain reaction [rtPCR] shows significantly increased expression in the invasive cells. Forced Fn14 overexpression in glioma cells stimulated both cell migration and invasion, suggesting that tumor cells with the highest levels of Fn14 on their surface may also have the greatest invasive capacity [12]. These findings differentiate Fn14 from other GBM targets (i.e., EGFR, IL13R, Tenascin C) and indicate that Fn14 may be an ideal surface molecule for targeting invasive, malignant glioma cells.

Example 4: Fn14-Targeted BPNs Show Strong Fn14 Specific Binding, Minimal ECM Non-Specific Binding, Improved Glioblastoma Cell Uptake, and Unchanged Brain Diffusion Data demonstrate that BPNs conjugated to the anti-Fn14 monoclonal antibody ITEM4 bind to immobilized Fn14 but not brain ECM components. In FIG. 3A, SPR analysis measures the binding to the Fn14 receptor: free ITEM4 monoclonal antibody, BPNs with varying surface densities of ITEM4, and non-targeted BPNs. In FIG. 3B, SPR analysis measures the binding of uncoated polystyrene NPs and BPNs with varying surface densities of ITEM4 to mouse brain ECM. The brain ECM SPR chip was validated using monoclonal antibodies recognizing several common brain ECM components. FIG. 3C illustrates human U87 glioma cells treated with fluorescent BPN or ITEM 4 conjugated BNP. ITEM4 conjugation (high density) resulted in a ~4.5-fold increase in BPN binding to glioma cells in culture as measured by multiple particle tracking (MPT), a method that was developed to quantify the non-convective movement of hundreds of individual nanoparticles in brain ECS using in vivo imaging (FIG. 3C). Most importantly, ITEM4 conjugation to the BPN surface does not appear to inhibit the movement of BPNs in brain tissue (FIG. 3D).

Figures 4A, 4B, 4C:
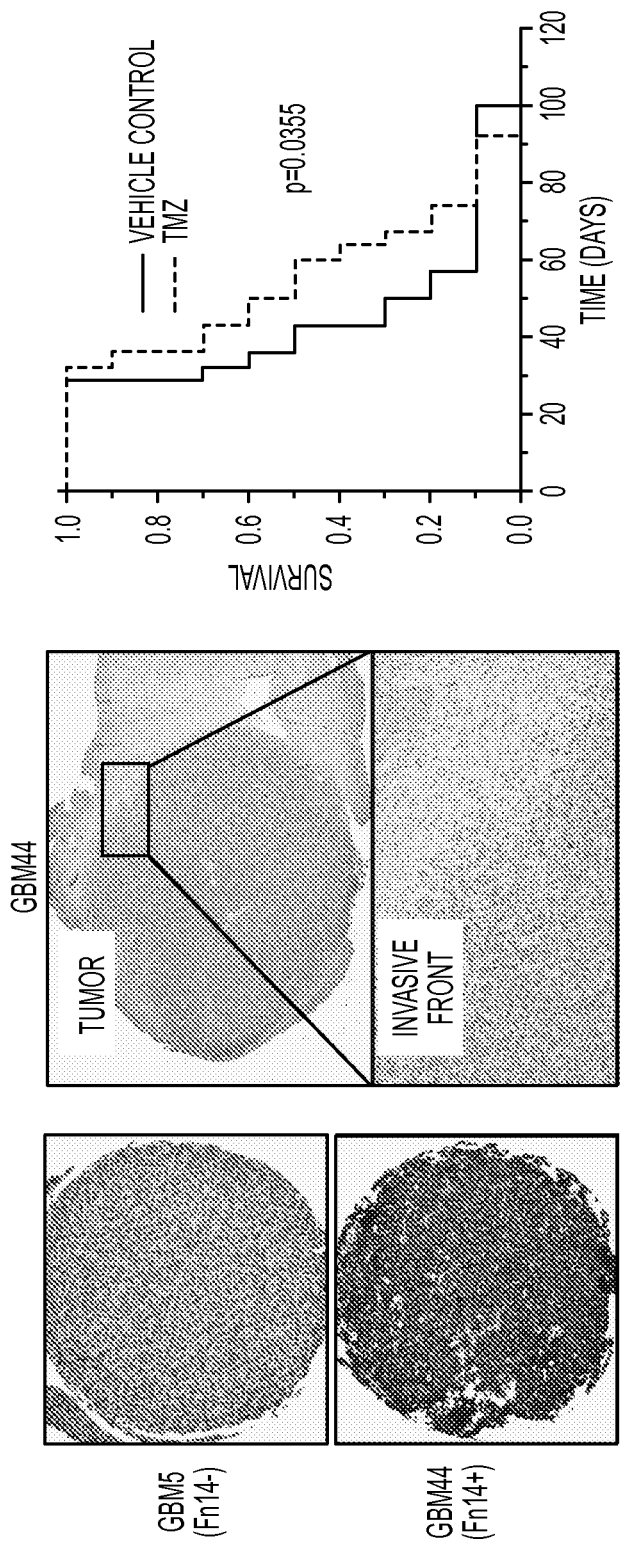
FIG. 4A-4B are photographs illustrating the Fn14+ GBM44 PDX model where (A) immunohistochemical staining for Fn14 occurs in PDX tumors, GBM44 (Fn14+) but not GBM5 (Fn14−), (B) coronal brain section of GBM44 tumor with enlarged view of the invasive rim showing invading human GBM cells.
FIG. 4C is a graph showing modest efficacy of TMZ in GBM44 PDX model, according to an embodiment.

Example 5: Patient-Derived GBM44 Cells Show High Fn14 Expression, Brain Invasion, and TMZ Sensitivity To assess if BPNs (with or without Fn14 targeting) will enable improved delivery and efficacy in a translationally-relevant human GBM model, a well-characterized Fn14+, patient-derived GBM cell line named GBM44 was used. This PDX model was initially generated by the immediate transfer of tumor tissue into immunodeficient mice and has been passaged over time as a subcutaneous tumor. GBM PDX models maintain histologic and genetic characteristics of the original patient tumor during in vivo passaging. Furthermore, the invasive nature of human GBM cells is recapitulated in PDX xenograft models. The GBM44 PDX line expresses high levels of Fn14 (FIG. 4A) and after intracranial injection it invades the normal brain parenchyma (FIG. 4B). The Fn14+ GBM44 PDX tumor is also susceptible to treatment with temozolomide (TMZ) (FIG. 4C), suggesting that the model system has significant translational relevance.

Example 6: Analysis of Fn14 Expression in Human Glial Tumors

Figure 5B:
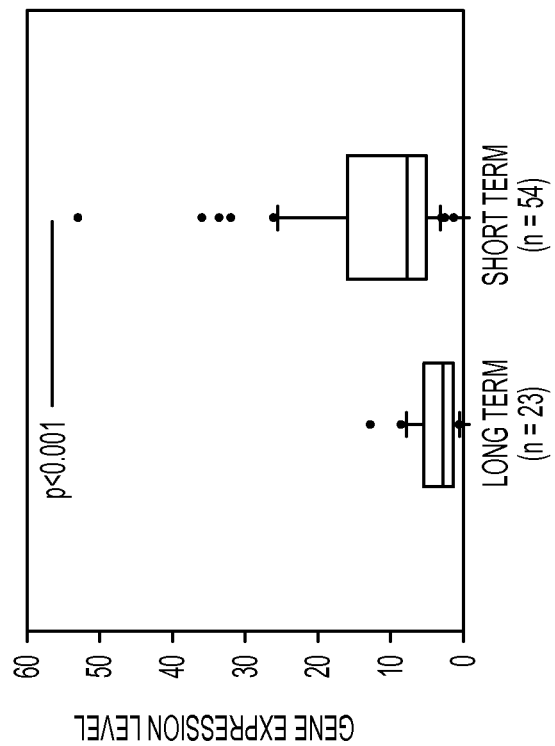
FIG. 5A-5B are graphs illustrating analysis of Fn14 mRNA expression in human glial tumors. (A) expression levels of Fn14 mRNA in 184 normal and brain tumor specimens and (B) expression values of Fn14 mRNA were analyzed in two patient survival clusters, according to an embodiment.
Figure 5A:
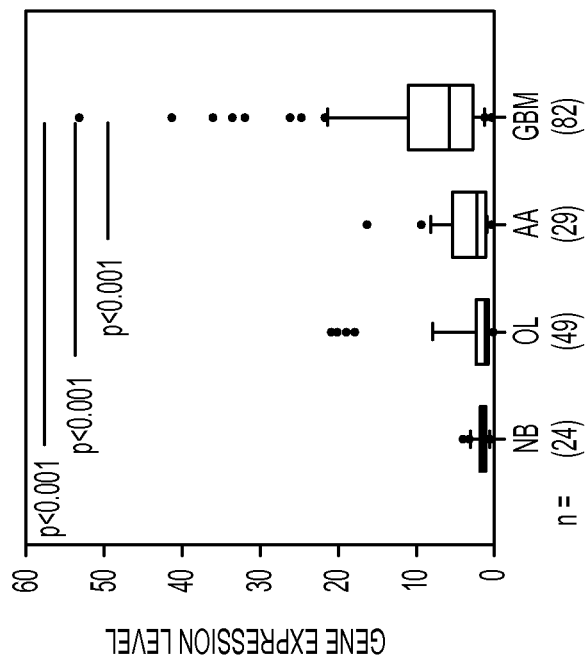

Increasing Fn14 expression correlates with higher glioma grade and shorter survival time [12]. The Fn14 transcript levels were analyzed in the glioma specimens and normal tissue from epilepsy cases. The data were also compared based on survival times by categorizing patients into two groups: short term and long-term survival. This analysis showed the patients with high Fn14 expression GBMs did not live as long. The results also confirmed the hypothesis that increasing Fn14 expression is found in higher grade gliomas with more malignant and invasive characteristics. In FIG. 5A-5B, analysis of Fn14 expression in human glial tumors revealed (A) expression levels of Fn14 mRNA in 184 normal and brain tumor specimens. GBM showed significantly higher Fn14 expression levels compared to either nonneoplastic brain (NB), oligoastrocytoma (OL), or anaplastic astrocytoma (AA) and (B) expression values of Fn14 mRNA were analyzed in two clusters. Cluster One had a survival mean of 401 days (short-term survival) and Cluster Two had a survival mean of 952 days (long-term survival). Fn14 expression levels were significantly higher in the short-term survival cluster.

Example 7: Delivery Systems Including Polymeric Nanovectors Mediate Efficient Gene Transfer to Glioma Cells and Tumors Polymeric nanogene vectors designed to protect DNA in vivo were engineered to enable efficient cellular trafficking and transgene expression. The ability to knockdown a model gene in brain tumors was tested. Nanovectors containing Luciferase shRNA plasmid were directly applied to luciferase-expressing glioma cells in culture and to intracranial tumors (FIG. 6A-C). Nanovectors efficiently entered cells and silenced the tumor-specific transgene (luciferase) in vitro and in vivo. Specifically, nanovectors efficiently (A) entered mouse glioma cells [GL261] and after entering the cells, (B) nanovectors effectively delivered a plasmid gene construct with green fluorescent reporter and inhibitory RNA for luciferase (shLuc) to GL261 cells that constitutively express luciferase GL261L. In FIG. 6C, BLI of GL261L cells in vivo show significant BLI silencing using nanovectors carrying shLuc plasmid (dotted line).

Example 8: Fn14 is Highly Expressed on Glioma Cell Lines

Figure 7:
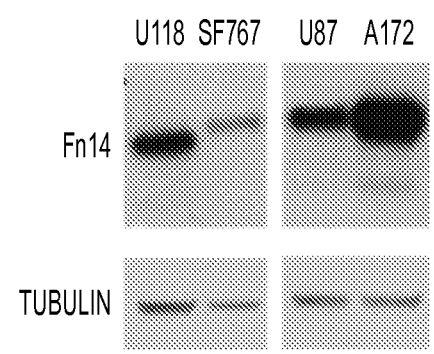
FIG. 7 is a Western blot image illustrating Fn14 expression in several GBM cell lines, according to an embodiment.

To confirm elevated Fn14 gene expression in model glioma cell lines, Fn14 mRNA levels were assessed in FIG. 7. FIG. 7 is a Western blot that illustrates Fn14 is expressed in GBM cell lines. Total cell lysates were prepared from various GBM cell lines and equal amounts of protein were immunoblotted with anti-Fn14 and anti-tubulin antibodies. Highest Fn14 expression occurred in the A172 cell line.

Example 9: Formulation of PEI-Based BPN Gene Vectors

PEG-PEI nanoparticles were formulated as previously described. [42]. For PEG-PEI particles with targeting ligands, hetero-bifunctional PEG, Malemide-PEG-Succinimidyl Carboxy Methyl ester was first conjugated to branched PEI, followed by ligand conjugation through the thiol-malemide linkage. Ligands for this conjugation step may include: TWEAK and Fn14 monoclonal antibody or antibody fragments. Particle types may include PEG-PEI, PEG Dendrimer, and PEG CK30. Formulation variables include polymers (PEI, PEI-PEG, Dendrimer-PEG, and CK30-PEG. PEG may have a coating density MW of 5 kDa to 10 kDa. Polymer concentrations and solvents and surfactants are readily available and known in the art.[43]-[44] Characterization methods can include dynamic light scattering (size and net surface charge), electron microscopy (morphology and size confirmation) and fluorometric binding assays and confocal microscopy (quantification of PEG density). Particle transport rates were measured by analyzing trajectories of fluorescent particles, recorded by using a silicon-intensified target camera (Strome/Hanes Labs) mounted on an inverted epifluorescence microscope. MPT analysis in brain tissue was performed as previously described. [34], Low passage Fn14+U118 glioma cells were grown in glass chambers. Targeted BPN gene vectors containing a GFP reporter plasmid were added to cells and incubated. Confocal microscopy was used to assess cell morphology (toxicity) and count GFP+ cells per high power field (HPF) to compare transfection rates. Cells were trypsinized and flow cytometric analysis used to quantify the percent GFP+ transfection for each treatment group.

Figure 8A:
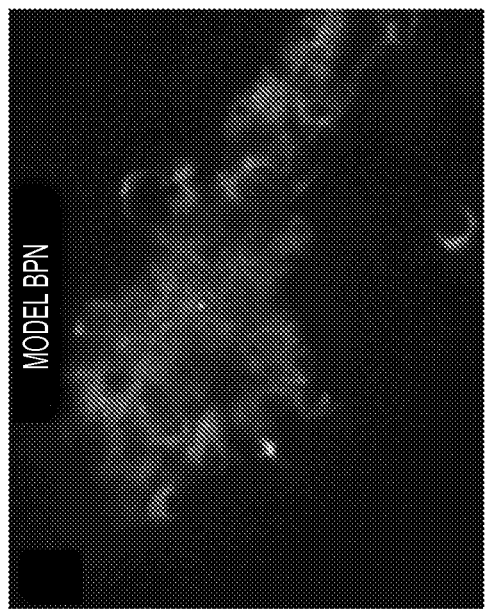
FIG. 8A-8D are photographs illustrating BPN gene vectors showing similar in vivo brain distribution as optimized model BPN. (A) Conventional uncoated nanoparticles injected directed into the living mouse brain show minimal diffusion or transport. (B) Optimized model BPN rapidly distribute within the mouse brain. (C) BPN gene vectors also penetrate well in brain tissue. (D) Overlay of model BPN and BPN gene vectors shows a close overlap of the two particle types, according to an embodiment.
Figure 8B:
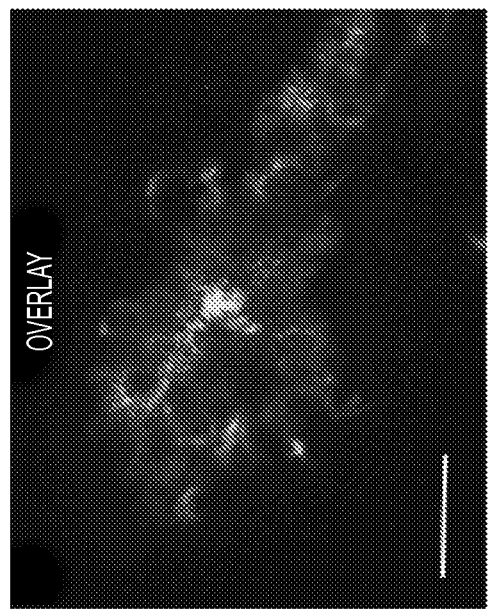
Figure 8C:
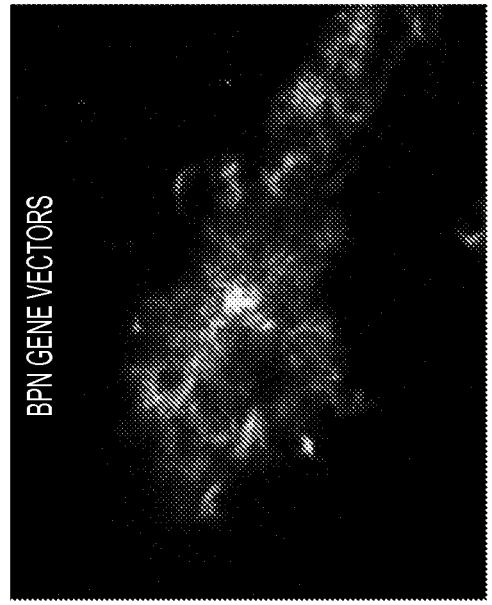
Figure 8D:

Example 10: Distribution and Reporter Gene Transfer Via BPNs to Invading Fn14+ Human Glioma Cells in an Organotypic Brain Slice Migration Assay Gene vectors were formulated with brain penetrating characteristics using 5K PEG-PEI diblock polymers and fluorescently labeled plasmid DNA. These particles were then co-injected with model BPN in the living mouse brain (FIG. 8). In FIG. 8A, conventional, uncoated nanoparticles were injected into the living mouse brain showing minimal diffusion or transport. Optimized model BPN in FIG. 8B rapidly distributes within the mouse brain. In FIG. 8C, BPN gene vectors also penetrated well in brain tissue. An overlay in FIG. 8D shows model BPN and BPN gene vectors having a close overlap of the two particle types.

Laser scanning microscopy was used to image the particle spread using an in vivo, closed cranial window mouse system. This showed a nearly exact distribution overlap of the gene vectors and model BPNs. Fluorescently-labeled BPN PEG-PEI gene vectors were also analyzed ex vivo in fresh brain slices using MPT (data not shown). This analysis correlated well with the in vivo imaging comparison shown here. These preliminary results suggested the ability to successfully make BPN gene vectors using a well-known and characterized polymeric gene vector system.

Figure 9:
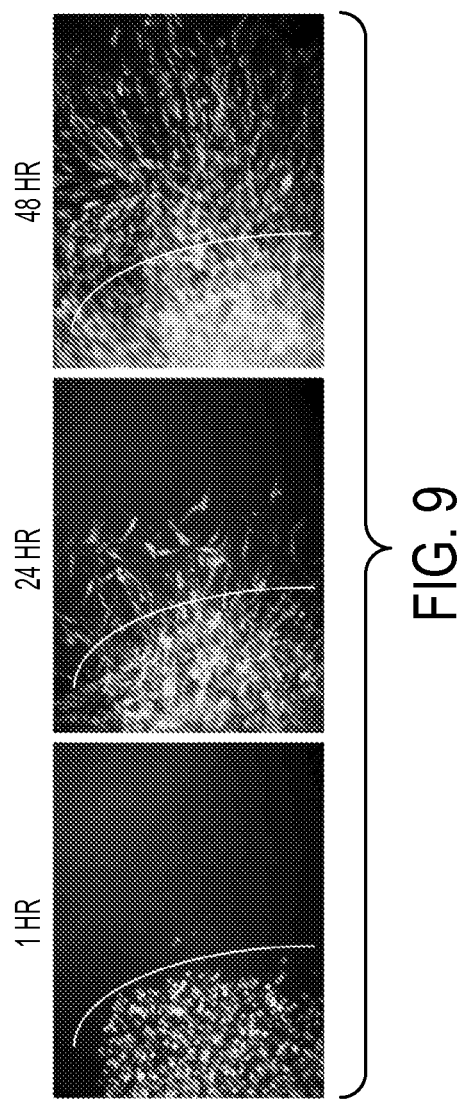
FIG. 9 are photographs illustrating the brain slice invasion assay featuring green fluorescence protein ("GFP")—labeled human glioma cells after 1 hour, 24 hours, and 48 hours incubation, according to an embodiment.

Example 11: Green Fluorescent Protein Expressing Fn14+ Human Glioma Cells Invade in Fresh Brain Slices An ex vivo brain slice migration assay was developed using GFP+, Fn14+ human glioblastoma cells (U118) and fresh mouse brain in organotypic culture conditions. FIG. 9 shows photographs of U118 GFP+ cells placed on fresh mouse brain slices and incubated for 1, 24, and 48 hours. For this analysis, C57BL/6 mice were euthanized with isofluorane and cervical dislocation. The brain was removed and 400 μm thick slices (6-8/mouse) were cut using a vibratome. The slices were then placed on top of a transwell membrane chamber full of cell culture media (DMEM). GFP+U118 cell suspension was placed on top of each brain slice, then incubated for 24-48 hr. Quantitation involved brief fixation then confocal microscopy using Volocity Image software to calculate depth of invasion of GFP+ cells. The above brain slice migration assay was set up and nanoparticles (plasmid dsRED reporter) was mixed with the GFP+U118 cells at the time of placement on the brain slice. Imaging analysis included confocal microscopy with distance measurements and qualitative assessments of particle locations, cell locations, and cell transfection. The tissue was digested to create a signal cell suspension.

Example 12: Synthesis and Characterization of Fn14-Targeted Nanoparticles

Figure 10A:
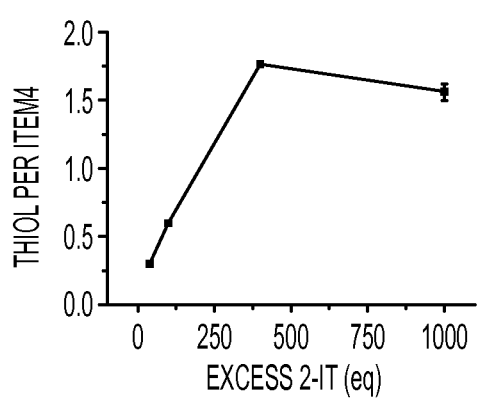
FIG. 10A-10B are graphs showing reaction conditions for the optimization of (A) thiol-modification of ITEM4 and (B) surface density of ITEM4 for coated nanoparticles ("CNP")—ITEM4 nanoparticles, according to an embodiment.
Figure 10B:
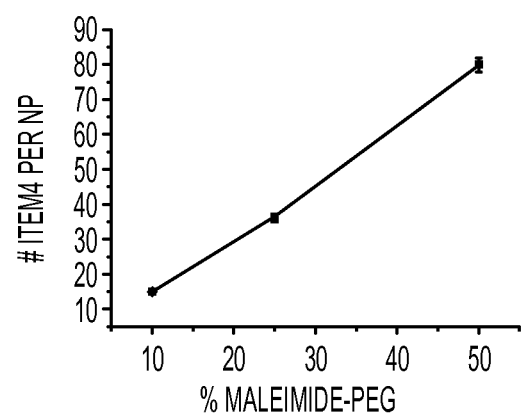

A variety of polystyrene (PS)-based brain tissue penetrating 'coated nanoparticles' (CNPs) that were surface-functionalized were synthesized with a well-characterized antibody, ITEM4, that binds strongly to Fn14. Reaction conditions, including the molar excess of 2-iminothiolane to ITEM4 and the ratio of malemide-PEG5k-amine to methoxy-PEG5k-amine, were optimized to produce CNPs with different surface densities of ITEM4 (FIG. 10A-10B). The quantification of ITEM4 thiolation and ITEM4 surface density was measured by thiol quantification assay kit and LavaPep Protein Assay, respectively.

Three sets of PEG-coated nanoparticles: no ITEM4 (CNP), decorated with a low density of ITEM4 (CNP-ITEM4 (low)), or decorated with a high density of ITEM4 (CNP-ITEM4 (high)) were compared with conventional, uncoated nanoparticles (UNP) (Table 2).

TABLE 2

Physicochemical properties of nanoparticles.

| Formulation | Particle Diameter, (nm) [a] | ζ-potential, (mV) [b] | Surface density of ITEM4, (#/particle) [c] |
|---|---|---|---|
| UNP | 95 ± 3 | −54.6 ± 3.0 | — |
| CNP | 113 ± 2 | −7.0 ± 0.2 | — |
| CNP-ITEM4 (low) | 113 ± 3 | −8.7 ± 1.2 | ~11 |
| CNP-ITEM4 (high) | 114 ± 22 | −8.9 ± 0.7 | ~56 |

[a] Diameter (number mean) measured by dynamic light scattering. Data represents the average of 3 independent experiments +/− SD.
[b] Measured at 25° C. in 15X diluted PBS, pH 7.4. Data represents the average of 3 independent experiments +/− SD.
[c] Surface density reported from LavaPep fluorescent protein assay.

CNP, CNP-ITEM4 (low) and CNP-ITEM4 (high) exhibited larger hydrodynamic diameters and more near neutral ζ-potential compared to UNP, as expected for nanoparticles with dense PEG coatings. CNP-ITEM4 (low), and CNP-ITEM4 (high) displayed a slightly more negative surface charge compared to CNP. The number of ITEM4 molecules was quantified on the surface of nanoparticles and it was determined that there were ~11 and ~56 ITEM4 molecules per particle for CNP-ITEM4 (low) and CNP-ITEM4 (high) nanoparticles, respectively.

Example 13: Biacore Screening of Nanoparticles for Fn14 Binding

Figure 11A:
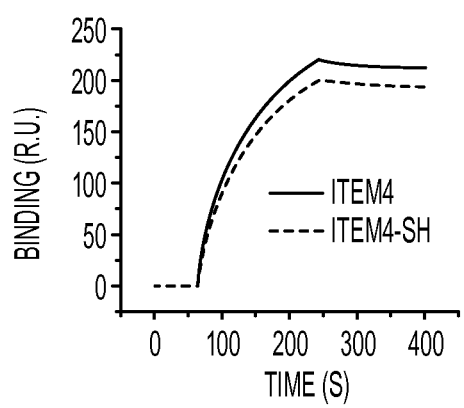
FIG. 11A-11B are graphs illustrating SPR analysis measuring ITEM4 antibody and nanoparticle binding to the Fn14 extracellular domain (A) free ITEM 4 and thiol-modified ITEM4 (ITEM4-SH) and (B) CNP and CNP-ITEM4 nanoparticles with two different surface densities of ITEM4, according to an embodiment.
Figure 11B:
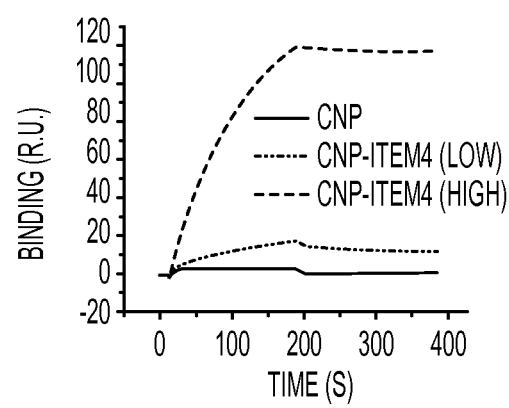

To test the ability of CNP-ITEM4 nanoparticles to bind Fn14, the Fn14 extracellular domain was functionalized to the surface of a Biacore chip. SPR analysis was used to measure antibody and nanoparticle binding to the Fn14 extracellular domain: FIG. 11A illustrates free ITEM4 and thiol-modified ITEM4 (ITEM4-SH) and FIG. 11B illustrates CNP and CNP-ITEM4 nanoparticles with two different surface densities of ITEM4. The binding of ITEM4 (unmodified), ITEM4-SH (thiol-modified for surface conjugation to nanoparticles), and CNP formulations was measured with different surface densities of ITEM4. ITEM4 and ITEM4-SH bound similarly, indicating that thiol-modification of ITEM4 does not significantly affect the binding activity of ITEM4 to Fn14 (FIG. 11A). CNP exhibited no appreciable Fn14 binding, whereas both CNP-ITEM4 (low) and CNP-ITEM4 (high) displayed significant Fn14 binding on the chip (FIG. 11B).

Figure 12A:
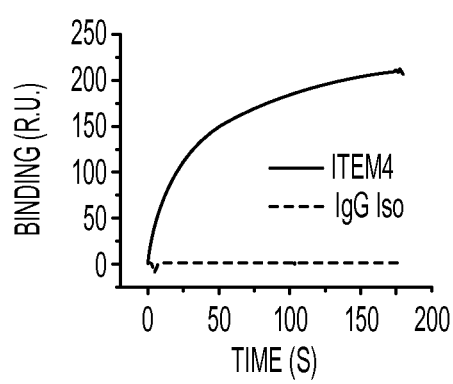
FIG. 12A-12B are graphs illustrating specificity of CNP-ITEM4 (high) binding to Fn14 Biacore chip. SPR showing (A) blocking of available Fn14 binding sites with excess ITEM4 (500 nM), (B) Binding of CNP-ITEM4 (high) to Fn14 Biacore chips pretreated with either excess IgG isotype control (500 nM) or ITEM4 (500 nM), according to an embodiment.
Figure 12B:
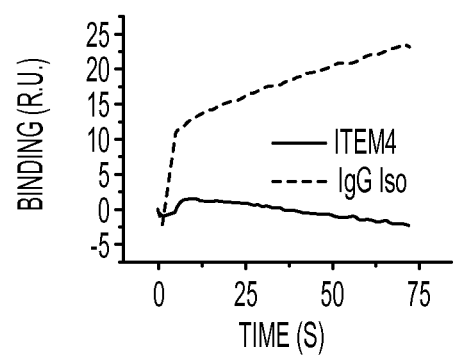
Figure 13A:
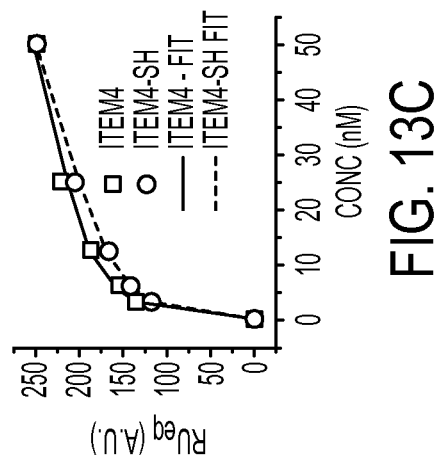
FIG. 13A-13C are graphs illustrating SPR analysis of ITEM4 binding to Fn14 according to an embodiment.
Figure 13B:
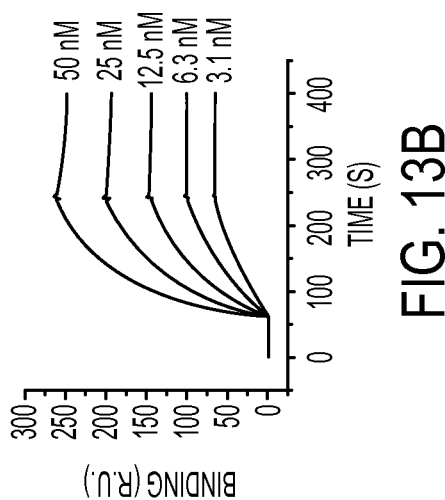
Figure 13C:
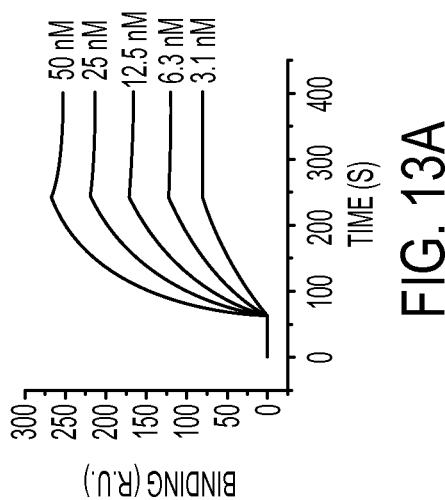

In addition, the binding of CNP-ITEM4 nanoparticles to the chip was proportional to the surface density of ITEM4, as CNP-ITEM4 (high) exhibited stronger binding compared to CNP-ITEM4 (low). To confirm the specificity of CNP-ITEM4 binding to the Fn14 Biacore chip, available Fn14 binding sites were first blocked with excess ITEM4 (500 nM) (FIG. 12A), after which CNP-ITEM4 (high) particles were allowed to bind to the chip (FIG. 12B). CNP-ITEM4 (high) bound to the Fn14 Biacore chip that was pretreated with control IgG, but not to the chip treated with excess ITEM4 (FIG. 12A-12B). To quantify the binding of various CNP-ITEM4 formulations to the Fn14 extracellular domain, their binding affinities ($K_D$) were determined by measuring the binding at various concentrations. The binding data and appropriate fitting procedures for ITEM4 and ITEM4-SH are provided in FIG. 13A-13C. FIG. 13A-13C are graphs that illustrate characterization of ITEM4 binding to Fn14. SPR analysis in FIG. 13A illustrates ITEM4 and in FIG. 13C ITEM-SH binding at various concentrations. In FIG. 13C, the equilibrium binding affinities for ITEM4 and ITEM4-SH were calculated from fitting SPR data.

Figure 14A:
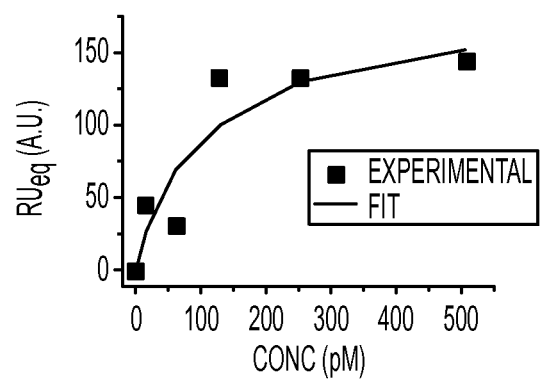
FIG. 14A-14B are graphs illustrating SPR analysis of CNP-ITEM4 nanoparticle binding to Fn14, according to an embodiment.
Figure 14B:
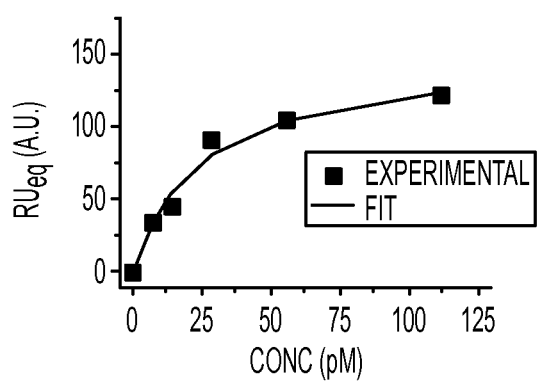

Characterization of CNP-ITEM4 nanoparticle binding to Fn14 is illustrated in FIG. 14A-14B. The measured $K_D$ for CNP-ITEM4 (low) and CNP-ITEM4 (high) were 106 pM (FIG. 14A) and 24 pM, (FIG. 14B) respectively. They were ~15- and ~65-fold higher than the binding affinity of ITEM4 alone. Tabulated $K_D$ values for the various ITEM4 and CNP formulations are provided in Table 3.

TABLE 3

Binding affinities ($K_D$) of nanoparticles to the Fn14 extracellular domain.

| Analyte | $K_D$, (nM) [a] |
|---|---|
| ITEM4 | 1.62 |
| ITEM4-SH | 1.57 |
| CNP-ITEM4 (low) | 0.106 |
| CNP-ITEM4 (high) | 0.024 |

[a] $K_D$ values determined on a per nanoparticle basis from fit of Biacore data.

Figure 15A:
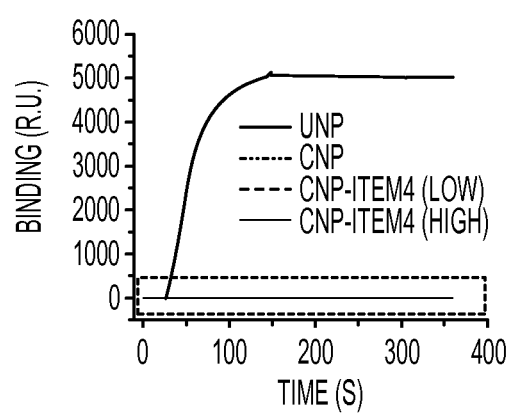
FIG. 15A-15B are graphs illustrating SPR analysis measuring the binding of (A) uncoated nanoparticles (UNP), CNP, CNP-ITEM4 (low), and CNP-ITEM4 (high) to mouse brain ECM chip. (B) Expanded view of boxed region in A, according to an embodiment.
Figure 15B:
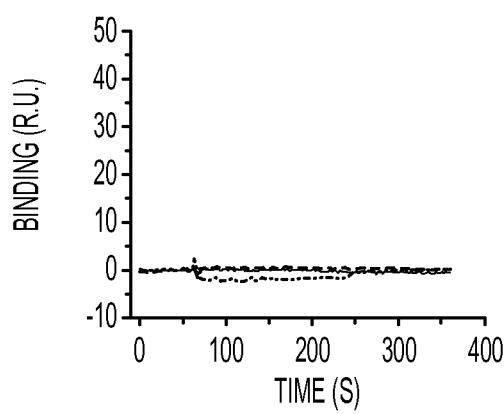

Example 14: Biacore Screening of Nanoparticles for Non-Specific Binding to Brain ECM Proteins To screen nanoparticles for non-specific binding to brain ECM, mouse brain ECM components were functionalized to the surface of a Biacore chip and the binding of various nanoparticle formulations was evaluated. As a positive control, the non-specific binding of uncoated nanoparticles (UNP) was measured, as these particles have been shown previously to be nearly completely immobilized when delivered into the rodent brain [34]. UNP bound strongly to the surface of the ECM Biacore chip (FIGS. 15A-15B), and these particles did not appreciably desorb from the chip with standard Biacore regeneration procedures (data not shown). Thus, a freshly prepared ECM Biacore chip was used for the remainder of the experiments. None of the CNP formulations that we studied (CNP, CNP-ITEM4 (low) and CNP-ITEM4 (high)) bound appreciably to the ECM chip, suggesting minimal non-specific interactions between the nanoparticles and the brain ECM proteins.

Example 15: Nanoparticle Uptake in Fn14-Negative and Fn14-Positive Cells

To confirm CNP-ITEM4 nanoparticle binding results from the Biacore assay, the cellular uptake of the CNP formulations was measured via flow cytometry. First, the uptake of CNP-ITEM4 was measured with two mouse embryonic fibroblast (MEF) cell lines: MEF 3.5−/− and MEF Fn14-V5. The MEF 3.5−/− cells were generated from Fn14-null mice and therefore do not express Fn14, as assayed by either Western blot analysis (FIG. 16A) or flow cytometry (FIG. 16B). MEF Fn14-V5 cells were produced via infection of the MEF 3.5−/− cell line with a lentivirus encoding human Fn14. Fn14 expression in these cells was confirmed by Western blot and flow cytometry assays (FIG. 16A-16B). CNP-ITEM4 nanoparticle uptake by the MEF cell lines was determined via flow cytometry. There was no difference in cellular uptake between CNP and CNP-ITEM4 (high) in MEF 3.5−/− cells; in contrast, CNP-ITEM4 (high) uptake was ~2.5-fold greater than CNP uptake when these nanoparticles were added to the MEF Fn14-V5 cells (FIG. 16C).

Second, nanoparticle uptake was examined in human U87-Luc/GFP GBM cells. These cells express Fn14, as measured by Western blotting (data not shown) and flow cytometry (FIG. 17A). A statistically significant increase in CNP uptake was observed in these cells with increasing ITEM4 density (FIG. 17B). Specifically, the cellular uptake efficiency of CNP-ITEM4 (low) and CNP-ITEM4 (high) was ~1.25-fold and ~3.5-fold higher, respectively, compared to CNP alone. To test whether the enhanced CNP-ITEM4 uptake was the result of a specific interaction between ITEM4 and Fn14, a competitive inhibition assay with free ITEM4 antibody was examined. Addition of excess free ITEM4 to cells, prior to particle addition, significantly inhibited the uptake of CNP-ITEM4 (high) to the same levels as that observed for non-targeted CNP (FIG. 17C). In contrast, no inhibition of CNP-ITEM4 uptake was observed when the same amount of IgG isotype control protein was preincubated with U87-Luc/GFP cells. To confirm that CNP-ITEM4 nanoparticles were internalized within cells and not solely associated with Fn14 on the cell surface, live-cell confocal microscopy imaging was performed (FIG. 17D-17G). Intracellular localization of CNP-ITEM4 was confirmed via z-stack analysis of cells stained with Hoechst 34580 (FIG. 17G).

Example 16: Nanoparticle Transport in Brain Tissue

Figure 18A:
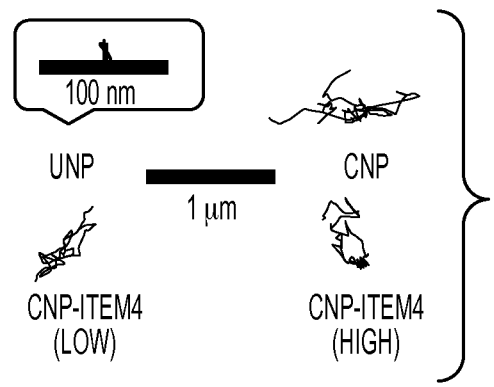
FIG. 18A-18C are images and graphs illustrating transport of uncoated nanoparticles (UNP), CNP, CNP-ITEM4 (low), and CNP-ITEM4 (high) nanoparticles in rat brain slices measured by MPT analysis, according to an embodiment.
Figure 18B:
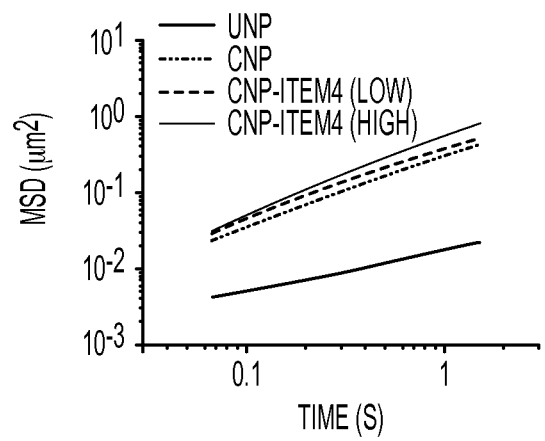
Figure 18C:
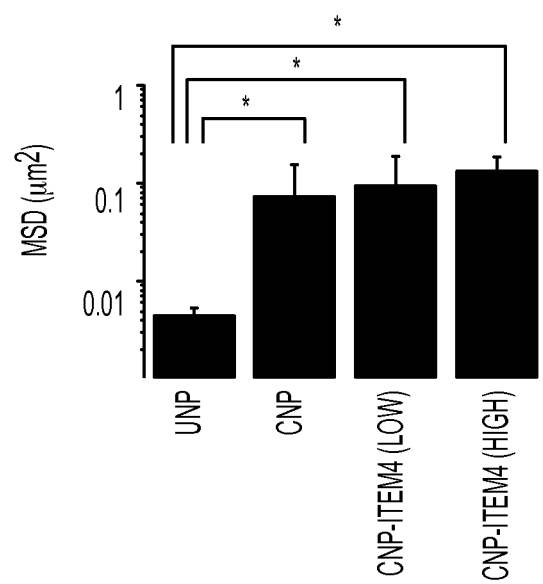
Figure 19:
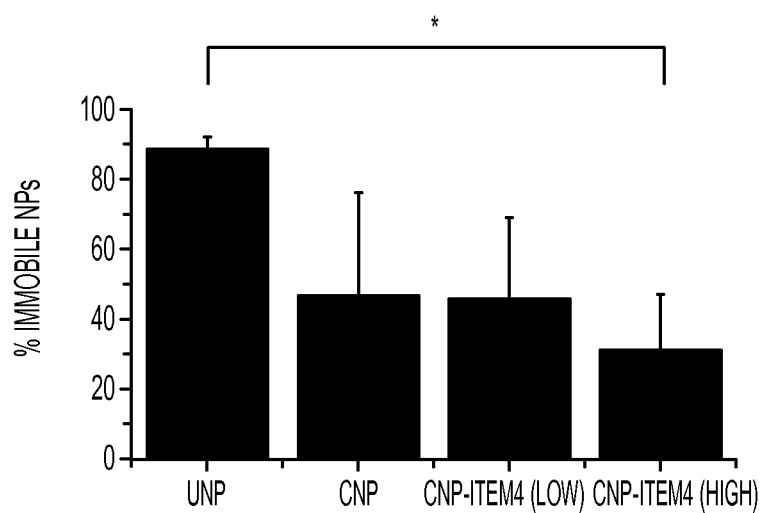
FIG. 19 is a graph illustrating MPT analysis of uncoated nanoparticles (UNP), CNP, CNP-ITEM4 (low), and CNP-ITEM4 (high) nanoparticles in rat brain slices, according to an embodiment.

MPT was used to test the diffusion rates of individual nanoparticles in ex vivo rat brain slices. Representative trajectories of nanoparticles are shown in FIG. 18A, from which it is clear that UNP were immobilized in brain tissue. In contrast, all three CNP formulations tested, CNP, CNP-ITEM4 (low) and CNP-ITEM4 (high), exhibited more diffusive Brownian-like trajectories. This can be quantitatively observed by the upward shift in the MSD vs time scale ($\tau$) curve for CNP, CNP-ITEM4 (low) and CNP-ITEM4 (high) compared to UNP (FIG. 18B). The calculated MSD at a time scale ($\tau$)=1 s for CNP formulations were more than an order of magnitude greater than UNP (FIG. 18C). The difference in the calculated MSD (at $\tau$=1) between UNP and all CNP formulations was statistically significant; however, there was no statistical difference between CNP, CNP-ITEM4 (low) and CNP-ITEM4 (high). The number of immobilized particles was estimated for each of the nanoparticle formulations based on the MPT transport data (FIG. 19).

The percentage of particles were classified as immobilized if the displayed MSD values at a time scale ($\tau$) of 1 second were less than the MSD for a particle that has moved one particle diameter from it's initial position. Nearly ~90% of UNP were effectively immobilized in brain tissue, whereas only 25% to 45% of CNP were immobile depending on the formulation; however, a statistically significant difference was only observed between UNP and CNP-ITEM4 (high).

Figure 20A:
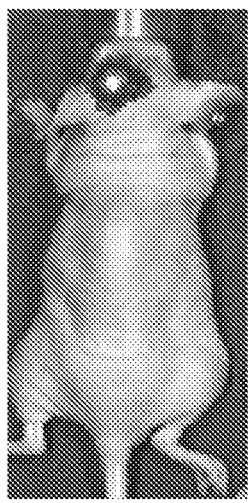
FIG. 20A-20B are photographs illustrating (A) BLI signal from a mouse bearing intracranial U87-luciferase glioma tumor and (B) fluorescent microscopy image of GFP-expressing U87 tumors, according to an embodiment.
Figure 20B:
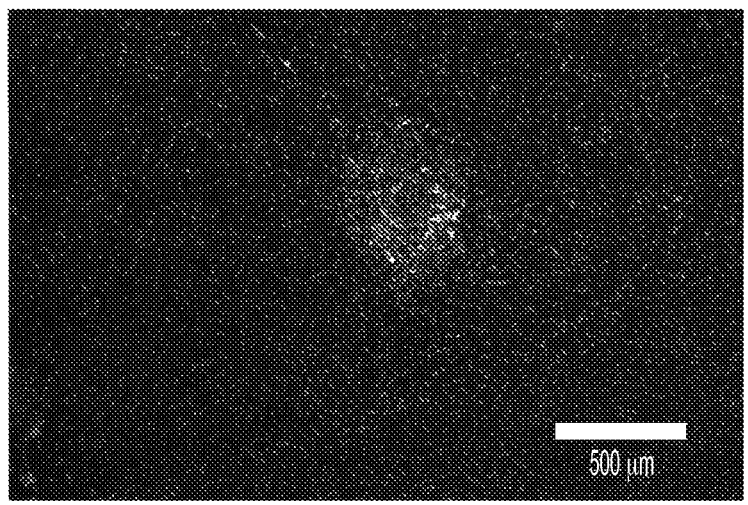
Figure 21D:
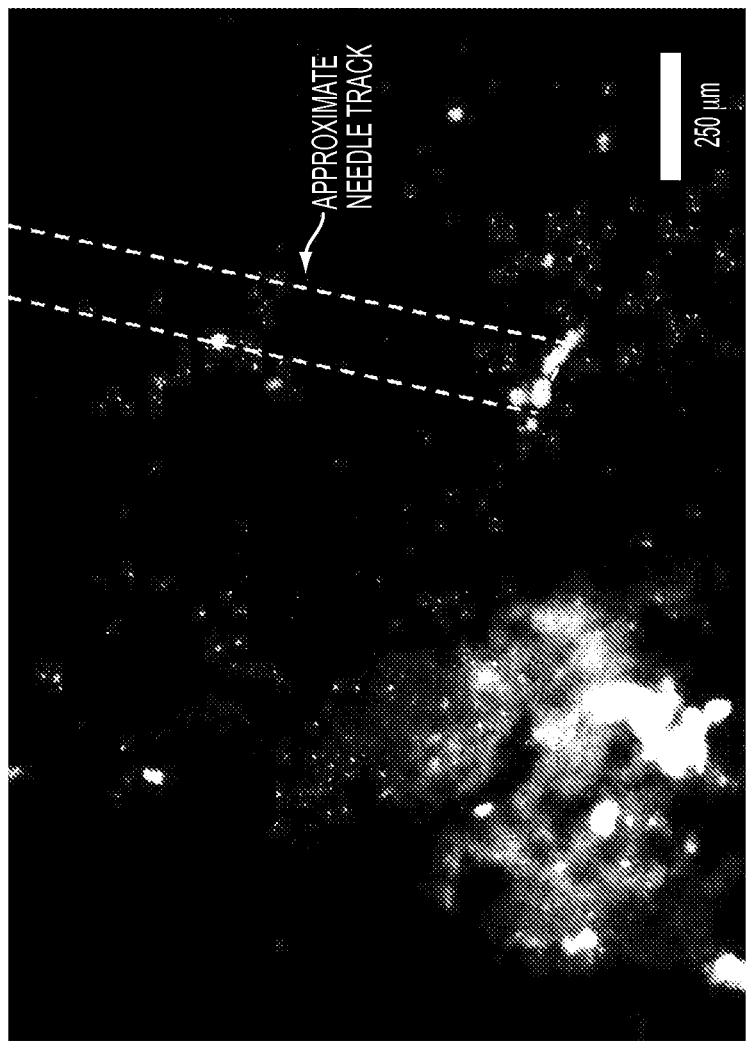
FIG. 21A-21D are photographs illustrating in vivo distribution of (A) untargeted CNPs, (B) CNP-ITEM4 nanoparticles, (C) GFP-expressing U87 cells and (D) merged image of B and C 24 hours following intracranial injection of particles at the similar stereotactic coordinates as the U87-Luc/GFP cell tumor implantation, according to an embodiment.
Figure 21A:
Figure 21B:
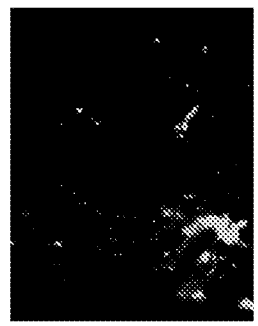
Figure 21C:
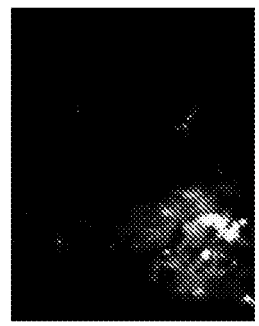

Example 17: Nanoparticle Distribution Following Intracranial Administration into Human GBM Xenografts To test the performance of Fn14-targeted nanoparticles in vivo, fluorescent nanoparticles—CNP and CNP-ITEM4 (high)—were administered to athymic nude mice bearing orthotopic U87-Luc/GFP GBM tumors. Luciferase- and GFP-expressing U87 tumor cells were evident in the brain 7 days after tumor implantation (FIG. 20A-20B). CNP and CNP-ITEM4 (high) nanoparticles were co-injected at the same stereotactic coordinates that were used for the tumor cell implantation. The mice were euthanized at 24 h after nanoparticle injection and brains were isolated. Cryosections were prepared and imaging conducted to assess tissue distribution of the nanoparticles and co-localization with the GFP-expressing brain tumor cells (FIG. 21A-21D). CNP and CNP-ITEM4 (high) nanoparticles were both distributed uniformly in the brain; however, a greater association of CNP-ITEM4 (high) was found with GFP-expressing tumor cells compared to untargeted CNP (FIG. 21D). These results demonstrate that our CNP-ITEM4 can penetrate within brain tissue and selectively target remote experimental GBM tumors.

Figure 22A:
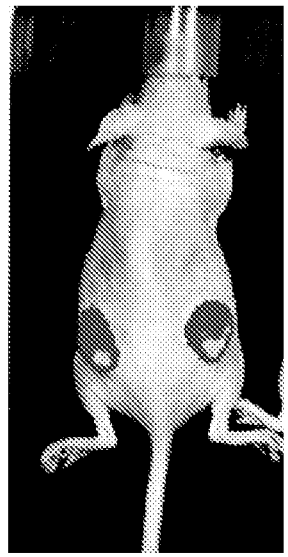
FIG. 22A-22C are photographs illustrating (A) BLI imaging of a mouse bearing both an Fn14+ and an Fn14− MDA-MB-231 breast cancer cell tumor (B-C) BLI imaging of organs and tumors harvested from tumor-bearing mice injected via the tail vein with either non-targeted CNPs (B) or CNP-ITEM4 (C) nanoparticles, according to an embodiment.
Figure 22B:
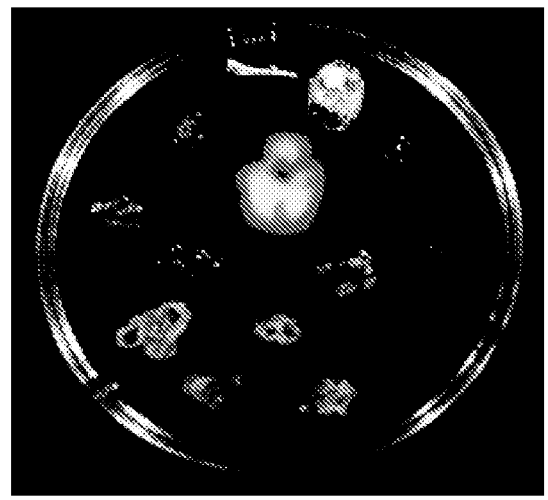
Figure 22C:
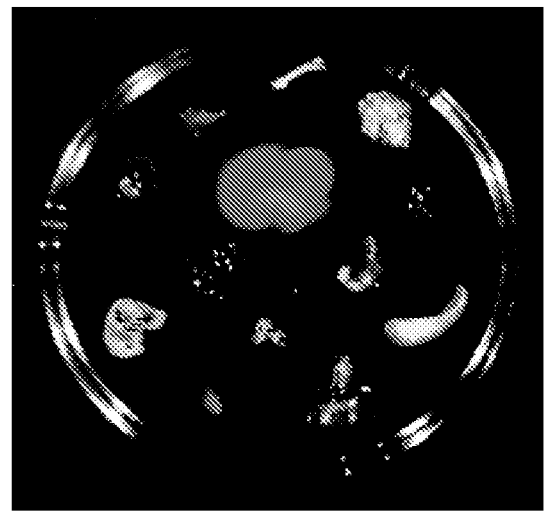

Example 18: Biodistribution of Non-Targeted and Fn14 Targeted Coated PS-PEG Nanoparticles after Systemic Delivery into Tumor-Bearing Mice Fn14-positive or Fn14-negative MDA-MB-231 luciferase cells were subcutaneously implanted in the right or left flank, respectively, of immunodeficient mice (FIG. 22A). Tumor growth was monitored by bioluminescence imaging (BLI), and when tumors were clearly visible either non-targeted coated nanoparticles or ITEM4-conjugated coated nanoparticles were injected via the tail vein. At 3 days, after injection, the mice were euthanized and organs and tumors were isolated and placed on a petri dish. Nanoparticle distribution was analyzed by BLI. Results for non-targeted (FIG. 22B) and Fn14-targeted (FIG. 22C) particles are shown. Tumor key: Solid circle=Fn14+ tumor; Stippled square=Fn14− tumor. Organ Key: 1=bone, 2=muscle, 3=brain, 4=lung, 5=liver, 6=heart; 7=kidney; 8=stomach, 9=intestine, 10=uterus, and 11=spleen.

REFERENCES

[1] Sambrook et al. Molecular Cloning: A Laboratory Manual, 2d ed., Cold Spring Harbor Laboratory Press, Cold Spring Harbor, N.Y. (1989).
[2] Ausubel et al., Current Protocols in Molecular Biology, Greene Publishing Associates (1992, and Supplements to 2002).
[3] Harlow and Lan, Antibodies: A Laboratory Manual, Cold Spring Harbor Laboratory Press, Cold Spring Harbor, N.Y. (1990).
[4] Principles of Neural Science, 4th ed., Eric R. Kandel, James H. Schwart, Thomas M. Jessell editors. McGraw-Hill/Appleton & Lange: New York, N.Y. (2000).
[5] Nikolaev A, McLaughlin T, O'Leary D, Tessier-Lavigne M. APP binds DR6 to cause axon pruning and neuron death via distinct caspases. *Nature*. 19 Feb. 2009: 457 (7232): 981-989. doi:10.1038/nature07767. PMID 19225519.).
[6] Current Drug Targets—CNS & Neurological Disorders, 2004, 3, 153-160 2004 Bentham Science Publishers Ltd; and Programmed Axon Death, Synaptic Dysfunction and the Ubiquitin Proteasome System M. P. Coleman1 and R. R. Ribchester.)
[7] Bonelli and Hofmann (2004), Expert Opin Pharmacother, 5, 767-76).
[8] Karpuj, et al. (2002), Nat Med, 8, 143-9).
[9] Fauci, A. S. et al., *Harrison's Principles of Internal* McGraw-Hill, 14th Edition (1998), page 2321.
[10] Winkles, J. A., *The TWEAK-Fn14 cytokine-receptor axis: discovery, biology and therapeutic targeting.* Nat Rev Drug Discov, 2008. 7(5): p. 411-25.
[11] Cheng, E., et al., *TWEAK/Fn14 Axis-Targeted Therapeutics: Moving Basic Science Discoveries to the Clinic.* Front Immunol, 2013. 4: p. 473.
[12] Tran, N. L., et al., *Increased fibroblast growth factor-inducible 14 expression levels promote glioma cell invasion via Rac1 and nuclear factor-kappaB and correlate with poor patient outcome.* Cancer Res, 2006. 66(19): p. 9535-42.
[13] Fortin, S. P., et al., *Tumor necrosis factor-like weak inducer of apoptosis stimulation of glioma cell survival is dependent on Akt2 function.* Mol Cancer Res, 2009. 7(11): p. 1871-81.
[14] Zhou, H., et al., *The TWEAK receptor Fn14 is a therapeutic target in melanoma: immunotoxins targeting Fn14 receptor for malignant melanoma treatment.* J Invest Dermatol, 2013. 133(4): p. 1052-62.
[15] Zhou, H., et al., *Development and characterization of a potent immunoconjugate targeting the Fn14 receptor on solid tumor cells.* Mol Cancer Ther, 2011. 10(7): p. 1276-88.
[16] Zhou, H., et al., *Antitumor activity of a humanized, bivalent immunotoxin targeting fn14-positive solid tumors.* Cancer Res, 2013. 73(14): p. 4439-50.
[17] Sampson, J. H., et al., *Poor drug distribution as a possible explanation for the results of the PRECISE trial.* J Neurosurg, 2010. 113(2): p. 301-9.
[18] Tobias, A., et al., *The art of gene therapy for glioma: a review of the challenging road to the bedside.* J Neurol Neurosurg Psychiatry, 2013. 84(2): p. 213-22.
[19] Zhou, J., et al., *Highly penetrative, drug-loaded nanocarriers improve treatment of glioblastoma.* Proc Natl Acad Sci USA, 2013. 110(29): p. 11751-6.
[20] Voges, J., et al., *Clinical protocol. Liposomal gene therapy with the herpes simplex thymidine kinase gene/ganciclovir system for the treatment of glioblastoma multiforme.* Hum Gene Ther, 2002. 13(5): p. 675-85.
[21] Voges, J., et al., *Imaging-guided convection-enhanced delivery and gene therapy of glioblastoma.* Ann Neurol, 2003. 54(4): p. 479-87.
[22] Woodworth, G. F., et al., *Emerging insights into barriers to effective brain tumor therapeutics.* Front Oncol, 2014. 4: p. 126.
[23] Tzeng, S. Y. and J. J. Green, *Therapeutic nanomedicine for brain cancer.* Ther Deliv, 2013. 4(6): p. 687-704.
[24] Veiseh, O., et al., *Specific targeting of brain tumors with an optical/magnetic resonance imaging nanoprobe across the blood-brain barrier.* Cancer Res, 2009. 69(15): p. 6200-7.

[25] Madhankumar, A. B., et al., *Interleukin-13 receptor-targeted nanovesicles are a potential therapy for glioblastoma multiforme*. Mol Cancer Ther, 2006. 5(12): p. 3162-9.

[26] Sykova, E. and C. Nicholson, *Diffusion in brain extracellular space*. Physiol Rev, 2008. 88(4): p. 1277-340.

[27] Zimmermann, D. R. and M. T. Dours-Zimmermann, *Extracellular matrix of the central nervous system: from neglect to challenge*. Histochem Cell Biol, 2008. 130(4): p. 635-53.

[28] Vargova, L., et al., *Diffusion parameters of the extracellular space in human gliomas*. Glia, 2003. 42(1): p. 77-88.

[29] Willis, A. L., et al., *The fibroblast growth factor-inducible 14 receptor is highly expressed in HER2-positive breast tumors and regulates breast cancer cell invasive capacity*. Mol Cancer Res, 2008. 6(5): p. 725-34.

[30] Yin, J., et al., *AR-Regulated TWEAK-FN14 Pathway Promotes Prostate Cancer Bone Metastasis*. Cancer Res, 2014. 74(16): p. 4306-17.

[31] Whitsett, T. G., et al., *Elevated expression of Fn14 in non-small cell lung cancer correlates with activated EGFR and promotes tumor cell migration and invasion*. Am J Pathol, 2012. 181(1): p. 111-20.

[32]. Lai, S. K., et al., *Rapid transport of large polymeric nanoparticles in fresh undiluted human mucus*. Proc Natl Acad Sci USA, 2007. 104(5): p. 1482-7.

[33] Popielarski, S. R., S. H. Pun, and M. E. Davis, *A nanoparticle-based model delivery system to guide the rational design of gene delivery to the liver. 1. Synthesis and characterization*. Bioconjug Chem, 2005. 16(5): p. 1063-70.

[34] Nance, E. A., et al., *A dense poly(ethylene glycol) coating improves penetration of large polymeric nanoparticles within brain tissue*. Sci Transl Med, 2012. 4(149): p. 149ra119.

[35] Bobo, R. H., et al., *Convection-enhanced delivery of macromolecules in the brain*. Proc Natl Acad Sci USA, 1994. 91(6): p. 2076-80.

[36] Kunwar, S., et al., *Phase III randomized trial of CED of IL13-PE38QQR vs Gliadel wafers for recurrent glioblastoma*. Neuro Oncol, 2010. 12(8): p. 871-81.

[37] Brown, S. A., et al., *TWEAK binding to the Fn14 cysteine-rich domain depends on charged residues located in both the A1 and D2 modules*. Biochem J, 2006. 397(2): p. 297-304.

[38] Medberry, C. J., et al., *Hydrogels derived from central nervous system extracellular matrix*. Biomaterials, 2013. 34(4): p. 1033-40.

[39]. Gurunathan, S., et al., *Regulation of fibroblast growth factor-inducible 14 (Fn14) expression levels via ligand-independent lysosomal degradation*. J Biol Chem, 2014. 289(19): p. 12976-88.

[40] Schuster, B. S., et al., *Overcoming the Cystic Fibrosis Sputum Barrier to Leading Adeno-associated Virus Gene Therapy Vectors*. Mol Ther, 2014. 22(8): p. 1484-93.

[41] Kim, A. J., et al., "Highly compacted pH-responsive DNA nanoparticles mediate transgene silencing in experimental glioma," J. Mater. Chem. B, 2014, 2, 8165-8173, (2014)

[42] Dhruv, H., et al., *Structural basis and targeting of the interaction between fibroblast growth factor-inducible 14 and tumor necrosis factor-like weak inducer of apoptosis*. J Biol Chem, 2013. 288(45): p. 32261-76.

[43] Stupp, R., et al., *Radiotherapy plus concomitant and adjuvant temozolomide for glioblastoma*. N Engl J Med, 2005. 352(10): p. 987-96.

[44] Fung, L. K., et al., *Chemotherapeutic drugs released from polymers: distribution of 1,3-bis(2-chloroethyl)-1-nitrosourea in the rat brain*. Pharm Res, 1996. 13(5): p. 671-82.

[45] S. Y. Feng, Y. Guo, V. M. Factor, S. S. Thorgeirsson, D. W. Bell, J. R. Testa, et al., The Fn14 immediate-early response gene is induced during liver regeneration and highly expressed in both human and murine hepatocellular carcinomas, Am. J. Pathol. 156 (2000) 1253-1261.

[46] J. S. Michaelson, S. Cho, B. Browning, T. S. Zheng, J. M. Lincecum, M. Z. Wang, et al., Tweak induces mammary epithelial branching morphogenesis, Oncogene 24 (2005) 2613-2624.

[47] Hadjipanayis, C. G., et al., *EGFRvIII antibody-conjugated iron oxide nanoparticles for magnetic resonance imaging-guided convection-enhanced delivery and targeted therapy of glioblastoma*. Cancer Res, 2010. 70(15): p. 6303-12.

[48] Pang, Z., et al., *Enhanced intracellular delivery and chemotherapy for glioma rats by transferrin-conjugated biodegradable polymersomes loaded with doxorubicin*. Bioconjug Chem, 2011. 22(6): p. 1171-80.

[49] Reardon, D. A., et al., *Phase II trial of murine (131)I-labeled antitenascin monoclonal antibody 8106 administered into surgically created resection cavities of patients with newly diagnosed malignant gliomas*. J Clin Oncol, 2002. 20(5): p. 1389-97.

[50] Rich, J. N. and D. D. Bigner, *Development of novel targeted therapies in the treatment of malignant glioma*. Nat Rev Drug Discov, 2004. 3(5): p. 430-46.

[51] Sampson, J. H., et al., *Immunologic escape after prolonged progression free survival with epidermal growth factor receptor variant III peptide vaccination in patients with newly diagnosed glioblastoma*. J Clin Oncol, 2010. 28(31): p. 4722-9.

[52] Kim, A. J., et al., *Use of single-site-functionalized PEG dendrons to prepare gene vectors that penetrate human mucus barriers*. Angew Chem Int Ed Engl, 2013. 52(14): p. 3985-8.

[53] Ensign, L. M., et al., *Mucus-penetrating nanoparticles for vaginal drug delivery protect against herpes simplex virus*. Sci Transl Med, 2012. 4(138): p. 138ra79.

[54] Meighan-Mantha R L, Hsu D K W, Guo Y, Brown S A N, Feng S Y, Peifley K A, Alberts G F, Copeland N G, Gilbert D J, Jenkins N A, Richards C M and Winkles J A. (1999). The mitogen-inducible Fn14 gene encodes a type I transmembrane protein that modulates fibroblast adhesion and migration. J Biol Chem 274:33166-33176.

[55] Bruce, J. N., et al., *Regression of recurrent malignant gliomas with convection-enhanced delivery of topotecan*. Neurosurgery, 2011. 69(6): p. 1272-9; discussion 1279-80.

[56] Playfer, J. R., *Parkinson's Disease*, Postgrad Med J, 73; 257-264:1997 and Nadeau, S. E., *Parkinson's Disease*, J Am Ger Soc, 45; 233-240:1997.

[57] Nakayama, M., et al., *Fibroblast growth factor-inducible 14 mediates multiple pathways of TWEAK-induced cell death*. J Immunol, 2003. 170(1): p. 341-8.

[58] Wen, P. Y. and S. Kesari, *Malignant gliomas in adults*. N Engl J Med, 2008. 359(5): p. 492-507.

[59] Brem, H., et al., *Placebo-controlled trial of safety and efficacy of intraoperative controlled delivery by biodegradable polymers of chemotherapy for recurrent gliomas. The Polymer-brain Tumor Treatment Group*. Lancet, 1995. 345(8956): p. 1008-12.

[60] Tate, M. C. and M. K. Aghi, *Biology of angiogenesis and invasion in glioma.* Neurotherapeutics, 2009. 6(3): p. 447-57.

[61] Jain, K. K., *Nanobiotechnology-based strategies for crossing the blood-brain barrier.* Nanomedicine (Lond), 2012. 7(8): p. 1225-33.

[62] Ulbrich, K., et al., *Transferrin-and transferrin-receptor-antibody-modified nanoparticles enable drug delivery across the blood-brain barrier (BBB).* Eur J Pharm Biopharm, 2009. 71(2): p. 251-6.

[63] Vykhodtseva, N., N. McDannold, and K. Hynynen, *Progress and problems in the application of focused ultrasound for blood-brain barrier disruption.* Ultrasonics, 2008. 48(4): p. 279-96.

[64] Nance, E., et al., *Non-invasive delivery of stealth, brain penetrating nanoparticles across the blood-brain barrier using MRI-guided focused ultrasound.* J Control Release, 2014. 189: p. 123-32.

[65] Kroll, R. A. and E. A. Neuwelt, *Outwitting the blood-brain barrier for therapeutic purposes: osmotic opening and other means.* Neurosurgery, 1998. 42(5): p. 1083-99; discussion 1099-100.

[66] Allard, E., C. Passirani, and J. P. Benoit, *Convection-enhanced delivery of nanocarriers for the treatment of brain tumors.* Biomaterials, 2009. 30(12): p. 2302-18.

What is claimed is:

1. A drug delivery nanoparticle, comprising:
   (a) a nanoparticle having a hydrodynamic diameter of between 110 nm and 115 nm;
   (b) a coating of polyethylene glycol with a surface density of about at least about 0.1 polyethylene glycol molecules per $nm^2$;
   (c) an anti-Fn14 antibody that specifically binds to the cell surface of a tumor cell, wherein the anti-Fn14 antibody is present on the surface of the nanoparticle at a density of between about 11 anti-Fn14 antibody molecules per nanoparticle to about 56 anti-Fn14 antibody molecules per nanoparticle; and
   (d) a therapeutic agent, wherein the nanoparticle penetrates extracellular matrix, wherein the nanoparticle has minimal non-specific binding to extracellular matrix.

2. The drug delivery nanoparticle of claim 1, wherein the target tumor cell is selected from the group consisting of a bladder, brain, breast, cervical, colorectal, esophageal, liver, lung, skin, ovarian, pancreatic, prostate, renal, testicular, bone, liver, and lymph node cell.

3. The drug delivery nanoparticle of claim 1, wherein the tumor cell is a glioblastoma cell.

4. The drug delivery nanoparticle of claim 1, wherein the nanoparticle is formed from a biodegradable polymer selected from the group consisting of poly-D-L-lactide-co-glycolide (PLGA); polylactic acid (PLA); poly-ε-caprolactone (PCL); chitosan, gelatin, albumin, and poly-alkyl-cyano-acrylates (PAC).

5. The drug delivery nanoparticle of claim 1, wherein the Fn14-binding antibody is an Fn14 monoclonal antibody or fragment thereof.

6. The drug delivery nanoparticle of claim 5, wherein the anti-Fn14 antibody is selected from the group consisting of ITEM4, ITEM-4-SH, ITEM4 scFv, and ITEM4 Fab.

7. The drug delivery nanoparticle of claim 1, wherein the therapeutic agent is selected from the group consisting of cisiplatin, doxorubicin, etoposide, and paclitaxel.

8. The drug delivery nanoparticle of claim 1, wherein the nanoparticle releases an effective amount of the biologically active agent over a period of at least four hours.

9. A pharmaceutical composition, comprising a pharmaceutically acceptable vehicle and a drug delivery nanoparticle of claim 1.

10. A kit comprising the pharmaceutical composition of claim 9.

11. A method for treating a tumor of the brain, lung, or breast, the method comprising administering to a patient in need thereof an effective amount of the drug delivery nanoparticle of claim 1.

12. The method of claim 11, wherein the nanoparticle is administered locally to the brain.

13. The method of claim 11, wherein the nanoparticle is administered systemically and the nanoparticle penetrates the brain by passing through the blood-brain-barrier and then extracellular matrix.

14. The method of claim 11, wherein the tumor is glioblastoma.

* * * * *